US011771092B2

(12) United States Patent
Watts

(10) Patent No.: US 11,771,092 B2
(45) Date of Patent: *Oct. 3, 2023

(54) MODIFIED VIP3 POLYPEPTIDES

(71) Applicant: Syngenta Participations AG, Basel (CH)

(72) Inventor: Joseph M Watts, Research Triangle Park, NC (US)

(73) Assignee: Syngenta Participations AG, Basel (CH)

(*) Notice: Subject to any disclaimer, the term of this patent is extended or adjusted under 35 U.S.C. 154(b) by 192 days.

This patent is subject to a terminal disclaimer.

(21) Appl. No.: 17/317,185

(22) Filed: May 11, 2021

(65) Prior Publication Data

US 2021/0267215 A1 Sep. 2, 2021

Related U.S. Application Data

(60) Continuation of application No. 16/533,950, filed on Aug. 7, 2019, now Pat. No. 11,028,134, which is a division of application No. 15/506,320, filed as application No. PCT/US2015/047071 on Aug. 27, 2015, now Pat. No. 10,421,791.

(60) Provisional application No. 62/043,922, filed on Aug. 29, 2014.

(51) Int. Cl.
| *A01N 63/50* | (2020.01) |
| *A01N 37/46* | (2006.01) |
| *C07K 14/325* | (2006.01) |
| *C12N 15/82* | (2006.01) |
| *A01N 63/10* | (2020.01) |
| *C07K 14/195* | (2006.01) |
| *C07K 14/32* | (2006.01) |

(52) U.S. Cl.
CPC .............. *A01N 63/50* (2020.01); *A01N 37/46* (2013.01); *A01N 63/10* (2020.01); *C07K 14/195* (2013.01); *C07K 14/32* (2013.01); *C07K 14/325* (2013.01); *C12N 15/8279* (2013.01); *C12N 15/8286* (2013.01); *C07K 2319/20* (2013.01); *C07K 2319/55* (2013.01); *Y02A 40/146* (2018.01)

(58) Field of Classification Search
CPC ....................................................... A01N 63/50
USPC ........................................................ 800/279
See application file for complete search history.

(56) References Cited

U.S. PATENT DOCUMENTS

| 5,877,012 | A | 3/1999 | Estruch et al. |
| 7,378,493 | B2* | 5/2008 | Shen ..................... C07K 14/32 424/405 |
| 10,421,791 | B2* | 9/2019 | Watts ................. C12N 15/8279 |
| 11,028,134 | B2* | 6/2021 | Watts ................. C12N 15/8286 |
| 2005/0210545 | A1 | 9/2005 | Shen et al. |
| 2014/0223602 | A1 | 8/2014 | Chang et al. |

FOREIGN PATENT DOCUMENTS

| WO | 2012138703 A1 | 10/2012 |
| WO | 2013122720 A2 | 8/2013 |

OTHER PUBLICATIONS

Bae et al. J. Biol. Chem. 283:12415-12425 (Year: 2008).*
Palma I et al., "Vip3C, a Novel Class of Vegetative Insecticidal Proteins from Bacillus thuringiensis", Applied and Environmental Microbiology, Oct. 2012, vol. 78, No. 19, pp. 7163-7165.
Fang J.et al., "Characterization of Chimeric Bacillus thuringiensis Vip3 Toxins", Applied and Environmental Microbiology, Feb. 2007, vol. 73, No. 3, pp. 956-961.
Maissa Chakroun et al: "Bacterial Vegetative Insecticidal Prteins (Vip) from Entomopathogenic Bacteria", Microbiology and molecular biology revies: MMBR 1. Jun. 2016, pp. 329-350, CP055430565.
Liu et al., J. Bacteriol., 194: pp. 1841-1842, 2012.
International Search Report & Written Opinion for PCT/US2015/047071, dated Jan. 11, 2016.
Extended European Search Report of EP15836257.4 dated Dec. 13, 2017.
Fang Dong et al: "Fusing the vegetative insecticidal protein Vip3Aa7 and the N terminus of Cry9Ca improves toxicity againstlarvae", applied Microbiology and Biotechnology, Springer, Berlin, DE, vol. 96, No. 4, Jun. 21, 2012, pp. 921-929, XP035129212, ISSN: 1432-0614.
De Maagd Rud A et al: "Domain III substitution in Bacillus thuringiensis delta-endotoxin CrylA(b) results in superior toxicity for Spodoptera exigua and altered membrane protein recognition", applied and Environmental Microbiology, vo. 62, No. 5, May 1, 1996, pp. 1537-1543, XP002209205.
"Carbohydrate-Binding Module", Wikipedia, 2019, pp. 1-21.

* cited by examiner

*Primary Examiner* — Li Zheng
(74) *Attorney, Agent, or Firm* — Katherine Seguin

(57) ABSTRACT

The present invention is directed to the vegetative insecticidal proteins (Vips) modified to comprise heterologous bacterial carbohydrate binding modules and the methods of use thereof. Expression of modified proteins resulted in variations to activity against lepidopteran pest species of agricultural importance such as Corn earworm and Fall armyworm conveying broad spectrum insect control.

15 Claims, 5 Drawing Sheets

Specification includes a Sequence Listing.

FIG. 3

```
                2ZEX PGFEIDGLDSWQDMQQD-MSAVPEAAHNGALGLKIKGGKAAGGQDIPLKPN-TTYIIGAWAKFDSKPAGTFDVVQ
       YP003011283.1_CENC PGLEDGINNWQAMGEG-FTAASDMSHTGSASLKVLLN--NGGRQVVALQPG-KSYKLGVWGKTAGTGIGTQTATVM
       YP005220866.1_GP21 PSFERGTEGYTGWSGIATVVTLQVPHLGTKAAKLAAGGSAGVGQKISFKKD-RSYKIGIWAKQDPNTTIQSTDNTK
       ZP08510134.1_PSHGF7 PGFEIDNLASWINWGN----TSSVTISPAFAGAKAARIASG-EGGAQQIIPGIPSGTTYVLSGHG---SVSAGTIDTAIVG

2ZEX YHLKDANN--------TYVQHILNFNETDWIYKQLLFTTPDVFGSTPQLALWKGJTSKAN-LYVDDVYLVEV
       YP003011283.1_CENC INYKKPEDDSS-HTYGSFQFGPDNSEFTYKEITFETPDDMAQEWGTQFVSIWSEGADQVYLDDFTILSEV
       YP005220866.1_GP21 FRVADQNGLIASKAYGPFTSNWQEVSWIWKATRDVIADVQ------FTAFLSAGAMYFDDEYVVDV
       ZP08510134.1_PSHGF7 VDCLIDANNN-----VLAKNTLRFNQTLYEFKSTAFTTVFGT-AKLQVTYKNADSGAN-AFLDDLSI--

VIP3D 541
         _____
        2ZEX 629
   P021_VIP3D FTSNIVEN-GSTEEDNLEPWKANKN---------AYVDHTGVNGHKALYVHKDG---------GESQFIGEDKLKPKTIEYVIQYIVGKP
   2ZEX| FTSNIVEN-PGFEIDGLDSWQDMQQD---MSAVPEAAHNGALGLKIKGGKAA----GGGQDIPLKPN--TTYILGAWAKFDSK
         4 RESIDUES FROM
        2ZEX   AAD09354 "2ZEZ" 767
        2ZEZ| FTSNIVEN-PGFENGMDGWFDMGYP---------VSAVPEAAYGGTIKGEKLSGEKQA----GMGQKVALKPN--TTYILGAWEKFTAK
```

FIG. 5A

```
                                                                                    VIP3D 668
                                                                                       _____
                                                                                              2ZEX 756
                                                                                                    _____
                                                                               ACCESSION AAD09354 "2ZEZ" 899
   P021_VIP3D -----------SIHLK----D-----ENIGYIHYEDINNNLKDYQTIKRFTTGIDLKGVLILKS------QNGDE-AWGDKFTILEIKPAEDILS
   2ZEX| PAGT-FDVVQYHLK------DANNTYVQHILNFNETDWIYKQLLFTTPDVFGSTPQLALWKGDT----SKAN--LYVDDVYLVEVKPAEDILS
   2ZEZ| PGTY-CDVIVQYHLK-----DANNTYVQHILRFTETDWIYKQVVFTTPDAFGSDPEFVLMKDDA-----SNAD--RYADNITLVEVKPAEDILS
```

```
             505 FROM ACCESSION NO_229032
              |
1OFE | FTSNIVENDESSPEEVKNMWNSGTWQAEFGSPDIEMNGEVGNGALQINVKLPGKSIW----------EEVRVARKFERLSECEILEYDIYIPNVEGL
             45 FROM ACCESSION AAC44232.1
              |
1PMH | FTSNIVENDFEDGTVMSFGEAWGDSLKCIKKVSVSQDLQRPGNKYALRLDVEFNPNNGMDQGEDIGTWIGGVVEGQDFTGYKSVEFFMFIPYDEFS
           208 FROM AAO31761.1
              |
2BGP | FTSNIVEN--TAASASITAPQLVG----------NVGEIQCAG--SAVTWN----------VDVPVTGEYRINLIT----WS

655
                                                                                               |
1OFE | KGR-LRPYAVILNPGWVKIGHLDMNANVESAEITTFGGKEYRRFHVRLEFDRTAGVKELLHIGVVGDH----------LRYDGPFFTLDNVRLYKRKPAEDLLS
                                                                                    218
                                                                                     |
1PMH | KSQGGFAYKVVINDGNKEILGSEFNITANAGKKVKINGKDYTVIHKAFAIPEDFRTKKRAQLVFQFAGQNSNYKGPIYLDNVRIRPEKPAEDLLS
                                                                      319
                                                                       |
2BGP | SPY-SSKVNITLMDGT----------ALSYAFAFAEATVPVTVYQIKTLSAGN----------HSFGVRVGSSDWGY----------MNVHS----------LKLELLGKPAEDLLS
```

*FIG. 5B*

```
GP21    | 69 FROM YP_005220866.1
          FTSNIVEN-PSFERGTEGYTGMSGIA--------TVVTLQVFHLGTKAAKLAAGGSA---------GVGQKISFKKD-RSYKIGIWAKQDEN
CENC    | 202 FROM YP_003011283.1
          FTSNIVEN-PGLEDGINMQAWGEG---------FTAASDMSHIGSASLKVLINN-----------GGRQVVALQPG-KSYKLGVWGKTAGT
PSHGF7  | 66 FROM WP_009674454.1
          FTSNIVEN-PGEEDNLASMTNMGN---------TSSVTSPAFAGAKAARIASGE-G---------GAGQITPGIPSGTTYVLSGHGSVSAG
1WKY    | 345 FROM AAC44232.1
          FTSNIVEN---DFEESTQWTGSSLSR-------GPWIVTEWSSKGNHSLKADIQMSSNSQ-----HYLHVIQNRSLQQNSRIQATVKHANW

203
GP21    | --------TTTQSTDNTKFRVA--------DQNGLIASKAYGPFTSNMQEVSWTWKATRDVLADVQFTAF--L---SACQA-MYFDDFYVVDVKPAEDLL
                                                                                              341
CENC    | GIGT-QTATVMINYKKPED--------DSSHTYGSFQFGPDNSEFTYKEITEEIPDMAQEMGIQFVSIWS---EGADQ-VYLDFTLSEVKPAEDLL
                                                                                              195
PSHGF7  | ----TD--TAIVGVDCLD----------ANNNVLAKNTLRFNQILYEFKSTAFTTVPGT-AKLQVYTYKNAD----SGAN--AFLDLSLMEVKPAEDLL
                                                                                              490
1WKY    | GSVG--NGMTARLYVKTIG--------HGYTWYSGSFVPINGSSGTTLSLDLSNVQNLSQVREIGVQFQSE-----SNSSGQTSIYIDNVIVEKPAEDLL
```

FIG. 5C

MODIFIED VIP3 POLYPEPTIDES

RELATED APPLICATION INFORMATION

This application is a continuation of U.S. application Ser. No. 16/533,950, now U.S. Pat. No. 11,028,134, filed Aug. 7, 2019, which is a divisional application of U.S. application Ser. No. 15/506,320 now U.S. Pat. No. 10,421,791, filed on Feb. 24, 2017, which is a 371 of International Application No. PCT/US2015/047071, filed Aug. 27, 2015, which claims priority to U.S. Provisional Application No. 62/043,922, filed Aug. 29, 2014, all of which are hereby incorporated by reference herein in their entirety.

STATEMENT REGARDING ELECTRONIC FILING OF A SEQUENCE LISTING

A Sequence Listing in ASCII text format, submitted under 37 C.F.R. § 1.821, entitled 80380sequences.txt, 334 kilobytes in size, generated May 7, 2021, and filed via EFS-Web, is provided in lieu of a paper copy. This Sequence Listing is hereby incorporated herein by reference into the specification for its disclosures.

FIELD OF THE INVENTION

The invention relates to vegetative insecticidal proteins (Vip) modified to comprise heterologous carbohydrate binding modules and methods of use thereof.

BACKGROUND OF THE INVENTION

*Bacillus thuringiensis* (Bt) are ubiquitous soil dwelling, gram positive spore-forming bacteria. Bt produces protein toxins which are orally active and highly specific for individual insect orders and species (K. van Frankenhuyzen., *J. Invertebr. Pathol.* 101, 1-16 (2009)). Thus, Bt proteins and the bacilli that produce them have been utilized in agriculture since the 1920s for control of insect pests (J. Lord, *J Invertebr Pathol.* 89, 19-29 (2005)). To ease field application and to target plant tissues not readily protected by foliar application, select proteins have been transgenically expressed in crops widely since the 1990s.

Bt produces three known classes of insecticidal protein toxins: crystal (Cry), cytolytic (Cyt), and vegetative insecticidal proteins (Vip). Cry proteins are produced as parasporal intracellular inclusion bodies with microscopic crystal morphology. Cyt proteins do not share sequence homology with the Cry proteins but are similarly produced as inclusion bodies during sporulation. Vip proteins are soluble toxins from Bt which are produced throughout the vegetative life cycle of the bacteria (A. Bravo et al. *Insect Biochem Mol Biol.* 41(7):423-31 (2011)).

Biological pest control agents, such as *Bacillus thuringiensis* strains expressing pesticidal polypeptides have been applied to crop plants with satisfactory results, thus offering an alternative or compliment to chemical pesticides. The expression of Cry proteins in transgenic plants has provided efficient protection against certain insect pests, and transgenic plants expressing such proteins have been commercialized, allowing farmers to reduce or eliminate applications of chemical insect control agents.

Vip3 is a specific class of vegetative insecticidal protein, which has broad toxicity against lepidopteran pest species and is amenable to transgenic plant expression (J. Estruch et al. *Proc Natl Acad Sci USA* 93, 5389-94 (1996)). The first product containing Vip3 was genetically modified corn sold under the brand name AGRISURE VIPTERA™ by Syngenta in 2011 (See also Syngenta U.S. Pat. Nos. 7,378,493 and 7,244,820). Nevertheless, compared to the vast peer reviewed literature on the Cry proteins, relatively little is reported for the Vip3 proteins. Vip3 proteins share no homology with Cry or Cyt proteins. Vip3 does not BLAST to any other confirmed proteins in the nr protein database with expect values less than 1.0. Currently reported sequences indicate far less sequence variation between the Vip3 proteins compared to variation observed for the Cry proteins.

Vip3 proteins are approximately 88 kDa in size and are produced and secreted by *Bacillus* during its vegetative stage of growth (vegetative insecticidal proteins, Vip). The Vip3A protein possesses insecticidal activity against a wide spectrum of lepidopteran pests, including, but not limited to, black cutworm (BCW, *Agrotis ipsilon*), fall armyworm (FAW, *Spodoptera frugiperda*), tobacco budworm (TBW, *Heliothis virescens*), and corn earworm (CEW, *Helicoverpa zea*), but has no activity against the European corn borer (ECB, *Ostrinia nubilalis*). Thus, the Vip3A protein displays a unique spectrum of insecticidal activities. More recently, plants expressing the Vip3A protein have been found to be resistant to feeding damage caused by hemipteran insect pests (U.S. Pat. No. 6,429,360). Additional members of the Vip3 class of proteins have been identified (see, e.g., WO03/075655, WO02/078437, WO 98/18932, WO 98/33991, WO 98/00546, and WO 99/57282).

Numerous commercially valuable plants, including common agricultural crops, are susceptible to attack by insect pests, causing substantial reductions in crop yield and quality. For example, growers of maize (*Zea mays*), face a major problem with combating pest infestations. Insects, including Lepidopteran and Coleopteran insects, annually destroy an estimated 15% of agricultural crops in the United States and an even greater percentage in developing countries. In addition, competition with weeds and parasitic and saprophytic plants account for even more potential yield losses. Yearly, such pests cause over $100 billion in crop damage in the United States alone.

In an effort to combat pest infestations, various methods have been employed in order to reduce or eliminate pests in a particular plot. These efforts include rotating corn with other crops that are not a host for a particular pest and applying pesticides to the above-ground portion of the crop, applying pesticides to the soil in and around the root systems of the affected crop. Traditionally, farmers have relied heavily on chemical pesticides to combat pest damage.

There is a demand for alternative insecticidal agents for agricultural crops. For example, maize plants incorporating transgenic genes which cause the maize plant to produce insecticidal proteins providing protection against target pest(s) is another approach to controlling pests. Therefore, there remains a need to discover new and effective pest control agents that provide an economic benefit to farmers. Particularly needed are control agents that are targeted to a wider spectrum of economically important insect pests and that have a high specific activity against insect pests that are or could become resistant to existing insect control agents.

SUMMARY OF THE INVENTION

In some embodiments, a modified Vip3 polypeptide comprising a heterologous carbohydrate binding module (CBM) is provided. In some aspects, the heterologous CBM is substituted for all or a portion of Domain III of a Vip3 polypeptide. In some embodiments, the modified Vip3 polypeptide comprises all or a portion of Domain I and/or Domain II of a Vip3 polypeptide. In some embodiments, the modified Vip3 polypeptide comprises all or a portion of Domain IV of a Vip3 polypeptide or alternatively, lacks all or a portion of Domain IV of a Vip3 polypeptide. In some embodiments, the modified Vip3 polypeptide is pesticidal against, for example, insects, such as, for example, a fall armyworm. In some embodiments, a modified Vip3 polypeptide as described herein demonstrates insecticidal activity against a Vip3 resistant fall armyworm colony, such as, for example, a Vip3A resistant fall armyworm colony.

In another aspect, a composition is provided, the composition comprising a modified Vip3 polypeptide of the invention in an agriculturally acceptable carrier.

In some embodiments, the invention provides nucleic acid molecules and/or nucleotide sequences encoding modified Vip3 polypeptides of the invention and expression cassettes and recombinant vector comprising a nucleic acid molecule and/or nucleotide sequences encoding modified Vip3 polypeptides of the invention.

In further aspects, an extract from a transgenic seed or a transgenic plant of the invention is provided, wherein the extract comprises a nucleic acid molecule and/or a modified Vip3 polypeptide of the invention. Thus, in some embodiments, a composition comprising said extract is provided. In a further embodiment, the composition may comprise said extract in an agriculturally acceptable carrier.

In some embodiments, a method of providing a farmer with a means of controlling a plant pest is provided, the method comprising supplying to the farmer plant material or bacteria, said plant material or bacteria comprising a nucleic acid molecule that encodes the modified Vip3 polypeptide according to the invention.

In some aspects, a method of producing a modified Vip3 polypeptide of the invention is provided, comprising the steps of: (a) transforming a host cell with a recombinant nucleic acid molecule comprising a nucleotide sequence encoding for the modified Vip3 polypeptide; and (b) culturing the host cell of step (a) under conditions in which the host cell expresses the recombinant nucleic acid molecule, thereby producing the modified Vip3 polypeptide. In some embodiments, a method of producing a modified Vip3 polypeptide is provided, the method comprising, transforming a host cell with a nucleic acid molecule comprising a promoter operably linked to a nucleotide sequence encoding the modified Vip3 polypeptide of the invention; growing the host cell under conditions which allow expression of the modified Vip3 polypeptide; and recovering the modified Vip3 polypeptide. In some embodiments, a method of producing a modified Vip3 polypeptide is provided, the method comprising, growing a host cell of the invention under conditions which allow expression of the modified Vip3 polypeptide; and recovering the modified Vip3 polypeptide.

In some embodiments, a method of reducing damage in a transgenic plant caused by a plant pest is provided, the method comprising planting a transgenic plant seed comprising a nucleic acid molecule that expresses the modified Vip3 polypeptide of the invention, thereby reducing damage caused by the pest to a transgenic plant grown from the transgenic plant seed.

In some embodiments, the invention provides a method of controlling a pest comprising providing the transgenic plant of the invention and applying to the plant or the seed a crop protection product. In some embodiments, the pest is a fall armyworm.

In some embodiments, a method of controlling pests is provided, the method comprising contacting the pests with a pesticidally effective amount of the composition of the invention. In some embodiments, a method of protecting a plant and/or a plant propagation material is provided, the method comprising contacting the plant and/or plant propagation material with an effective amount of the composition of the invention. In some embodiments, the method comprises a method of controlling a fall armyworm colony.

In further aspects, a method of increasing pesticidal activity in a plant, plant part or plant cell is provided, the method comprising introducing one or more nucleic acid molecules encoding one or more modified Vip3 polypeptides of the invention into a plant, plant part or plant cell to produce a transgenic plant, plant part or plant cell that expresses the one or more nucleic acid molecules, wherein the one or more nucleic acid molecules encode for a polypeptide comprising pesticidal activity, thereby increasing pesticidal activity in the transgenic plant, plant part or plant cell as compared with a control.

In some embodiments, a modified Vip3 polypeptide and/or composition as described herein is active and/or insecticidal against a Vip3 resistant fall armyworm colony, such as, for example, a Vip3A resistant fall armyworm colony.

In some embodiments, transgenic host cells, including bacterial and plant cells, plants, and plant parts, including seeds, comprising a nucleic acid molecule and/or nucleotide sequences encoding modified Vip3 polypeptides of the invention are provided, as well as crops, and harvested and processed products produced therefrom.

These and other aspects of the invention are set forth in more detail in the description of the invention below.

BRIEF DESCRIPTION OF THE DRAWINGS

FIG. 3 shows a sequence alignment of three domain swaps (CenC—SEQ ID NO:30, GP21—SEQ ID NO:29, PsHGF7—SEQ ID NO:31) that were made based on amino acid sequence similarity to 2ZEX. The sequences share 84% consensus and 8% identity.

FIG. 5A-5C show schematics of the CBM substitutions in Vip3. FIG. 5A shows a portion of the Vip3D P021 (SEQ ID NO:6) sequence with amino acid residue 541 and 668 marked, as well as the exchange of Vip3D P021 amino acid residues 542 to 667 with the 2ZEX CBM (SEQ ID NO:24) and the 2ZEZ CBM (SEQ ID NO:25); FIG. 5B shows the exchange of Vip3D P021 (SEQ ID NO:6) amino acid residues 542 to 667 with the 1OFE CBM (SEQ ID NO:26), the 1PMH CBM (SEQ ID NO:27) and the 2BGP CBM (SEQ ID NO:28); FIG. 5C shows the exchange of the Vip3D P021 (SEQ ID NO:6) amino acid residues 542 to 667 with the GP21 CBM (SEQ ID NO:29), the CENC CBM (SEQ ID NO:30), the PsHGF7 CBM (SEQ ID NO:31) or the 1WKY CBM (SEQ ID NO:32).

BRIEF DESCRIPTION OF SEQUENCES IN THE SEQUENCE LISTING

Figure 1:
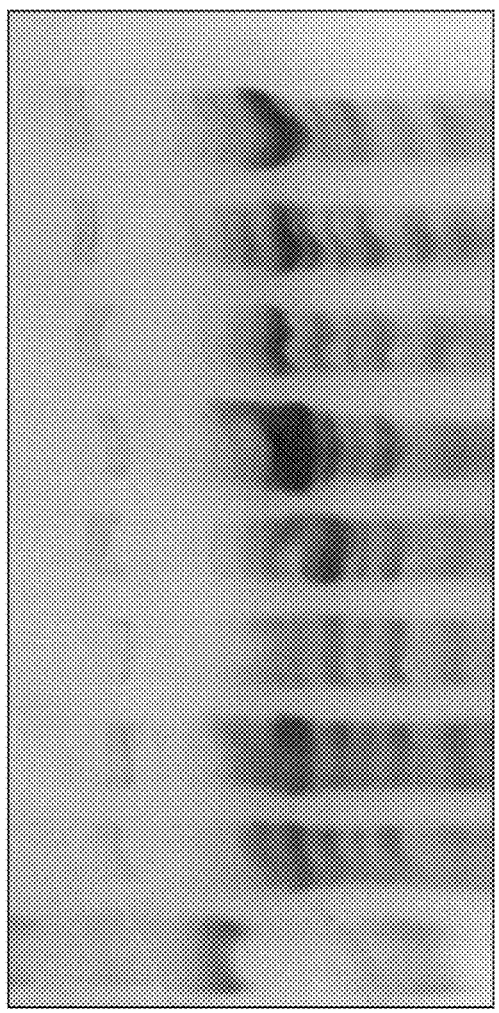
FIG. 1 shows a polyacrylamide gel electrophoresis (PAGE) gel of the soluble fraction of lysed *E. coli* expressing various Vip3D Domain III CBM swaps. The samples assayed are in Table 1 are, from left to right: molecular weight ladder, 1OF3, 1PMH, 1WKY, 2BGP, 2ZEZ, CenC, gp21, PsHGF7.

SEQ ID NO:1 is the amino acid sequence of Vip3D.
SEQ ID NO:2 is the amino acid sequence of Vip3A.
SEQ ID NO:3 is the amino acid sequence of Vip3B.
SEQ ID NO:4 is the amino acid sequence of Vip3C.
SEQ ID NO:5 is a consensus amino acid sequence of Vip3.
SEQ ID NO:6 is the amino acid sequence of P021 (10His-Vip3D-AAPF).
SEQ ID NO:7 is the amino acid sequence of P021 with Domain III swap to 2ZEX.
SEQ ID NO:8 is the amino acid sequence of P021 with Domain III swap to 2ZEZ.
SEQ ID NO:9 is the amino acid sequence of P021 with Domain III swap to 1OFE.
SEQ ID NO:10 is the amino acid sequence of P021 with Domain III swap to 1PMH.
SEQ ID NO:11 is the amino acid sequence of P021 with Domain III swap to 2BGP.
SEQ ID NO:12 is the amino acid sequence of P021 with Domain III swap to GP21.
SEQ ID NO:13 is the amino acid sequence of P021 with Domain III swap to CenC.
SEQ ID NO:14 is the amino acid sequence of P021 with Domain III swap to PSHGF7.
SEQ ID NO:15 is the amino acid sequence of P021 with Domain III swap to 1WKY.
SEQ ID NO:16 is the amino acid sequence of Vip3A with Domain III swap to 2ZEX.
SEQ ID NO:17 is the amino acid sequence of Vip3A with Domain III swap to 2ZEZ.
SEQ ID NO:18 is the amino acid sequence of Vip3A with Domain III swap to 1OFE.
SEQ ID NO:19 is the amino acid sequence of Vip3A with Domain III swap to 1PMH.
SEQ ID NO:20 is the amino acid sequence of Vip3A with Domain III swap to 2BGP.
SEQ ID NO:21 is the amino acid sequence of Vip3A with Domain III swap to gp21.
SEQ ID NO:22 is the amino acid sequence of Vip3A with Domain III swap to CenC.
SEQ ID NO:23 is the amino acid sequence of Vip3A with Domain III swap to PsHGF7.
SEQ ID NO:24 is the amino acid sequence of the 2ZEX domain.
SEQ ID NO:25 is the amino acid sequence of the 2ZEZ domain.
SEQ ID NO:26 is the amino acid sequence of the 1OFE domain.
SEQ ID NO:27 is the amino acid sequence of the 1PMH domain.
SEQ ID NO:28 is the amino acid sequence of the 2BGP domain.
SEQ ID NO:29 is the amino acid sequence of the gp21 domain.
SEQ ID NO:30 is the amino acid sequence of the CenC domain.
SEQ ID NO:31 is the amino acid sequence of the PsHGF7 domain.
SEQ ID NO:32 is the amino acid sequence of the 1WKY domain
SEQ ID NO:33 is the amino acid sequence of Vip3D with Domain III swap to 2ZEX.
SEQ ID NO:34 is the amino acid sequence of Vip3D with Domain III swap to 2ZEZ.
SEQ ID NO:35 is the amino acid sequence of Vip3D with Domain III swap to 1OFE.
SEQ ID NO:36 is the amino acid sequence of Vip3D with Domain III swap to 1PMH.
SEQ ID NO:37 is the amino acid sequence of Vip3D with Domain III swap to 2BGP.
SEQ ID NO:38 is the amino acid sequence of Vip3D with Domain III swap to GP21.
SEQ ID NO:39 is the amino acid sequence of Vip3D with Domain III swap to CenC.
SEQ ID NO:40 is the amino acid sequence of Vip3D with Domain III swap to PSHGF7.
SEQ ID NO:41 is the amino acid sequence of Vip3B with Domain III swap to 2ZEX.
SEQ ID NO:42 is the amino acid sequence of Vip3B with Domain III swap to 2ZEZ.
SEQ ID NO:43 is the amino acid sequence of Vip3B with Domain III swap to 1OFE.
SEQ ID NO:44 is the amino acid sequence of Vip3B with Domain III swap to 1PMH.
SEQ ID NO:45 is the amino acid sequence of Vip3B with Domain III swap to 2BGP.
SEQ ID NO:46 is the amino acid sequence of Vip3B with Domain III swap to GP21.
SEQ ID NO:47 is the amino acid sequence of Vip3B with Domain III swap to CenC.
SEQ ID NO:48 is the amino acid sequence of Vip3B with Domain III swap to PSHGF7.
SEQ ID NO:49 is the amino acid sequence of Vip3C with Domain III swap to 2ZEX.
SEQ ID NO:50 is the amino acid sequence of Vip3C with Domain III swap to 2ZEZ.
SEQ ID NO:51 is the amino acid sequence of Vip3C with Domain III swap to 1OFE.
SEQ ID NO:52 is the amino acid sequence of Vip3C with Domain III swap to 1PMH.
SEQ ID NO:53 is the amino acid sequence of Vip3C with Domain III swap to 2BGP.
SEQ ID NO:54 is the amino acid sequence of Vip3C with Domain III swap to GP21.
SEQ ID NO:55 is the amino acid sequence of Vip3C with Domain III swap to CenC.
SEQ ID NO:56 is the amino acid sequence of Vip3C with Domain III swap to PSHGF7.

DETAILED DESCRIPTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into some embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention.

Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein May be used in any combination. Moreover, the present invention also contemplates that in some embodiments of the invention, any feature or combination of features set forth herein may be excluded or omitted. To illustrate, if the specification states that a composition comprises components A, B and C, it is specifically intended that any of A, B or C, or a combination thereof, may be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, "chimeric" refers to a nucleic acid molecule or a polypeptide in which at least two components are derived from different sources (e.g., different organisms, different coding regions).

"Complement" as used herein can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, "contact", contacting", "contacted," and grammatical variations thereof, refer to placing the components of a desired reaction together under conditions suitable for carrying out the desired reaction (e.g., integration, transformation, site-specific cleavage (nicking, cleaving), amplifying, site specific targeting of a polypeptide of interest and the like). The methods and conditions for carrying out such reactions are well known in the art (See, e.g., Gasiunas et al. (2012) *Proc. Natl. Acad. Sci.* 109:E2579-E2586; M. R. Green and J. Sambrook (2012) Molecular Cloning: A Laboratory Manual. 4th Ed., Cold Spring Harbor Laboratory Press, Cold Spring Harbor, N.Y.).

To "control" an organism (e.g., insect pest) means to inhibit, through a toxic effect, the ability of an organism (e.g., insect pest) to survive, grow, feed, and/or reproduce, or to limit damage or loss in crop plants that is related to the activity of the organism. To "control" an organism may or may not mean killing the organism, although it preferably means killing the organism.

"Pesticidally effective amount," "effective pest controlling amount," or "effective insect-controlling amount" means that concentration or amount of a polypeptide that inhibits, through a toxic effect, the ability of pests or insects, respectively, to survive, grow, feed and/or reproduce, or to limit pest- or insect-related damage or loss in crop plants. "Pesticidally effective amount," "effective pest controlling amount," or "effective insect-controlling amount" may or may not mean killing the pests or insects, respectively, although it preferably means killing the pests or insects.

As used herein "pesticidal," or "insecticidal," and the like, refer to the ability of a modified Vip3 polypeptide to control a pest organism or an amount of a modified Vip3 polypeptide that may control a pest organism as defined herein. Thus, a pesticidal modified Vip3 polypeptide may kill or inhibit the ability of a pest organism (e.g., insect pest) to survive, grow, feed, and/or reproduce. In some embodiments, a modified Vip3 polypeptide of the invention may be pesticidal or insecticidal.

A "fragment" or "portion" of a nucleotide sequence or an amino acid sequence of the invention will be understood to mean a nucleotide or an amino acid sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid, nucleotide sequence, or an amino acid sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid, nucleotide sequence, or amino acid sequence. Such a fragment or portion according to the invention may be, where appropriate, included in a larger polynucleotide or polypeptide of which it is a constituent.

Thus, for example, fragments of Vip3 polypeptides may be used to carry out some embodiments of the present invention. In some embodiments, the term "Vip3 polypeptide" refers to full length as well as portions or fragments of Vip3 polypeptides. In general, such fragments are at least 20 or 30 contiguous amino acid residues in length. In some embodiments, a fragment of a Vip3 polypeptide may be at least about 20, 30, 40, 50, 60, 70, 80, 90, 100, 125, 150, 175, 200, 225, 250, 275, 300, 325, 350, 375, 400, 425, 450, 475, 500, 525, 550, 575 or more contiguous amino acid residues in length. In some embodiments, a fragment of a Vip3 polypeptide may be less than about 20, 30, 40, 50, 60, 70, 80, 90, 100, 125, 150, 175, 200, 225, 250, 275, 300, 325, 350, 375, 400, 425, 450, 475, 500, 525, 550, 575 or more contiguous amino acid residues in length. The fragment may comprise at least one, two, three or four of Vip3 polypeptide Domain I, Domain II, Domain III, and/or Domain IV, optionally with 1, 2, 3, 5, 7, 10, 12, 20, 30, 40, 50, 100 or more additional contiguous N-terminal and/or C-terminal amino acid residues. A Vip3 fragment may comprise all or a portion of Domain I, II, III, or IV. The length of the fragment (i.e., the number of contiguous amino acid residues) may be about 10%, 20%, 25%, 30%, 35%, 40%, 45%, 50%, 55%, 60%, 65%, 70%, 75%, 80%, 85%, 90%, 95% or more of the full-length Vip3 polypeptide. The fragment may comprise, consist essentially of and/or consist of an amino acid sequence of contiguous amino acids identical or almost identical (e.g., 90%, 91%, 92%, 93%, 94%, 95%, 96%, 97%, 98%, 99% identical) to a corresponding portion of the Vip3 polypeptide. In some embodiments, the modified Vip3 polypeptide may comprise at least two fragments of a Vip3 polypeptide. In some embodiments, the modified Vip3 polypeptide may comprise a first fragment of a Vip3 polypeptide and a second fragment, wherein said first fragment may comprise about 100 amino acid residues to about 600 amino acid residues, and any value or range therein, and said second fragment may comprise about 100 to about 300 amino acid residues, and any value or range therein.

In some embodiments, fragments of carbohydrate binding modules (CBMs) may be used to carry out some embodiments of the present invention. In some embodiments, the term "carbohydrate binding module" (CBM) refers to full length CBMs as well as portions or fragments of CBMs. In general, such fragments are at least 50 contiguous amino acid residues in length. In some embodiments, a fragment of a CBM may be at least about 50, 60, 70, 80, 90, 100, 125, 150, 175, 200, 225, 250, 275, 300, or more contiguous amino acid residues in length. In some embodiments, a fragment of a CBM polypeptide may be less than about 50, 60, 70, 80, 90, 100, 125, 150, 175, 200, 225, 250, 275, 300, 325, 350, 375, 400, 425, 450, 475, 500, 525, 550, 575 or more contiguous amino acid residues in length. The fragment may optionally comprise 1, 2, 3, 5, 7, 10, 12, 20, 30, 40, 50, 100 or more additional contiguous N-terminal and/or C-terminal amino acid residues. The length of the fragment (i.e., the number of contiguous amino acid residues) may be about 10%, 20%, 25%, 30%, 35%, 40%, 45%, 50%, 55%, 60%, 65%, 70%, 75%, 80%, 85%, 90%, 95% or more of the full-length CBM. The fragment may comprise, consist essentially of and/or consist of an amino acid sequence of contiguous amino acids identical or almost identical (e.g., 90%, 91%, 92%, 93%, 94%, 95%, 96%, 97%, 98%, 99% identical) to a CBM from a carbohydrate active enzyme.

Optionally, the CBM fragment comprises the metal binding domain (and/or any other known functional domain).

In some embodiments, the CBM fragment may comprise, consist essentially of, or consist of a CBM having an N and/or C terminal truncation. In some embodiments, the CBM may comprise a C-terminal truncation of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 amino acid residues, and the like, or any range or variable therein. In some embodiments, the CBM may comprise an N-terminal truncation of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 amino acid residues, and the like, or any range or variable therein. In some embodiments, a CBM useful with this invention can be truncation at both its N-terminal end and C-terminal end.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes may include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

A "heterologous" or a "recombinant" nucleotide sequence is a nucleotide sequence not naturally associated with a host cell into which it is introduced, including non-naturally occurring multiple copies of a naturally occurring nucleotide sequence and nucleotide sequences that are introduced into a host cell in a form that is not naturally occurring (e.g., operably linked to regulatory sequence(s) that do not naturally occur with that nucleotide sequence).

Different nucleic acids or proteins having homology are referred to herein as "homologues." The term homologue includes homologous sequences from the same and different species and orthologous sequences from the same and different species. "Homology" refers to the level of similarity or identity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention may comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention. Thus, for example, a homologue of a CBM useful with this invention may be at least about 70% homologous or more to any one of the CBM sequences provided herein, wherein the CBM sequence homologue has the function of binding carbohydrate(s). In some embodiments, the CBM sequence homologue has the function of binding cellulose and/or glucomannan. In some embodiments, the CBM sequence homologue has the function of binding internally on glycan chains. In some embodiments, a homologue of a Vip3 polypeptide useful with this invention may be about 70% homologous or more to any one of the Vip3 polypeptide sequences provided herein, wherein the homologue has pesticidal activity.

Thus, a homologue of a Vip3 polypeptide includes, but is not limited to: (1) polypeptides which are at least about 70% to at least about 90% (e.g., 70%, 71%, 72%, 73%, 74%, 75%, 76%, 77%, 78%, 79%, 80%, 81%, 82%, 83%, 84%, 85%, 86%, 87%, 88%, 89%, 90% 91%, 92%, 93%, 94%, 95%, 96%, 97%, 98%, 99%, 100%) identical at the sequence level to a member of the Vip3 class of polypeptides while also retaining pesticidal activity; (2) polypeptides which are cross-reactive to antibodies which immunologically recognize a member of the Vip3 class of polypeptides, (3) polypeptides which are cross-reactive with a receptor to a member of the Vip3 class of polypeptides and retain pesticidal activity, and (4) polypeptides, which are at least about 70% to at least about 90% (e.g., 70%, 71%, 72%, 73%, 74%, 75%, 76%, 77%, 78%, 79%, 80%, 81%, 82%, 83%, 84%, 85%, 86%, 87%, 88%, 89%, 90% 91%, 92%, 93%, 94%, 95%, 96%, 97%, 98%, 99%, 100%) identical at the sequence level to the toxic core region of a member of the Vip3 class of polypeptides, while also retaining pesticidal activity. Vip3 homologues have been disclosed in WO 98/18932, WO 98/33991, WO 98/00546, and WO 99/57282. An alignment of Vip3A and Vip3D polypeptides is provided in FIG. 1 and shows the substantial similarity in secondary structure.

Thus, in some embodiments of the invention, the polypeptides are at least 70% identical at the sequence level to a member of the Vip3 class of polypeptides and/or to the toxic core region of a member of the Vip3 class of polypeptides, while also retaining pesticidal activity. In some embodiments of the invention, the polypeptides are at least 80% identical at the sequence level to a member of the Vip3 class of polypeptides and/or to the toxic core region of a member of the Vip3 class of polypeptides, while also retaining pesticidal activity. In some embodiments, the polypeptides are at least 90% identical at the sequence level to a member of the Vip3 class of polypeptides and/or to the toxic core region of a member of the Vip3 class of polypeptides, while also retaining pesticidal activity.

As used herein, hybridization, hybridize, hybridizing, and grammatical variations thereof, refer to the binding of two fully complementary nucleotide sequences or substantially complementary sequences in which some mismatched base pairs are present. The conditions for hybridization are well known in the art and vary based on the length of the nucleotide sequences and the degree of complementarity between the nucleotide sequences. In some embodiments, the conditions of hybridization can be high stringency, or they can be medium stringency or low stringency depending on the amount of complementarity and the length of the sequences to be hybridized. The conditions that constitute low, medium and high stringency for purposes of hybridization between nucleotide sequences are well known in the art (See, e.g., Gasiunas et al. (2012) *Proc. Natl. Acad. Sci.* 109:E2579-E2586; M. R. Green and J. Sambrook (2012) Molecular Cloning: A Laboratory Manual. 4th Ed., Cold Spring Harbor Laboratory Press, Cold Spring Harbor, N.Y.).

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

A "native," or "wild type" nucleic acid, nucleotide sequence, polypeptide or amino acid sequence refers to a naturally occurring nucleic acid, nucleotide sequence, polypeptide or amino acid sequence. Thus, for example, a "wild type Vip3" is a Vip3 that is naturally occurring in or endogenous to the organism.

In contrast, a "heterologous" nucleic acid or polypeptide is a nucleic acid or polypeptide that is not naturally associated with a host cell into which it is introduced or is introduced in a form that is not naturally found in the cell into which it is being introduced.

Also as used herein, the terms "nucleic acid," "nucleic acid molecule," "nucleic acid construct," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The nucleic acid constructs of the present disclosure can be DNA or RNA, but are preferably DNA. Thus, although the nucleic acid constructs of this invention may be described and used in the form of DNA, depending on the intended use, they may also be described and used in the form of RNA.

A "synthetic" nucleic acid or nucleotide sequence, as used herein, refers to a nucleic acid or nucleotide sequence that is not found in nature but is constructed by the hand of man and as a consequence is not a product of nature.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. Except as otherwise indicated, nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end. Thus, for example, an element in the 3' region of a polynucleotide can be located anywhere from the first nucleotide located at the 3' end of the polynucleotide to the nucleotide located halfway through the polynucleotide.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

The terms "modify," "modifying" and/or "modification" (and grammatical variants thereof) as used herein with regard to Vip3 polypeptides and the polynucleotides encoding the Vip3 polypeptides refers to changing the wild-type or reference Vip3 polypeptide and its corresponding nucleotide sequence to include a heterologous carbohydrate binding module. In some embodiments, the toxicity of the modified Vip3 polypeptide produced is changed relative to the toxicity of the wild type or reference Vip3 polypeptide. A "change in toxicity" includes, but is not limited to, an increase and/or decrease in toxicity as it pertains to any particular target organism and/or a change in the organism(s) that are targeted (e.g., that the modified Vip3 polypeptide is now pesticidal against one or more additional organism(s) as compared to the wild-type or reference Vip3 polypeptide), including a change in maximum activity, a change in $LC_{50}$, and/or a change in the time to achieve toxicity.

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% and the like, or any value or range therein, as compared to a control. In some embodiments, a reduction may result in no or essentially no (i.e., an insignificant amount, e.g., less than about 10% or even 5%) detectable activity or amount. Thus, in some embodiments, a transgenic plant comprising a nucleic acid molecule that expresses the modified Vip3 polypeptide may reduce damage caused by a plant pest by at least about 5%, 10%, 15%, 20%, 25%, 35%, 50%, 75%, 80%, 85%, 90%, 95%, 97%, 98%, 99%, or 100%, and the like, or any value or range therein, as compared to a control (e.g., a plant that does not comprise said nucleic acid molecule that expresses the modified Vip3 polypeptide).

As used herein, "regulatory sequence(s)" means nucleotide sequence(s) located upstream (5' non-coding sequences), within or downstream (3' non-coding sequences) of a coding sequence, which influence the transcription, RNA processing or stability, or translation of the associated coding sequence. Regulatory sequences include, but are not limited to, promoters, enhancers, exons, introns, translation leader sequences, termination signals, and polyadenylation signal sequences. Regulatory sequences include natural and synthetic sequences as well as sequences that can be a combination of synthetic and natural sequences. An "enhancer" is a nucleotide sequence that can stimulate promoter activity and can be an innate element of the promoter or a heterologous element inserted to enhance the level or tissue specificity of a promoter. The primary sequence can be present on either strand of a double-stranded DNA molecule, and is capable of functioning even when placed either upstream or downstream from the promoter. The meaning of the term "promoter" can include "promoter regulatory sequences."

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection. In some embodiments of the invention, the substantial identity exists over a region of the sequences that is at least about 50 residues to about 750 residues in length. Thus, in some embodiments, substantial identity exists over a region of the sequences that is at least about 50 residues to about 250 residues in length, about 75 residues to about 225 residues in length, about 100 residues to about 200 residues in length, about 125 residues to about 175 residues in length, about 200 residues to about 400 residues in length, about 300 residues to about 450 residues in length, about 400 residues to about 500 residues in length, about 500 residues to about 550 residues in length, about 550 residues to about 650 residues in length, and/or about 650 residues to about 750 residues in length, or any value or range therein.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity or identity between two sequences (see, e.g., Karlin & Altschul, *Proc. Nat'l. Acad. Sci. USA* 90: 5873-5787 (1993)). One measure of similarity or identity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences may also be considered to be substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the invention. In one embodiment, a reference nucleotide sequence hybridizes to the "test" nucleotide sequence in 7% sodium dodecyl sulfate (SDS), 0.5 M NaPO$_4$, 1 mM EDTA at 50° C. with washing in 2×SSC, 0.1% SDS at 50° C. In some embodiments, the reference nucleotide sequence hybridizes to the "test" nucleotide sequence in 7% sodium dodecyl sulfate (SDS), 0.5 M NaPO$_4$, 1 mM EDTA at 50° C. with washing in 1×SSC, 0.1% SDS at 50° C. or in 7% sodium dodecyl sulfate (SDS), 0.5 M NaPO$_4$, 1 mM EDTA at 50° C. with washing in 0.5×SSC, 0.1% SDS at 50° C. In some embodiments, the reference nucleotide sequence hybridizes to the "test" nucleotide sequence in 7% sodium dodecyl sulfate (SDS), 0.5 M NaPO$_4$, 1 mM EDTA at 50° C. with washing in 0.1×SSC, 0.1% SDS at 50° C., or in 7% sodium dodecyl sulfate (SDS), 0.5 M NaPO$_4$, 1 mM EDTA at 50° C. with washing in 0.1×SSC, 0.1% SDS at 65° C.

Any nucleotide sequence and/or recombinant nucleic acid molecule of this invention may be codon optimized for expression in any species of interest. Codon optimization is well known in the art and involves modification of a nucleotide sequence for codon usage bias using species specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications of the nucleotide sequences are determined by comparing the species specific codon usage table with the codons present in the native polynucleotide sequences. As is understood in the art, codon optimization of a nucleotide sequence results in a nucleotide sequence having less than 100% identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the native nucleotide sequence but which still encodes a polypeptide having the same function as that encoded by the original, native nucleotide sequence. Thus, in some embodiments of the invention, the nucleotide sequence and/or recombinant nucleic acid molecule of this invention may be codon optimized for expression in the particular species of interest (e.g., a plant such as corn, soybean, sugar cane, sugar beet, rice or wheat).

In some embodiments, the recombinant nucleic acid molecules, nucleotide sequences and polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In some embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In some embodiments, an isolated nucleic acid molecule, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the recombinant nucleic acid molecules, nucleotide sequences and their encoded polypeptides are "isolated" in that, by the hand of man, they exist apart from their native environment and therefore are not products of nature, however, in some embodiments, they can be introduced into and exist in a recombinant host cell.

In any of the embodiments described herein, the nucleotide sequences and/or recombinant nucleic acid molecules of the invention can be operatively associated with a variety of promoters and other regulatory elements for expression in cells of various organisms. Thus, in some embodiments, a recombinant nucleic acid of this invention may further comprise one or more promoters operably linked to one or more nucleotide sequences.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences may be present between a promoter and a nucleotide sequence, and the promoter may still be considered "operably linked" to the nucleotide sequence.

A "promoter" is a nucleotide sequence that controls or regulates the transcription of a nucleotide sequence (i.e., a coding sequence) that is operably associated with the promoter. Typically, a "promoter" refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227).

Any promoter useful for initiation of transcription in a cell of a plant or bacteria may be used in the expression cassettes of the present invention. Promoters may include, for example, constitutive, inducible, temporally regulated, developmentally regulated, chemically regulated, tissue-preferred and/or tissue-specific promoters for use in the preparation of recombinant nucleic acid molecules, i.e., "chimeric genes" or "chimeric polynucleotides." These various types of promoters are known in the art.

The choice of promoter will vary depending on the temporal and spatial requirements for expression, and also depending on the host cell (e.g., plant or bacteria) to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

Further, for example, expression of a heterologous polynucleotide encoding a modified Vip3 polypeptide of the invention may be in any plant, plant part, (e.g., in leaves, in stalks or stems, in ears, in inflorescences (e.g. spikes, panicles, cobs, etc.), in roots, seeds and/or seedlings, and the like), plant cells, or bacterial cells. For example, in the case of a multicellular organism such as a plant where expression in a specific tissue or organ is desired, a tissue-specific or tissue preferred promoter may be used (e.g., a root specific/preferred promoter). In contrast, where expression in response to a stimulus is desired a promoter inducible by stimuli or chemicals may be used. In some embodiments, protection against more than one type of insect pest may be sought, and thus expression in multiple tissues is desirable. Where continuous expression at a relatively constant level is desired throughout the cells or tissues of an organism a constitutive promoter may be chosen.

Thus, promoters useful with the invention include, but are not limited to, those that drive expression of a nucleotide sequence constitutively, those that drive expression when induced, and those that drive expression in a tissue- or developmentally-specific or—preferred manner. These various types of promoters are known in the art. Promoters can be identified in and isolated from the plant, yeast, or bacteria to be transformed and then inserted into the expression cassette to be used in transformation of the plant, yeast, or bacteria.

Non-limiting examples of a promoter include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. *Gene* 403:132-142 (2007)) and Pdca1 is induced by salt (Li et al. *Mol Biol. Rep.* 37:1143-1154 (2010)).

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *Arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters may be used for expression of a heterologous polynucleotide in a plant cell. Tissue specific or preferred expression patterns include, but are not limited to, green tissue specific or preferred, root specific or preferred, stem specific or preferred, and flower specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; and the cestrum yellow leaf curling virus promoter disclosed in WO 01/73087.

Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology*, 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Particularly useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts may be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters may be used. Thus, for example, chemical-regulated promoters may be used to modulate the expression of a gene in an organism through the application of an exogenous chemical regulator. Regulation of the expression of nucleotide sequences of the invention via promoters that are chemically regulated enables the polypeptides of the invention to be synthesized only when, for example, a crop of plants are treated with the inducing chemicals. Depending upon the objective, the promoter may be a chemical-inducible promoter, where application of a chemical induces gene expression, or a chemical-repressible promoter, where application of the chemical represses gene expression.

Chemical inducible promoters useful with plants are known in the art and include, but are not limited to, the maize Int-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid (e.g., the PR1a system), steroid-responsive promoters (see, e.g., the glucocorticoid-inducible promoter in Schena et al. (1991) *Proc. Natl. Acad. Sci. USA* 88, 10421-10425 and McNellis et al. (1998) *Plant J.* 14, 247-257) and tetracycline-inducible and tetracycline-repressible promoters (see, e.g., Gatz et al. (1991) *Mol. Gen. Genet.* 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters.

Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), and the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one may use any of the inducible promoters described in Gatz (1996) *Current Opinion Biotechnol.* 7:168-172 and Gatz (1997) *Annu. Rev. Plant Physiol. Plant Mol. Biol.* 48:89-108. Other chemically inducible promoters useful for directing the expression of the nucleotide sequences of this invention in plants are disclosed in U.S. Pat. No. 5,614,395 herein incorporated by reference in its entirety. Chemical induction of gene expression is also detailed in the published application EP 0 332 104 (to Ciba-Geigy) and U.S. Pat. No. 5,614,395. In some embodiments, a promoter for chemical induction may be the tobacco PR-1a promoter.

In some embodiments, promoters useful with algae include, but are not limited to, the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)), the promoter of the $\sigma^{70}$-type plastid rRNA gene (Prrn), the promoter of the psbA gene (encoding the photosystem-II reaction center protein D1) (PpsbA), the promoter of the psbD gene (encoding the photosystem-II reaction center protein D2) (PpsbD), the promoter of the psaA gene (encoding an apoprotein of photosystem I) (PpsaA), the promoter of the ATPase alpha subunit gene (PatpA), and promoter of the RuBisCo large subunit gene (PrbcL), and any combination thereof (See, e.g., De Cosa et al. *Nat. Biotechnol.* 19:71-74 (2001); Daniell et al. *BMC Biotechnol.* 9:33 (2009); Muto et al. *BMC Biotechnol.* 9:26 (2009); Surzycki et al. *Biologicals* 37:133-138 (2009)).

In some embodiments, promoters useful with bacteria and yeast include, but are not limited to, a constitutive promoter (e.g., 1pp (lipoprotein gene)) and/or an oxidative stress inducible promoter (e.g., a superoxide dismutase or a catalase promoter).

Thus, in some embodiments, a promoter useful with yeast may include, but is not limited to, a promoter from phosphoglycerate kinase (PGK), glyceraldehyde-3-phosphate dehydrogenase (GAP), triose phosphate isomerase (TP1), galactose-regulon (GAL1, GAL10), alcohol dehydrogenase (ADH1, ADH2), phosphatase (PHO5), copper-activated metallothionine (CUP1), MFα1, PGK/α2 operator, TPI/α2 operator, GAP/GAL, PGK/GAL, GAP/ADH2, GAP/PHO5, iso-1-cytochrome c/glucocorticoid response element (CYC/GRE), phosphoglycerate kinase/angrogen response element (PGK/ARE), transcription elongation factor EF-1α (TEF1), triose phosphate dehydrogenase (TDH3), phosphoglycerate kinase 1 (PGK1), pyruvate kinase 1 (PYK1), and/or hexose transporter (HXT7) (See, Romanos et al. *Yeast* 8:423-488 (1992); and Partow et al. *Yeast* 27:955-964 (2010)).

In some embodiments, a promoter useful with bacteria may include, but is not limited to, L-arabinose inducible (araBAD, $P_{BAD}$) promoter, any lac promoter, L-rhamnose inducible (rhaP$_{BAD}$) promoter, T7 RNA polymerase promoter, trc promoter, tac promoter, lambda phage promoter ($p_L$, $p_L$-9G-50), anydrotetracycline-inducible (tetA) promoter, trp, lpp, phoA, recA, proU, cst-1, cadA, nar, pp-lac, cspA, T7-lac operator, T3-lac operator, T4 gene 32, T5-lac operator, nprM-lac operator, Vhb, Protein A, corynebacterial-*E. coli* like promoters, thr, horn, diphtheria toxin promoter, sig A, sig B, nusG, SoxS, katb, α-amylase (Parry), Ptms, P43 (comprised of two overlapping RNA polymerase σ factor recognition sites, σA, σB), Ptms, P43, rplK-rplA, ferredoxin promoter, and/or xylose promoter. (See, K. Terpe *Appl. Microbiol, Biotechnol.* 72:211-222 (2006); Hannig et al. *Trends in Biotechnology* 16:54-60 (1998); and Srivastava et al., *Protein Expr Purif* 40:221-229 (2005)).

As used herein, "expression cassette" means a recombinant nucleic acid molecule comprising a nucleotide sequence encoding a modified Vip3 polypeptide of the invention, wherein said nucleotide sequence is operably associated with at least a control sequence (e.g., a promoter). Thus, some aspects of the invention provide expression cassettes designed to express the nucleotides sequences encoding the modified Vip3 polypeptides of the invention.

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression.

In addition to the promoters operatively linked to the nucleotide sequences of the invention, an expression cassette of this invention also may include other regulatory sequences. Thus, an expression cassette also may optionally include a transcriptional and/or translational termination region (i.e., termination region) that is functional in the selected host cell. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the host cell, or may be derived from another source (i.e., foreign or heterologous to the promoter, to the nucleotide sequence of interest, to the host, or any combination thereof). Appropriate transcriptional terminators are those that are known to function in the host cell of interest. For plants, such terminators may include but are not limited to the CAMV 35S terminator, the tml terminator, the nopaline synthase terminator, and the pea rbcs E9 terminator.

Numerous nucleotide sequences have been found to enhance gene expression from within the transcriptional unit and these sequences may be used in conjunction with the expression cassettes of this invention to increase the expression of a polynucleotide of interest in a host cell.

Various intron sequences have been shown to enhance expression, particularly in monocotyledonous cells. For example, intron sequences are routinely incorporated into plant transformation vectors, typically within the non-translated leader.

A number of non-translated leader sequences derived from viruses are also known to enhance expression, and these are encompassed herein. Specifically, leader sequences from Tobacco Mosaic Virus (TMV, the "Ω-sequence"), Maize Chlorotic Mottle Virus (MCMV), and Alfalfa Mosaic Virus (AMV) have been shown to be effective in enhancing expression (see, for example, Gallie et al. (1987) *Nucleic Acids Res.* 15:8693-8711; Skuzeski et al. (1990) *Plant Molec. Biol.* 15:65-79). Other leader sequences known in the art include, but are not limited to, picomavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Allison et al. (1986) *Virology* 154:9-20; and Gallie et al. (1995) *Gene* 165:233-238); MDMV leader (Maize Dwarf Mosaic Virus; Allison et al. (1986) *Virology* 154:9-20); human immunoglobulin heavy-chain binding protein (BiP) leader (Macejak and Samow (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV; Gallie et al. (1987) *Nucleic Acids Res.* 15:3257-3273; Gallie et al. (1988) *Nucleic Acids Res.* 16:883-893; Gallie et al. (1992) *Nucleic Acids Res.* 20:4631-4638); and Maize Chlorotic Mottle Virus leader (MCMV; Lommel et al. (1991) *Virology* 81:382-385). See also, Della-Cioppa et al. (1987) *Plant Physiology* 84:965-968.

An expression cassette also may include a nucleotide sequence for a selectable marker, which may be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that may be selected for by chemical means, such as by using a selective agent (e.g., an antibiotic and the like), or on whether the marker is simply a trait that one can identify through observation or testing, such as by screening (e.g., fluorescence). Of course, many examples of suitable selectable markers are known in the art and may be used in the expression cassettes described herein.

In addition to expression cassettes, the nucleic acid molecules and nucleotide sequences described herein may be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Vectors for use in transformation of host organisms are well known in the art. Non-limiting examples of general classes of vectors include but are not limited to a viral vector, a plasmid vector, a phage vector, a phagemid vector, a cosmid vector, a fosmid vector, an artificial chromosome, or an *Agrobacterium* binary vector in double or single stranded linear or circular form which may or may not be self transmissible or mobilizable. A vector as defined herein may transform prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g., higher plants, mammals, fungi, including yeast) organisms. In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell. Accordingly, the nucleic acid molecules of this invention and/or expression cassettes may be comprised in vectors as described herein and as known in the art.

In some embodiments, it may be desirable to target the modified Vip3 polypeptides of the invention to particular parts of a cell such as the chloroplast, the cell wall, the mitochondria, and the like. A nucleotide sequence encoding a signal peptide may be operably linked at the 5'- or 3'-terminus of a heterologous nucleotide sequence or nucleic acid molecule.

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins, which is cleaved during chloroplast import to yield the mature protein (see, e.g., Comai et al. (1988) *J. Biol. Chem.* 263:15104-15109). These signal sequences may be fused to heterologous gene products to effect the import of heterologous products into the chloroplast (van den Broeck et al. (1985) *Nature* 313: 358-363). DNA encoding for appropriate signal sequences may be isolated from the 5' end of the cDNAs encoding the RUBISCO protein, the CAB protein, the EPSP synthase enzyme, the GS2 protein and many other proteins that are known to be chloroplast localized. See also, the section entitled "Expression with Chloroplast Targeting" in Example 37 of U.S. Pat. No. 5,639,949.

The above-described targeting sequences may be utilized not only in conjunction with their endogenous promoters, but also in conjunction with heterologous promoters. Use of promoters that are heterologous to the targeting sequence not only provides the ability to target the sequence but also can provide an expression pattern that is different from that of the promoter from which the targeting signal is originally derived.

Thus, signal peptides (and the targeting nucleotide sequences encoding them) are well known in the art and can be found in public databases such as the "Signal Peptide Website: An Information Platform for Signal Sequences and Signal Peptides."; the "Signal Peptide Database" (Choo et al., BMC Bioinformatics 6:249 (2005); ChloroP predicts the presence of chloroplast transit peptides (cTP) in protein sequences and the location of potential cTP cleavage sites); LipoP predicts lipoproteins and signal peptides in Gram negative bacteria); MITOPROT predicts mitochondrial targeting sequences); PlasMit; predicts mitochondrial transit peptides in *Plasmodium falciparum*); Predotar predicts mitochondrial and plastid targeting sequences); PTS1 (predicts peroxisomal targeting signal 1 containing proteins); SignalP (predicts the presence and location of signal peptide cleavage sites in amino acid sequences from different organisms: Gram-positive prokaryotes, Gram-negative prokaryotes, and eukaryotes).

Thus, for example, to localize to a plastid a transit peptide from plastidic Ferredoxin: NADP+ oxidoreductase (FNR) of spinach, which is disclosed in Jansen et al. (1988) *Current Genetics* 13:517-522, may be employed. In particular, the sequence ranging from the nucleotides −171 to 165 of the cDNA sequence disclosed therein may be used, which comprises the 5' non-translated region as well as the sequence encoding the transit peptide. Another example of a transit peptide is that of the waxy protein of maize including the first 34 amino acid residues of the mature waxy protein (Klosgen et al. (1989) *Mol. Gen. Genet.* 217:155-161). It is also possible to use this transit peptide without the first 34 amino acids of the mature protein. Furthermore, the signal peptides of the ribulose bisposphate carboxylase small subunit (Wolter et al. (1988) *Proc. Natl. Acad. Sci. USA* 85:846-850; Nawrath et al. (1994) *Proc. Natl. Acad. Sci. USA* 91:12760-12764), of NADP malate dehydrogenase (Galiardo et al. (1995) *Planta* 197:324-332), of glutathione reductase (Creissen et al. (1995) *Plant J.* 8:167-175) and/or of the R1 protein (Lorberth et al. (1998) *Nature Biotechnology* 16:473-477) may be used.

"Introducing," "introduce," "introduced" (and grammatical variations thereof) in the context of a polynucleotide of interest means presenting the nucleotide sequence of interest to the host organism or cell of said organism (e.g., host cell) in such a manner that the nucleotide sequence gains access to the interior of a cell. Where more than one nucleotide sequence is to be introduced these nucleotide sequences may be assembled as part of a single polynucleotide or nucleic acid construct, or as separate polynucleotide or nucleic acid constructs, and may be located on the same or different expression constructs or transformation vectors. Accordingly, these polynucleotides may be introduced into cells in a single transformation event, in separate transformation/transfection events, or, for example, they may be incorporated into an organism by conventional breeding protocols (e.g., crosses). Thus, in some aspects of the present invention one or more nucleic acid constructs of this invention (e.g., a nucleic acid molecule comprising a nucleotide sequence encoding a modified Vip3 polypeptide of the invention) may be introduced into a host organism or a cell of said host organism.

The term "transformation" or "transfection" as used herein refers to the introduction of a heterologous nucleic acid into a cell. Transformation of a cell may be stable or transient. Thus, in some embodiments, a host cell or host organism is stably transformed with a nucleic acid molecule of the invention. In some embodiments, a host cell or host organism is transiently transformed with a recombinant nucleic acid molecule of the invention.

"Transient transformation" in the context of a polynucleotide means that a polynucleotide is introduced into the cell and does not integrate into the genome of the cell.

"Stable transformation" or "stably transformed" as used herein means that a nucleic acid molecule is introduced (e.g., "stably introducing" or "stably introduced") into a cell and integrates into the genome of the cell. As such, the integrated nucleic acid molecule is capable of being inherited by the progeny thereof, more particularly, by the progeny of multiple successive generations. "Genome" as used herein also includes the nuclear and the plastid genome, and therefore includes integration of the nucleic acid into, for example, the chloroplast or mitochondrial genome. Stable transformation as used herein may also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell may be detected by, for example, a Southern blot hybridization assay of genomic DNA of the cell with nucleic acid sequences which specifically hybridize with a nucleotide sequence of a transgene introduced into an organism (e.g., a plant, a mammal, an insect, an archaea, a bacterium, and the like). Stable transformation of a cell may be detected by, for example, a Northern blot hybridization assay of RNA of the cell with nucleic acid sequences which specifically hybridize with a nucleotide sequence of a transgene introduced into a plant or other organism. Stable transformation of a cell may also be detected by, e.g., a polymerase chain reaction (PCR) or other amplification reactions as are well known in the art, employing specific primer sequences that hybridize with target sequence(s) of a transgene, resulting in amplification of the transgene sequence, which may be detected according to standard methods Transformation may also be detected by direct sequencing and/or hybridization protocols well known in the art.

Accordingly, in some embodiments, the nucleic acid molecule, nucleotide sequences, constructs, expression cassettes may be expressed transiently and/or they may be stably incorporated into the genome of the host organism.

A recombinant nucleic acid molecule/polynucleotide of the invention may be introduced into a cell by any method known to those of skill in the art. In some embodiments of the invention, transformation of a cell comprises nuclear transformation. In some embodiments, transformation of a cell comprises plastid transformation (e.g., chloroplast transformation). In some embodiments, the recombinant nucleic acid molecule/polynucleotide of the invention may be introduced into a cell via conventional breeding techniques (e.g., crossing).

Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013))

A nucleotide sequence therefore may be introduced into a host organism or its cell in any number of ways that are well known in the art. The methods of the invention do not depend on a particular method for introducing one or more nucleotide sequences into the organism, only that they gain access to the interior of at least one cell of the organism. Where more than one nucleotide sequence is to be introduced, they may be assembled as part of a single nucleic acid construct, or as separate nucleic acid constructs, and may be located on the same or different nucleic acid constructs. Accordingly, the nucleotide sequences may be introduced into the cell of interest in a single transformation event, or in separate transformation events, or, alternatively, where relevant, a nucleotide sequence may be incorporated into a plant, as part of a breeding protocol.

In some embodiments, a nucleic acid construct, a nucleic acid molecule, and/or a nucleotide sequence of this invention may be introduced into a cell of a host organism. Any cell/host organism for which this invention is useful with may be used. Exemplary host organisms include a plant, a bacterium, an archaeon, a virus, an animal (e.g., an insect), and/or a fungus (e.g., a yeast).

As used herein, "plant" means any plant and thus includes, for example, angiosperms including both monocots and dicots, gymnosperms, bryophytes, ferns and/or fern allies. In some embodiments of this invention, the plant is a seed plant. Further, a "plant" of this invention is any plant at any stage of development.

As used herein, the term "plant part" or "plant material" includes but is not limited to embryos, pollen, ovules, seeds, leaves, stems, roots, flowers or flower parts, branches, fruit, kernels, ears, cobs, husks, stalks, roots, root tips, anthers, pollen, egg cells, zygotes, cuttings, plant cells including plant cells that are intact in plants and/or parts of plants, plant protoplasts, plant tissues, plant cell tissue cultures, plant calli, plant clumps, or any other part or product of a plant. Further, as used herein, "plant cell" refers to a structural and physiological unit of the plant comprising a protoplast and a cell wall. Thus, in some embodiments, a plant cell of the invention may be in the form of an isolated single cell or may be a cultured cell or may be a part of a higher-organized unit such as, for example, a plant tissue or a plant organ.

A "protoplast" is an isolated plant cell without a cell wall or with only parts of the cell wall.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

The present invention is directed to modified vegetative insecticidal proteins (Vip), compositions comprising the same and methods of use thereof. In some embodiments, the Vip polypeptide is Vip3 polypeptide.

Vip3 polypeptides and nucleic acids encoding the same are known and described in, for example, J. Estruch et al., Proc. Natl. Acad. Sci. USA 93, 5389-5394 (May 1996); J. Liu et al., Letters in Applied Microbiology 45, 432-438 (2007); G. Warren, U.S. Pat. No. 5,990,383; Z. Shen et al., U.S. Pat. No. 7,378,493; P. Miles et al., U.S. Pat. Nos. 7,244,820; 5,877,012; 6,107,279, 6,137,033, and 6,291,156, the disclosures of all of which are incorporated by reference herein in their entirety. The naming of Vip proteins by the research groups discovering the respective proteins has varied. However, a standardized nomenclature has recently been developed and can be found at the *Bacillus thuringiensis* Toxin Nomenclature database. The present disclosure specifically exemplifies modifications to a Vip3A, Vip3B, Vip3C and Vip3D polypeptides, but the present invention may be practiced with any Vip polypeptide (e.g., any Vip3 polypeptide) now known or later discovered.

Accordingly, a "Vip3 polypeptide" in the context of the invention means any vegetative insecticidal protein (VIP) now or later identified that is a member of the Vip3 class including, for example, without limitation, Vip3A, Vip3B, Vip3C, Vip3D, and their homologues. In some embodiments, a Vip3 polypeptide useful with this invention can be a mutant Vip3 that is naturally occurring or non-naturally occurring. Some structural features that identify a protein as being in the Vip3 class of proteins includes, 1) a size of about 80-88 kDa that is proteolytically processed by insects or trypsin to about a 62-66 kDa toxic core (Lee et al. 2003. Appl. Environ. Microbiol. 69:4648-4657); and 2) a highly conserved N-terminal secretion signal which is not naturally processed during secretion in *B. thuringiensis*. Non-limiting examples of members of the Vip3 class including those previously mentioned and their respective GenBank accession numbers, U.S. Patent or patent publication number are Vip3Aa1 (AAC37036), Vip3Aa2 (AAC37037), Vip3Aa3 (U.S. Pat. No. 6,137,033), Vip3Aa4 (AAR81079), Vip3Aa5 (AAR81080), Vip3Aa6 (AAR81081), Vip3Aa7 (AAK95326), Vip3Aa8 (AAK97481), Vip3Aa9 (CAA76665), Vip3Aa10 (AAN60738), Vip3Aa11 (AAR36859), Vip3Aa12 (AAM22456), Vip3Aa13 (AAL69542), Vip3Aa14 (AAQ12340), Vip3Aa15 (AAP51131), Vip3Aa16 (AAW65132), Vip3Aa17 (U.S. Pat. No. 6,603,063), Vip3Aa18 (AAX49395), Vip3Aa19 (DQ241674), Vip3Aa19 (DQ539887), Vip3Aa20 (DQ539888), Vip3Aa21 (ABD84410), Vip3Aa22 (AAY41427), Vip3Aa23 (AAY41428), Vip3Aa24 (BI 880913), Vip3Aa25 (EF608501), Vip3Aa26 (EU294496), Vip3Aa27 (EU332167), Vip3Aa28 (FJ494817), Vip3Aa29 (FJ626674), Vip3Aa30 (FJ626675), Vip3Aa31 (FJ626676), Vip3Aa32 (FJ626677), Vip3Aa33 (GU073128), Vip3Aa34 (GU073129), Vip3Aa35 (GU733921), Vip3Aa36 (GU951510), Vip3Aa37 (HM132041), Vip3Aa38 (HM117632), Vip3Aa39 (HM117631), Vip3Aa40 (HM132042), Vip3Aa41 (HM132043), Vip3Aa42 (HQ587048), Vip3Aa43 (HQ594534), Vip3Aa44 (HQ650163), Vip3Ab1 (AAR40284), Vip3Ab2 (AAY88247), Vip3Ac1 (U.S. Patent Application Publication 20040128716), Vip3Ad1 (U.S. Patent Application Publication 20040128716), Vip3Ad2 (CAI43276), Vip3Ae1 (CAI43277), Vip3Af1 (U.S. Pat. No. 7,378,493), Vip3Af2 (ADN08753), Vip3Af3 (HM117634), Vip3Ag1 (ADN08758), Vip3Ag2 (FJ556803), Vip3Ag3 (HM117633), Vip3Ag4 (HQ414237), Vip3Ag5 (HQ542193), Vip3Ah1 (DQ832323), Vip3Ba1 (AAV70653), Vip3Ba2 (HM117635), Vip3Bb1 (U.S. Pat.

No. 7,378,493), Vip3Bb2 (AB030520), Vip3C (Palma et al. *Appl. Environ Microbiol* 78(19):7163-7165 (2012)) and/or Vip3Bb3 (ADI48120).

The present inventors have surprisingly discovered that modifying a Vip3 polypeptide such that it comprises a heterologous carbohydrate binding module (CBM) results in a modified Vip3 polypeptide having altered characteristics including altered toxicity toward plant pests as compared to the same Vip3 polypeptide that is not modified to comprise said heterologous CBM (i.e., a reference Vip3).

Accordingly, in one aspect of the invention a modified Vip3 polypeptide comprising, consisting essentially of, or consisting of a heterologous carbohydrate binding module (CBM) is provided. In some embodiments, a modified Vip 3 polypeptide can comprise, consist essentially of, or consist of two or more CBMs, which can be the same or different, optionally in tandem. In some embodiments, the heterologous CBM may be substituted for all or a portion of Domain III of a Vip3 polypeptide. In some embodiments, the modified Vip3 polypeptide comprises all or a portion of Domain I and/or Domain II of a Vip3 polypeptide. In some embodiments, the modified Vip3 polypeptide may comprise, consist essentially of, or consist of all or a portion of Domain IV of a Vip3 polypeptide and/or may lack all or a portion of Domain IV of a Vip3 polypeptide. In some embodiments, the modified Vip3 polypeptide comprises, consists essentially of, or consists of, in the amino terminal to carboxy terminal direction, all or a portion of Domain I of the Vip3 polypeptide, all or a portion of Domain II of the Vip3 polypeptide, the heterologous CBM, and optionally all or a portion of Domain IV of the Vip3 polypeptide.

In some embodiments, the modified Vip3 polypeptide of the invention comprises, consists essentially of, or consists of all or a portion of any one of SEQ ID NO:1, SEQ ID NO:2, SEQ ID NO:3, SEQ ID NO:4, or SEQ ID NO:6 or an amino acid sequence having at least 70% identity to said portion of SEQ ID NO:1, SEQ ID NO:2, SEQ ID NO:3, SEQ ID NO:4, or SEQ ID NO:6.

In some embodiments, Domain III of a Vip3 polypeptide comprises, consists essentially of, or consists of amino acids 518 to 684 of said Vip3 polypeptide. In particular embodiments, Domain III comprises, consists essentially of, or consists of amino acids 542 to 667 of SEQ ID NOs:1-3 or a corresponding amino acid sequence from a different Vip3 polypeptide, amino acids 550 to 675 of SEQ ID NO:4 or a corresponding amino acid sequence from a different Vip3 polypeptide, or amino acids 552 to 667 of SEQ ID NO:6 or a corresponding amino acid sequence from a different Vip3 polypeptide.

"Corresponding to" in the context of the present invention means that when the amino acid sequences of certain proteins are aligned with each other, the amino acids that "correspond to" certain enumerated positions in the present invention are those that align with these positions in a reference sequence, but that are not necessarily in these exact numerical positions relative to a particular amino acid sequence of the invention.

In some embodiments, Domain III of a Vip3 polypeptide comprises, consists essentially of, or consists of:
(a) amino acids 542 to 667 of SEQ ID NO:1;
(b) amino acids 542 to 667 of SEQ ID NO:2;
(c) amino acids 542 to 667 of SEQ ID NO:3;
(d) amino acids 550 to 675 of SEQ ID NO:4;
(e) amino acids 552 to 677 of SEQ ID NO:6;
(f) a corresponding amino acid sequence of another Vip3 polypeptide as described herein; or
(g) an amino acid sequence having at least about 70% identity to any one of (a) to (f), above.

The heterologous CBM may be incorporated into the Vip3 polypeptide, for example, by insertion or by substitution of a portion of the Vip3 polypeptide. In embodiments in which the CBM in substituted for a portion of a Vip3 polypeptide, the portion of the Vip3 polypeptide that is exchanged for a heterologous CBM may include all of Domain III, a portion of Domain III (e.g., fewer amino acid residues than the entirety of Domain III) or may be a portion of the Vip3 polypeptide that is greater than the entirety of Domain III (e.g., may extend in the N-terminal direction outside of Domain III and toward or into Domain II and/or in the C-terminal direction outside of Domain III and toward or into Domain IV). Thus, for example, when Domain III of a Vip3 polypeptide is swapped or exchanged for a heterologous CBM, one or more amino acid residues (e.g., 1, 2, 3, 4, 5, 6, 7, 8, 9, 10, 11, 12, 13, 14, 15, 16, 17, 18, 19, 20, or more residues) of the Vip3 polypeptide, at the amino terminal side and/or the carboxy terminal side of Domain III, also may be included in the exchange. Thus, for example, when Domain III comprises amino acids 542 to 667 of SEQ ID NO:1, the substitution may include one or more of amino acid residues 500 to 541 (e.g., amino acid 500, 501, 502, 503, 504, 505, 506, 507, 508, 509, 510, 511, 512, 513, 514, 515, 516, 517, 518, 519, 520, 522, 523, 524, 525, 526, 527, 528, 529, 530, 531, 532, 533, 534, 535, 536, 537, 538, 539, 540, 541 or any range therein) at the amino terminal side and/or one or more of amino acids 668 to 700 (e.g., amino acid 668, 669, 670, 671, 672, 673, 674, 675, 676, 678, 679, 680, 681, 682, 683, 684, 685, 686, 687, 688, 689, 690, 691, 692, 693, 694, 695, 696, 697, 698, 699, 700 or any range therein) at the carboxy terminal side of said Domain III, in any combination. In some embodiments, the substitution can comprise, consist essentially of, or consist of portion of Domain III that is about one to about four (e.g., 1, 2, 3, or 4) amino acid residues shorter than the full Domain III at the C-terminal end and/or the N-terminal end. In some embodiments, the substitution can comprise, consist essentially of, or consist of Domain III and an additional one to about ten (e.g., 1, 2, 3, 4, 5, 6, 7, 8, 9, or 10) amino acid residues more than the full Domain III at the C-terminal end and/or the N-terminal end.

In some embodiments, at least a portion of a Vip3 Domain III as described herein may be exchanged for a CBM. Thus, for example, when Domain III is amino acids 550 to 675 of SEQ ID NO:4, the substitution may include fewer than all of the amino acids residues 550 to 675 by retaining in the Vip3 polypeptide one or more of the amino acid residues (e.g., 1, 2, 3, 4, 5, 6, 7, 8, 9, 10, 11, 12, 13, 14, 15, 16, 17, 18, 19, 20, or more residues, and the like) at the amino terminal side and/or the carboxy terminal side of Domain III of SEQ ID NO:4 (e.g., amino acid residues 550 to 675). As an example, for SEQ ID NO:4, the portion of Domain III that is exchanged may be the full length amino acid sequence of residues 550 to 675, or it may be, for example, residues 551 to 675, 552 to 675, 553 to 675, 554 to 675, 551 to 674, 551 to 673, 551 to 672, 550 to 673, 555 to 670, 560 to 675, 560 to 670, and so on.

Thus, the region of the Vip3 polypeptide that is exchanged for the heterologous CBM may be any combination of all of Domain III, or more and/or fewer amino acid residues at the carboxy terminus and/or the amino terminus of Domain III of the Vip3 polypeptide.

In some embodiments, a modified Vip3 polypeptide of the invention has at least about 70% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%) amino acid sequence similarity or identity with an amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, or SEQ ID NO:56 (i.e., SEQ ID NOs:1-23 or SEQ ID NOs:33-56). In some embodiments, a modified Vip3 polypeptide of the invention has at least about 75% amino acid sequence similarity or identity with an amino acid sequence selected from any one of SEQ ID NOs:1-23 or SEQ ID NOs:33-56. In some embodiments, a modified Vip3 polypeptide of the invention has at least about 80% amino acid sequence similarity or identity with an amino acid sequence selected from any one of SEQ ID NOs:1-23 or SEQ ID NOs:33-56. In some embodiments, a modified Vip3 polypeptide of the invention has at least about 85% amino acid sequence similarity or identity with an amino acid sequence selected from any one of SEQ ID NOs:1-23 or SEQ ID NOs:33-56. In some embodiments, a modified Vip3 polypeptide of the invention has at least about 90% amino acid sequence similarity or identity with an amino acid sequence selected from any one of SEQ ID NOs:1-23 or SEQ ID NOs:33-56. In some embodiments, a modified Vip3 polypeptide of the invention has at least about 95% amino acid sequence similarity or identity with an amino acid sequence selected from any one of SEQ ID NOs:1-23 or SEQ ID NOs:33-56. In some embodiments, a modified Vip3 polypeptide of the invention has at least about 90 to about 100% amino acid sequence similarity or identity with an amino acid sequence selected from any one of SEQ ID NOs:1-23 or SEQ ID NOs:33-56. In some embodiments, a modified Vip3 polypeptide of the invention has 100% amino acid sequence similarity or identity with an amino acid sequence selected from any one of SEQ ID NOs:1-23 or SEQ ID NOs:33-56.

In representative embodiments, a modified Vip3 polypeptide of the invention may be an "improved Vip3 polypeptide" when compared to its wild-type or reference parent Vip3 polypeptide, in that it displays one or more of the following characteristics: 1) an increased potency against a target insect (higher specific activity) and/or an increased kill rate (faster kill at comparable level of protein); 2) increased or decreased target pest spectrum; 3) decreased susceptibility to development of resistance by target pests; 4) increased expression levels in a transgenic host or host cell; 5) increased resistance to insect protease degradation (increased stability in the target insect gut); 6) increased stability in the environment; and 7) reduced toxicity to beneficial insects, non-target pests, and plants.

Therefore, in the context of the invention, "improves pesticidal (e.g., insecticidal, nematicidal) activity" or "improved pesticidal (e.g., insecticidal) activity," or any grammatical variation thereof, means that a modification of the Vip3 polypeptide results in an engineered polypeptide of the invention having one or more of the following characteristics: 1) an increased potency against a target pest (e.g., insect) (i.e., higher specific activity) and/or an increased kill rate (faster kill at comparable level of protein), 2) increased or decreased target pest spectrum, 3) decreased susceptibility to development of resistance by target pests, 4) increased expression levels in a transgenic host or host cell, 5) increased resistance to insect protease degradation (increased stability in the target insect gut), 6) increased stability in the environment and 7) reduced toxicity to beneficial insects, non-target pests, and plants.

Carbohydrate binding modules (CBMs) are discretely folded domains that are found within a protein that is a carbohydrate active enzyme. As their name indicates, CBMs are characterized by their carbohydrate binding activity (see, e.g., Boraston et al. *Biochem J.* 382:769-781) (2004)). CBMs are non-catalytic domains connected to catalytic modules in the larger polypeptide via linker sequences that are sometimes highly flexible (Gilbert et al. Curr. Op. Structural Biol. 23:669-677 (2013)). It is generally believed that CBMs function to bring the enzyme of which they are a part in closer proximity with the target substrate, thereby leading to an increase in the rate of catalysis.

Currently, carbohydrate-binding modules are classified into 67 families based on amino acid sequence similarities (see, Carbohydrate Active enZyme database; Cantarel et al. (2009). "The Carbohydrate-Active EnZymes database (CAZy): An expert resource for Glycogenomics". Nucleic Acids Research 37 (Database issue): D233-D238.

A heterologous CBM useful with this invention may be a Type B CBM from any protein. Type B CBMs are glycan chain binding CBMs having grooves or clefts. (Boraston et al. *Biochem J.* (382:769-781 (2004)). In some embodiments, a Type B CBM useful with this invention comprises a β-sandwich. In some embodiments, a heterologous CBM comprises, consists essentially of, or consists of a CBM amino acid sequence from a β-1,4-mannanase, optionally a Type B CBM amino acid sequence from a β-1,4-mannanase.

In some embodiments, a CBM useful with the invention is from a β-1,4-mannanase. The EC number provided by the International Union of Biochemistry and Molecular Biology (IUBMB) for this enzyme family is EC 3.2.1.78. Thus, in some embodiments, a CBM useful with this invention is an enzyme from the enzyme class EC 3.2.1.78. The accepted name for this class of enzymes is mannan endo-1,4-beta-mannosidase but these enzymes are also known by the names of β-1,4-mannanase, endo-1,4-mannanase, beta-mannanase; endo-1,4-β-mannanase, endo-β-1,4-mannase, β-mannanase B, β-1, 4-mannan 4-mannanohydrolase, endo-β-mannanase, β-D-mannanase, and/or 1,4-β-D-mannan mannanohydrolase.

In some embodiments, a modified Vip3 may comprise a functional portion of a heterologous CBM, such as a Type B CBM, or a Type B CBM from a 1,4-β mannanase. A functional portion of a CBM may include any amino acid residue that falls within approximately about 3 angstroms to about 8 angstroms (E.g., about 3, 4, 5, 6, 7, 8 angstroms and the like) of the carbohydrate binding site and/or influences the conformation of an amino acid which interacts with the carbohydrate. Amino acid residues that may influence the conformation of an amino acid that interacts with the carbohydrate may include those that may make a hydrogen bond, a van der Waals interaction, a hydrophobic interaction, or a charge change with the carbohydrate itself, water and/or an ion that directly interacts with the carbohydrate. Thus, in some embodiments, a heterologous CBM comprises, consists essentially of, or consists of all or a functional portion of a CBM amino acid sequence from a β-1,4-mannanase, optionally a Type B CBM amino acid sequence from a β-1,4-mannanase.

CBMs useful with this invention can be found, for example, in the Carbohydrate-Active enZYmes Database. Some non-limiting examples include CBMs from: Mannan endo-1,4-beta-mannosidase from Caldicellulosiruptor obsidiansis OB47 (GenBank Acc. No. ADL41540.1), Mannan endo-1,4-beta-mannosidase from *Paenibacillus mucilaginosus* 3016 (GenBank Acc. No. AFC29293.1), beta-1,4-mannanase from *Geobacillus stearothermophilus* (GenBank Acc. No. AAC71692.1), or beta-1,4-mannanase from *Vibrio* sp. MA-138 (GenBank Acc. No. BAG69482.2).

Additional non-limiting examples of beta-1,4-mannanase polypeptides from which the CBMs may be useful with this invention include a CBM from a beta-1,4-mannanase from: Caldicellulosiruptor saccharolyticus (GenBank Accession No. AAC44232.1), *Vibrio* sp. MA-138 (GenBank Accession No. BAG69482.2); *Cellulosimicrobium* sp. HY-13 (GenBank Accession No. AEE43708.1), *Bacillus subtilis* (GenBank Accession No. AEB98481.1), *Haliotis discus discus* (GenBank Accession No. BA199559.1), *Streptomyces* sp. s6-204 (GenBank Accession No. ABY90130.1), *Vibrio* sp. MA-138 (GenBank Accession No. BAA25188.1), *Klebsiella pneumoniae* subsp. *pneumoniae* KPNIH27 (GenBank Accession No. AIA43525.1), *Klebsiella oxytoca* (GenBank Accession No. AIE71926.1); *Aeromonas caviae* (GenBank Accession No. KEP91190.1), *Klebsiella pneumoniae* subsp. *pneumoniae* KPR0928 (GenBank Accession No. AIE29885.1); *Cronobacter pulveris* (NCBI Reference Sequence: WP_029591781.1), *Gemmobacter nectariphilus* (NCBI Reference Sequence: WP_028029945.1), *Thioalkalivibrio* sp. ALJ24 (NCBI Reference Sequence: WP 026287860.1); *Paracoccus* sp. N5 (NCBI Reference Sequence: WP 026155388.1); *Rhizobium* sp. JGI 0001002-C21 (NCBI Reference Sequence: WP 025570492.1); *Cronobacter sakazakii* (GenBank Accession No. KDP99185.1), *Enterobacter asburiae* (NCBI Reference Sequence: WP_024908493.1), *Yersinia enterocolitica* subsp. *enterocolitica* 8081 (NCBI Reference Sequence: YP_001008241.1); *Clostridium straminisolvens* JCM 21531 (GenBank Accession No. GAE87707.1), or *Vibrio furnissii* NCTC 11218 (GenBank: ADT88758.1). Other non-limiting examples of beta-1,4-mannanase polypeptides may be found at the Carbohydrate Active enZYmes (CAZY) database.

In some embodiments, a heterologous CBM comprises, consists essentially of, or consists of a CBM amino acid sequence that has at least about 70%-100% (e.g., at least about 70%, 75%, 80%, 85%, 90%, 95%, 96%, 97%, 98%, 99%, 100%, or any variable or range therein) amino acid sequence similarity or identity with the amino acid sequence of a naturally occurring CBM, for example, a Type B CBM from a β 1,4-mannanase (e.g., any one of SEQ ID NOs:24-32). In some embodiments, the heterologous CBM comprises, consists essentially of, or consists of a CBM amino acid sequence that has at least about 75% amino acid sequence similarity or identity with the amino acid sequence of any one of SEQ ID NOs:24-32. In some embodiments, the heterologous CBM comprises, consists essentially of, or consists of a CBM amino acid sequence that has at least about 80% to about 95% amino acid sequence similarity or identity with the amino acid sequence of any one of SEQ ID NOs:24-32. In some embodiments, heterologous CBM comprises, consists essentially of, consists of a CBM amino acid sequence that has at least about 95% amino acid sequence similarity or identity (e.g., 95%, 96%, 97%, 98%, 99%, or more) with the amino acid sequence of any one of SEQ ID NOs:24-32.

In some embodiments, the heterologous CBM comprises a metal binding site. In some embodiments, the metal binding site of the heterologous CBM binds calcium and/or magnesium. A metal binding site on a CBM may be coordinated by charged atoms and may bind in and into loop motifs on a surface of the CBM and/or the protein that the CBM in present in. In some embodiments, the metal may be involved in the binding of a carbohydrate. In some embodiments, the metal may not be relevant to the binding of the carbohydrate function of the CBM in the protein in which the CBM is naturally located.

In some embodiments, the modified Vip3 polypeptide is pesticidal against, for example, insects. Accordingly, in some embodiments, the modified Vip3 polypeptide is pesticidal against an insect, for example, a lepidopteran insect.

Accordingly, in some embodiments, insect pests include without limitation insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, and the like. In some embodiments, insect pests include without limitation *Ostrinia nubilalis* (European corn borer), *Plutella xylostella* (diamondback moth), *Spodoptera frugiperda* (fall armyworm), *Agrotis ipsilon* (black cutworm), *Agrotis orthogonia* (pale western cutworm), *Striacosta albicosta* (western bean cutworm), *Helicoverpa zea* (corn earworm), *Heliothis virescens* (tobacco budworm), *Spodoptera exigua* (beet armyworm), *Helicoverpa punctigera* (native budworm), *Helicoverpa armigera* (cotton bollworm), *Manduca sexta* (tobacco hornworm), *Trichoplusia ni* (cabbage looper), *Pectinophora gossypiella* (pink bollworm), *Diatraea grandiosella* (southwestern corn borer), *Diatraea saccharalis* (sugarcane borer), *Elasmopalpus lignosellus* (lesser cornstalk borer), *Psuedoplusia includens* (soybean looper), *Anticarsia gemmatalis* (velvetbean caterpillar), *Plathypena scabra* (green cloverworm), *Homoeosoma electellum* (sunflower head moth), *Cochylis hospes* (banded sunflower moth), or any combination thereof.

In some embodiments, a composition comprising a modified Vip3 polypeptide is provided. In some embodiments, the composition comprising the modified Vip3 polypeptide may be prepared from an extract of a transgenic plant or plant part (e.g., seed), said transgenic plant or plant part comprising a nucleotide sequence encoding said modified Vip3 polypeptide. In some embodiments, the composition comprising the modified Vip3 polypeptide may be produced by expressing a polynucleotide encoding a polypeptide of the invention in bacterial cells capable of expressing the polynucleotide. In some embodiments, the composition comprises the modified Vip3 polypeptide in an agriculturally acceptable carrier.

As used herein an "agriculturally-acceptable carrier" may include natural or synthetic, organic or inorganic material, which may be combined with the active component to facilitate its application to the plant, or part thereof. An agriculturally-acceptable carrier includes, but is not limited to, inert components, dispersants, surfactants, adjuvants, tackifiers, stickers, binders, or combinations thereof, that may be used in agricultural formulations. Another agriculturally acceptable carrier may be a transgenic plant or plant part.

Such compositions may be applied in any manner that brings the pesticidal polypeptides in contact with the pests, resulting in toxic effect and control of the pest(s). Accordingly, the compositions may be applied to the surfaces of plants or plant parts, including seeds, leaves, flowers, stems, tubers, roots, and the like. Thus, the composition(s) of the modified Vip3 polypeptides may be delivered in many recognized ways, e.g., orally by ingestion by the pest or by contact with the pest via transgenic plant expression, formulated protein composition(s), sprayable protein composition(s), a bait matrix, or any other art-recognized toxin delivery system.

In some embodiments, the invention provides a nucleic acid molecule comprising, consisting essentially of, consisting of a nucleotide sequence encoding one or more than one of the modified Vip3 polypeptides described herein. In some embodiments, the nucleic acid molecule comprises, consists essentially of, or consists of one or more than one of the nucleotide sequence(s) of SEQ ID NOs:7-23 and/or SEQ ID NOs:33-56. In some embodiments, a nucleotide sequence encoding a modified Vip3 polypeptide may be codon optimized for expression in a particular host organism or host cell.

Thus, in some embodiments, a nucleic acid of this invention is expressed in transgenic plants. For expression in transgenic plants, the nucleotide sequences encoding the modified Vip3 polypeptides of the invention may require other modifications and/or optimization. Although in many cases, nucleotide sequences from microbial organisms can be expressed in plants at high levels without modification, low expression in transgenic plants may result from microbial nucleotide sequences having codons that are not preferred in plants. It is known in the art that all organisms have specific preferences for codon usage, and the codons of the nucleic acids/nucleotide sequences described herein can be changed to conform with plant preferences, while maintaining the amino acid sequence encoded thereby. Furthermore, high expression in plants is best achieved from coding sequences that have at least about 35% GC content, preferably more than about 45%, more preferably more than about 50%, and most preferably more than about 60%. Microbial nucleic acids that have low GC contents may express poorly in plants due to the existence of ATTTA motifs that may destabilize messages, and AATAAA motifs that may cause inappropriate polyadenylation. Although nucleotide sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleotide sequences can be screened for the existence of illegitimate splice sites that may cause message truncation. All changes required to be made within the nucleic acids/nucleotide sequences such as those described above are made using well known techniques of site directed mutagenesis, PCR, and synthetic gene construction (See, e.g., EP 0 385 962, EP 0 359 472, and WO 93/07278.

In some embodiments, the invention provides transgenic non-human host cells comprising the nucleic acid molecules of the invention. A non-human host cell can include, but is not limited to, a plant cell, a bacterial cell, a fungal (e.g., yeast) cell, or an insect cell. In some embodiments, the transgenic host cell is a transgenic plant cell or a transgenic bacterial cell. In some embodiments, the plant cell is a non-propagating cell.

In some embodiments, the invention provides a plant, plant part and/or plant cell comprising the nucleic acid molecules of the invention. Non-limiting examples of plants useful with this invention include vegetable crops, including artichokes, kohlrabi, arugula, leeks, asparagus, lettuce (e.g., head, leaf, romaine), bok choy, malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy) cardoni, carrots, napa, okra, onions, celery, parsley, chick peas, parsnips, chicory, peppers, potatoes, cucurbits (e.g., marrow, cucumber, zucchini, squash, pumpkin), radishes, dry bulb onions, rutabaga, eggplant (also called brinjal), salsify, escarole, shallots, endive, garlic, spinach, green onions, squash, greens, beet (sugar beet and fodder beet), sweet potatoes, swiss chard, horseradish, tomatoes, turnips, and spices; a fruit and/or vine crop such as apples, apricots, cherries, nectarines, peaches, pears, plums, prunes, cherry, quince, almonds, chestnuts, filberts, pecans, pistachios, walnuts, citrus, blueberries, boysenberries, cranberries, currants, loganberries, raspberries, strawberries, blackberries, grapes, avocados, bananas, kiwi, persimmons, pomegranate, pineapple, tropical fruits, pomes, melon, mango, papaya, and lychee; a field crop plant such as clover, alfalfa, evening primrose, meadow foam, corn/maize (field, sweet, popcorn), hops, jojoba, peanuts, rice, safflower, small grains (barley, oats, rye, wheat, etc.), sorghum, tobacco, kapok, a leguminous plant (beans, lentils, peas, soybeans), an oil plant (rape, mustard, poppy, olive, sunflower, coconut, castor oil plant, cocoa bean, groundnut), *Arabidopsis*, grasses (turf grasses, ornamental grasses), a fibre plant (cotton, flax, hemp, jute), lauraceae (cinnamon, camphor), or a plant such as coffee, sugar cane, tea, and natural rubber plants; and/or a bedding plant such as a flowering plant, a cactus, a succulent and/or an ornamental plant, as well as trees such as forest (broad-leaved trees and evergreens, such as conifers), fruit, ornamental, and nut-bearing trees, as well as shrubs and other nursery stock.

In particular embodiments, a plant, plant part or plant cell of this invention may be sorghum, wheat, sunflower, tomato, a cole crop, cotton, rice, soybean, sugar beet, sugar cane, tobacco, barley, oilseed rape and/or maize. In some embodiments, the plant is maize. In some embodiments, the plant is soybean.

In representative embodiments, a plant comprising the nucleic acid molecules of the invention and expressing the Vip3 polypeptide is maize and the Vip3 polypeptide produced by the plant is pestidical against an insect pest from the order Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, or any combination thereof. In some embodiments, a plant comprising the nucleic acid molecules of the invention and expressing the Vip3 polypeptide is maize and the Vip3 polypeptide produced by the plant is pestidical against an insect pest from the order Lepidoptera. In some embodiments, a plant comprising the nucleic acid molecules of the invention and expressing the Vip3 polypeptide is maize and the Vip3 polypeptide produced by the plant is pestidical against, for example, *Ostrinia nubilalis* (European corn borer), *Spodoptera frugiperda* (fall armyworm), *Agrotis ipsilon* (black cutworm), *Agrotis orthogonia* (pale western cutworm), *Striacosta albicosta* (western bean cutworm), *Helicoverpa zea* (corn earworm), *Spodoptera exigua* (beet armyworm), *Helicoverpa punctigera* (native budworm), *Helicoverpa armigera* (cotton bollworm), *Diatraea grandiosella* (southwestern corn borer), *Diatraea saccharalis* (sugarcane borer), *Elasmopalpus lignosellus* (lesser cornstalk borer), or any combination thereof. In some embodiments, a plant comprising the nucleic acid molecules of the invention and expressing the Vip3 polypeptide is maize and the Vip3 polypeptide produced by the plant is pestidical against *Ostrinia nubilalis* (European corn borer), *Spodoptera frugiperda* (fall armyworm), *Helicoverpa zea* (corn earworm), or *Agrotis ipsilon* (black cutworm) or any combination thereof.

In representative embodiments, a plant comprising the nucleic acid molecules of the invention and expressing the Vip3 polypeptide is soybean and the Vip3 polypeptide produced by the plant is pestidical against an insect pest from the order Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, or any combination thereof. In some embodiments, a plant comprising the nucleic acid molecules of the invention and expressing the Vip3 polypeptide is soybean and the Vip3 polypeptide produced by the plant is pestidical against an insect pest from the order Lepidoptera. In some embodiments, a plant comprising the nucleic acid molecules of the invention and expressing the Vip3 polypeptide is soybean and the Vip3 polypeptide produced by the plant is pestidical against, for example, *Spodoptera frugiperda* (fall armyworm), *Agrotis ipsilon* (black cutworm), *Agrotis* orthogonia (pale western cutworm), *Helicoverpa zea* (corn earworm), *Heliothis virescens* (tobacco budworm), *Spodoptera exigua* (beet armyworm), *Helicoverpa punctigera* (native budworm), *Helicoverpa armigera* (cotton bollworm), *Trichoplusia ni* (cabbage looper), *Elasmopalpus lignosellus* (lesser cornstalk borer), *Psuedoplusia includens* (soybean looper), *Anticarsia gemmatalis* (velvetbean caterpillar), *Plathypena scabra* (green cloverworm), *Homoeosoma electellum* (sunflower head moth), or *Cochylis hospes* (banded sunflower moth), or any combination thereof. In some embodiments, a plant comprising the nucleic acid molecules of the invention and expressing the Vip3 polypeptide is soybean and the Vip3 polypeptide produced by the plant is pestidical against *Ostrinia nubilalis* (European corn borer), *Spodoptera frugiperda* (fall armyworm), *Helicoverpa zea* (corn earworm), or *Agrotis ipsilon* (black cutworm) or any combination thereof.

In some embodiments, a virus, such as a baculovirus, may comprise a polynucleotide encoding a modified Vip3 polypeptide of this invention in its genome. Said recombinant viruses can express large amounts of the corresponding modified Vip3 polypeptide after infection of eukaryotic cells suitable for virus replication and expression of the polynucleotide. The pesticidal polypeptide thus produced can be used as a pesticidal or insecticidal agent. Alternatively, viruses (e.g., baculoviruses) engineered to include one or more polynucleotides of this invention can be used to infect insects in vivo and kill them either by expression of the pesticidal polypeptide or by a combination of viral infection and expression of the pesticidal polypeptide.

Bacterial cells can also be hosts for the expression of the nucleic acids of the invention. In one embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive nucleic acids for the same purpose.

Thus, in some embodiments, as biological pesticidal control agents, the pesticidal polypeptides of the invention may be produced by expression of the polynucleotides encoding the polypeptides of the invention in heterologous host cells capable of expressing the polynucleotides. Accordingly, in some embodiments, a yeast, bacterial or plant cell comprising one or more polynucleotides of the invention is provided.

Techniques for the transformation of the various organisms/host cells are known in the art. For example, the expression vectors pKK223-3 and pKK223-2 may be used to express heterologous genes in *E. coli*, either in transcriptional or translational fusion, behind a tac or trc promoter. For the expression of operons encoding multiple ORFs, one procedure is to insert the operon into a vector such as pKK223-3 in transcriptional fusion, allowing the cognate ribosome binding site of the heterologous genes to be used. Techniques for overexpression in gram-positive species such as *Bacillus* are also known in the art and may be used in the context of this invention (Quax et al. In: *Industrial Microorganisms: Basic and Applied Molecular Genetics*, Eds. Baltz et al., American Society for Microbiology, Washington (1993)). Alternate systems for overexpression rely, for example, on yeast vectors and include the use of *Pichia, Saccharomyces* and/or *Kluyveromyces* (Sreekrishna, In: *Industrial Microorganisms: Basic and Applied Molecular Genetics*, Baltz, Hegeman, and Skatrud eds., American Society for Microbiology, Washington (1993); Dequin & Barre, *Biotechnology* L2:173-177 (1994); van den Berg et al., *Biotechnology* 8:135-139 (1990)).

Procedures for transforming plants are well known and routine in the art and are described throughout the literature. Non-limiting examples of methods for transformation of plants include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

For *Agrobacterium*-mediated transformation, binary vectors or vectors carrying at least one T-DNA border sequence are suitable, whereas for direct gene transfer (e.g., particle bombardment and the like) any vector is suitable and linear DNA containing only the construction of interest may be used. In the case of direct gene transfer, transformation with a single DNA species or co-transformation may be used (Schocher et al., *Biotechnology* 4:1093-1096 (1986)). For both direct gene transfer and *Agrobacterium*-mediated transfer, transformation is usually (but not necessarily) undertaken with a selectable marker that may be a positive selection (Phosphomannose Isomerase), provide resistance to an antibiotic (kanamycin, hygromycin or methotrexate) or a herbicide (glyphosate or basta). However, the choice of selectable marker is not critical to the invention.

*Agrobacterium*-mediated transformation is a commonly used method for transforming plants, in particular, dicot plants, because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen & Willmitzer (1988) *Nucleic Acids Res.* 16:9877).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

As discussed previously, another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

In some embodiments, a polynucleotide of the invention may be directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) *Proc. Natl. Acad. Sci. USA* 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin can be utilized as selectable markers for transformation (Svab, Z., Hajdukiewicz, P., and Maliga, P. (1990) *Proc. Natl. Acad. Sci. USA* 87, 8526-8530; Staub, J. M., and Maliga, P. (1992) *Plant Cell* 4, 39-45). The presence of cloning sites between these markers allows creation of a plastid targeting vector for introduction of foreign genes (Staub, J. M., and Maliga, P. (1993) *EMBO J.* 12, 601-606).

Substantial increases in transformation frequency can be obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) *Proc. Natl. Acad. Sci. USA* 90, 913-917). Previously, this marker had been used successfully for high-frequency transformation of the plastid genome of the green alga *Chlamydomonas reinhardtii* (Goldschmidt-Clermont, M. (1991) *Nucl. Acids Res.* 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In one embodiment, a polynucleotide of the invention can be inserted into a plastid-targeting vector and transformed into the plastid genome of a desired plant host. Thus, plants homoplastic for plastid genomes containing a nucleotide sequence of the invention can be obtained, which are capable of high expression of the polynucleotide.

Methods of selecting for transformed, transgenic plants, plant cells and/or plant tissue culture are routine in the art and can be employed in the methods of the invention provided herein.

A polynucleotide therefore can be introduced into the plant, plant part and/or plant cell in any number of ways that are well known in the art, as described above. Therefore, no particular method for introducing one or more polynucleotides into a plant is relied upon, rather any method that allows the one or more polynucleotides to gain access to the interior of at least one cell of the plant may be used. Where more than one polynucleotides is to be introduced, the respective polynucleotides may be assembled as part of a single nucleic acid molecule, or as separate nucleic acid molecules, and may be located on the same or different nucleic acid molecules. Accordingly, the polynucleotides may be introduced into the cell of interest in a single transformation event, in separate transformation events, or, for example, in plants, as part of a breeding protocol.

In some embodiments of this invention, the introduced nucleic acid molecule may be maintained in the plant cell stably if it is incorporated into a non-chromosomal autonomous replicon or integrated into the plant chromosome(s). Alternatively, the introduced nucleic acid molecule may be present on an extra-chromosomal non-replicating vector and be transiently expressed or transiently active. Whether present in an extra-chromosomal non-replicating vector or a vector that is integrated into a chromosome, the nucleic acid molecule may be present in a plant expression cassette. A plant expression cassette may contain regulatory sequences that drive gene expression in plant cells that are operatively linked so that each sequence can fulfill its function, for example, termination of transcription by polyadenylation signals. Exemplary polyadenylation signals can be those originating from *Agrobacterium tumefaciens* T-DNA such as the gene known as octopine synthase of the Ti-plasmid pTiACH5 (Gielen et al. *EMBO J.* 3:835 (1984)) or functional equivalents thereof, but also all other terminators functionally active in plants are suitable. A plant expression cassette of this invention may also contain other operatively linked sequences like translational enhancers such as the overdrive-sequence containing the 5'-untranslated leader sequence from tobacco mosaic virus enhancing the polypeptide per RNA ratio (Gallie et al. *Nucl. Acids Research* 15:8693-8711 (1987)).

Further, as is well known in the art, intact transgenic plants may be regenerated from transformed plant cells, plant tissue culture and/or cultured protoplasts using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)).

Additionally, the genetic properties engineered into the transgenic seeds and plants, plant parts, and/or plant cells of the invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

Accordingly, the present invention provides transgenic plants, plant parts and plant cells and plants regenerated therefrom comprising a nucleic acid molecule comprising, consisting essentially of, or consisting of a nucleotide sequence encoding a modified Vip3 polypeptide of the invention. In some embodiments, the transgenic plant, plant part or plant cell is a selected from the group of plants consisting of sorghum, wheat, sunflower, tomato, cole crop, cotton, rice, soybean, sugar beet, sugar cane, tobacco, barley, oilseed rape and maize.

In some embodiments of the invention a harvested product produced from the transgenic cells, plants and/or plant parts of the invention may be provided, as well as a processed product produced from said harvested product. A harvested product may be a whole plant or any plant part, as described herein, wherein said harvested product comprises a nucleic acid molecule/nucleotide sequence or polypeptide of the invention. Thus, in some embodiments, a non-limiting example of a harvested product includes a seed, a fruit, a flower or part thereof (e.g., an anther, a stigma, and the like), a leaf, a stem, a stalk, a root, a tuber, and the like. In particular embodiments, the harvested product is a seed, wherein the seed comprised the nucleic acid molecule(s)/nucleotide sequence(s) and/or polypeptide(s) of the invention in its genome.

In some embodiments, a processed product includes, but is not limited to, a flour, meal, oil, starch, sugar, fiber, biofuel or cereal, and the like, or a product produced therefrom. In some embodiments the processed product is an extract from the seed, wherein the extract comprises a nucleic acid molecule, nucleotide sequence or polypeptide of the invention. In some embodiments, the processed product comprises a nucleic acid molecule/nucleotide sequence or polypeptide of the invention.

In some embodiments, the invention further provides a crop comprising a plurality of the plants of the invention planted together in an agricultural field. In some embodiments, the invention provides a crop comprising a plurality of the transgenic plants of the invention planted together in a golf course, a residential lawn, a road side, an athletic field, and/or a recreational field.

Also provided herein are methods of using the modified Vip3 polypeptides of the invention, and/or the nucleic acid molecules/polynucleotides encoding said modified Vip3 polypeptides.

Accordingly, in some embodiments, a method of producing a plant, plant part or plant cell with increased resistant or tolerance to one or more pests is provided, the method comprising introducing one or more nucleic acid molecules comprising one or more nucleotide sequences encoding one or more modified Vip3 polypeptides of the invention into a plant, plant part or plant cell to produce a transgenic plant, plant part or plant cell that expresses the one or more nucleic acid molecules, thereby expressing the one or more modified Vip3 polypeptides and increasing resistance or tolerance to one or more pests in said transgenic plant, plant part or plant cell as compared with a control plant, plant part or plant cell that does not comprise said one or more nucleic acid molecules. In some embodiments, the method comprises regenerating a transgenic plant from said transgenic plant cell or plant part, wherein the transgenic plant comprises in its genome the one or more nucleic acid molecules and has increased pesticidal activity.

In another aspect, a method of increasing pesticidal activity in a plant, plant part or plant cell is provided, the method comprising introducing one or more nucleic acid molecules comprising one or more nucleotide sequences encoding one or more modified Vip3 polypeptides of the invention into a plant, plant part or plant cell to produce a transgenic plant, plant part or plant cell that expresses the one or more nucleic acid molecules, thereby expressing (producing) the one or more modified Vip3 polypeptides and increasing pesticidal activity in the transgenic plant, plant part or plant cell as compared with a control plant, plant part or plant cell that does not comprise said one or more nucleic acid molecules. In some embodiments, the method comprises regenerating a transgenic plant from said transgenic plant cell or plant part, wherein the transgenic plant comprises in its genome the one or more nucleic acid molecules and has increased pesticidal activity.

In some embodiments, a method of providing a farmer with a means of controlling a plant pest is provided, the method comprising supplying to the farmer plant material or bacteria, said plant material or bacteria comprising a nucleic acid molecule that encodes the modified Vip3 polypeptide of the invention.

In some embodiments, a method of producing the modified Vip3 polypeptide of the invention is provided, the method comprising the steps of: (a) transforming a host cell with a recombinant nucleic acid molecule comprising a nucleotide sequence encoding for the modified Vip3 polypeptide; and (b) culturing the host cell of step (a) under conditions in which the host cell expresses the recombinant nucleic acid molecule, thereby producing the modified Vip3 polypeptide.

In some embodiments of the invention, a method of producing a modified Vip3 polypeptide is provided, the method comprising, growing a host cell of the invention under conditions which allow expression of the modified Vip3 polypeptide; and recovering the modified Vip3 polypeptide.

In some embodiments, a method of reducing damage in a transgenic plant caused by a plant pest, the method comprising planting a transgenic plant seed comprising a nucleic acid molecule that expresses the modified Vip3 polypeptide or the invention, thereby reducing damage caused by the pest to a transgenic plant grown from the transgenic plant seed. In some embodiments, the nucleic acid molecule(s) is/are comprised in an expression cassette or a recombinant vector.

In any of the embodiments described herein, the nucleic acid molecules of the invention may be comprised in one or more expression cassette(s) and/or vector(s), wherein said nucleic acid molecules may be in operable association with one or more promoters (and/or other regulatory elements) that function in the host cell (e.g., plant, bacteria, etc). In some embodiments, the one or more expression cassette(s) or vector(s) may comprise a selectable marker. In some embodiments, the one or more expression cassette(s) or vector(s) do not comprise a selectable marker.

In some embodiments, the invention provides a method of controlling pests comprising, contacting the pests with a pesticidally effective amount of a composition of the invention. In some embodiments of the invention, a method of protecting a plant and/or a plant propagation material is provided, the method comprising contacting the plant and/or plant propagation material with a pesticidally effective amount of a composition of the invention.

The modified Vip3 polypeptides of the invention may be used in combination with other pesticidal principles or crop protection products (i.e., pesticidal active ingredients) to increase pest target range. Thus, the modified Vip3 polypeptide may be used in combination with other pesticidal principles of a distinct nature for the prevention and/or management of insect resistance. Other insecticidal principles include, for example, protease inhibitors (both serine and cysteine types), lectins, alpha-amylase, peroxidase and cholesterol oxidase. Similarly, Cry proteins, such as the proteins in the CryIA, CryIB and CryIC families, are also useful in combination with the modified Vip3 proteins of the present invention.

The co-expression of more than one insecticidal principle in the same transgenic plant or plant part (e.g., seed) can be achieved by genetically engineering a plant to contain and express all the genes necessary. Alternatively, a plant, Parent 1, can be genetically engineered for the expression of genes of the present invention. A second plant, Parent 2, can be genetically engineered for the expression of a supplemental insect control principle. By crossing Parent 1 with Parent 2, progeny plants are obtained which express all the genes introduced into Parents 1 and 2.

Transgenic plants or plant parts or transgenic seed of the invention may also be treated with a pesticidal active ingredient/crop protection product. Where both the pesticidal active ingredient and the transgenic plant or plant part or transgenic seed of the invention are active against the same target insect, the combination is useful (i) in a method for enhancing activity of a modified Vip3 polypeptide of the invention against the target insect and (ii) in a method for preventing development of resistance to modified Vip3 polypeptide of the invention by providing a second mechanism of action against the target insect. Thus, the invention provides a method of enhancing activity against or preventing development of resistance in a target insect, comprising, for example, applying an insecticidal seed coating as described in U.S. Pat. Nos. 5,849,320 and 5,876,739, herein incorporated by reference to a transgenic seed comprising one or more modified Vip3 polypeptide of the invention.

Therefore in one embodiment, the invention encompasses a method of controlling crop pests by providing a transgenic plant, or transgenic plant part (e.g., transgenic seed) of the invention and applying to the transgenic plant, plant part or seed a pesticidal active ingredient/crop protection product. In doing so, the activity of a modified Vip3 polypeptide of the invention against a target insect is enhanced and (ii) in a method for preventing development of resistance to modified Vip3 polypeptide of the invention by providing a second mechanism of action against the target insect. Further, the application of a crop protection product to a transgenic plant or plant part may be done to increase the number of crop pests controlled by applying a crop protection that is effective against additional crop pests.

Such active ingredients that may be applied to a transgenic plant and/or a transgenic plant part (e.g., seed) of the invention as described above includes, without limitation, (1) Acetylcholine esterase (AChE) inhibitors, for example carbamates, for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC and xylylcarb; or organophosphates, for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-5-methyl, demeton-5-methylsulphone, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulphotep, sulprofos, tebupirimfos, temephos, terbufos, tetrachlorvinphos, thiometon, triazophos, trichlorfon, vamidothion, and imicyafos. (2) GABA-gated chloride channel antagonists, for example organochlorines, for example camphechlor, chlordane, endosulfan, gamma-HCH, HCH, heptachlor, lindane and methoxychlor; or fiproles (phenylpyrazoles), for example acetoprole, ethiprole, fipronil, pyrafluprole, pyriprole, vaniliprole. (3) Sodium-channel modulators/voltage-dependent sodium channel blockers, for example pyrethroids, for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrin (pyrethrum), eflusilanat; DDT; or methoxychlor. (4) Nicotinergic acetylcholine receptor agonists/antagonists, for example Chloronicotinyls, for example acetamiprid, clothianidin, dinotefuran, imidacloprid, imidaclothiz, nitenpyram, nithiazine, thiamethoxam, AKD-1022, nicotine, bensultap, cartap, thiosultap-sodium, and thiocylam. (5) Allosteric acetylcholine receptor modulators (agonists), for example spinosyns, for example spinosad and spinetoram. (6) Chloride channel activators, for example mectins/macrolides, for example abamectin, emamectin, emamectin benzoate, ivermectin, lepimectin, and milbemectin; or juvenile hormone analogues, for example hydroprene, kinoprene, methoprene, epofenonane, triprene, fenoxycarb, pyriproxifen, and diofenolan. (7) Active ingredients with unknown or nonspecific mechanisms of action, for example fumigants, for example methyl bromide, chloropicrin and sulphuryl fluoride; selective antifeedants, for example cryolite, pymetrozine, pyrifluquinazon and flonicamid; or mite growth inhibitors, for example clofentezine, hexythiazox, etoxazole. (8) Inhibitors of oxidative phosphorylation, ATP disruptors, for example diafenthiuron; organotin compounds, for example azocyclotin, cyhexatin and fenbutatin oxide; or propargite, tetradifon. (9) Oxidative phosphorylation decouplers which interrupt the H-proton gradient, for example chlorfenapyr, binapacyrl, dinobuton, dinocap and DNOC. (10) Microbial disruptors of the insect gut membrane, for example *Bacillus thuringiensis* strains. (11) Chitin biosynthesis inhibitors, for example benzoylureas, for example bistrifluoron, chlorfluazuron, diflubenzuron, fluazuron, flucycloxuron, flufenoxuron, hexaflumuron, lufenuron, novaluron, noviflumuron, penfluoron, teflubenzuron or triflumuron. (12) Buprofezin. (13) Moulting disruptors, for example cyromazine. (14) Ecdysone agonists/disruptors, for example diacylhydrazines, for example chromafenozide, halofenozide, methoxyfenozide, tebufenozide, and fufenozide (JS118); or azadirachtin. (15) Octopaminergic agonists, for example amitraz; (16) Site III electron transport inhibitors/site II electron transport inhibitors, for example hydramethylnon; acequinocyl; fluacrypyrim; or cyflumetofen and cyenopyrafen. (17) Electron transport inhibitors, for example site I electron transport inhibitors from the group of the METI acaricides, for example fenazaquin, fenpyroximate, pyrimidifen, pyridaben, tebufenpyrad, tolfenpyrad, and rotenone; or voltage-dependent sodium channel blockers, for example indoxacarb and metaflumizone. (18) Fatty acid biosynthesis inhibitors, for example tetronic acid derivatives, for example spirodiclofen and spiromesifen; or tetramic acid derivatives, for example spirotetramat. (19) Neuronal inhibitors with unknown mechanism of action, for example bifenazate. (20) Ryanodin receptor effectors, for example diamides, for example flubendiamide, (R)-, (S)-3-chloro-$N^1$-{2-methyl-[1,2,2,2-tetrafluoro-1-(trifluoromethyl)-ethyl]phenyl}-$N^2$-(1-methyl-2-methylsulphonylethyl)phthalamide, chlorantraniliprole (Rynaxypyr), or cyantraniliprole (Cyazypyr). (21) Further active ingredients with unknown mechanism of action, for example amidoflumet, benclothiaz, benzoximate, bromopropylate, buprofezin, chinomethionat, chlordimeform, chlorbenzilate, clothiazoben, cyclopriene, dicofol, dicyclanil, fenoxacrim, fentrifanil, flubenzimine, flufenerim, flutenzin, gossyplure, japonilure, metoxadiazone, petroleum, potassium oleate, pyridalyl, sulfluramid, tetrasul, triarathene, or verbutin; or the following known active compounds: 4-{[(6-bromopyrid-3-yl)methyl](2-fluoroethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-yl)methyl](2-fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), 4-{[(6-chloropyrid-3-yl)methyl](2,2-difluoroethyl)amino}furan-2(5H)-one (known from WO 2007/115644), 4-{[(6-chloro-5-fluoropyrid-3-yl)methyl] (methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [(6-chloropyridin-3-yl)methyl](methyl)oxido-lamda$^4$-sulphanylidenec-yanamide (known from WO 2007/149134), [1-(6-chloropyridin-3-yl)ethyl](methyl)oxido-lamda$^4$-sulphanylidene-cyanamide (known from WO 2007/149134) and its diastereomers (A) and (B) (likewise known from WO 2007/149134), [(6-trifluoromethylpyridin-3-yl)methyl](methyl)oxido-lamda$^4$-sulphanylidenecyanamide (known from WO 2007/095229), or [1-(6-trifluoromethylpyridin-3-yl)ethyl](methyl)oxido lamda$^4$-sulph-anylidenecyanamide (known from WO 2007/149134) and its diastereomers (C) and (D), namely sulfoxaflor (likewise known from WO 2007/149134).

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1. Domain Swap in Vip3D Mutant (10his-Vip3D-AAPF; P021)

One-hundred and twenty six amino acids in 10His-Vip3D-AAPF (P012) (SEQ ID NO: 6) were replaced with a carbohydrate binding module from a β-1,4 mannase (ManA) from *Thermoanaerobacterium polysaccharolyticum* (*Caldanaerobius polysaccharolyticus*). Accordingly, 137 amino acids corresponding to a CBM from GenBank ID: AAD09354.1 (620 EGGVNMVSNP GFEDGLDSWQ DWQQDMSAVP EAAHNGALGL KIGGGKAAGG GQDIPLKPNT TYILGAWAKF DSKPAGTFDV VVQYHLKDAN NTYVQHILNF NETDWTYKQL LFTTPDVFGS TPQLALWKGD TSKANLYVDD VYL-VEV 756) (SEQ ID NO:24) were inserted in place of amino acids 542-667 of P021 (542 GSIEEDNLEP WKANNKNAYV DHTGGVNGTK ALYVHKDGGF SQFIGDKLKP KTEYVIQYTV KGKPSIHLKD ENTGYIHYED TNNNLKDYQT ITKRFTTGTD LKGVYLILKS QNGDEAWGDK FTILEI 667) (SEQ ID NO:6, aa 542-667). The design was based on the atomic-resolution structure of Vip3D.

*Bacillus thuringiensis* codon tables were used for preparing the CBM portions of the chimeras. However, since expression of the chimeric nucleotide sequences was carried out in *E. coli*, the codon table could have been an *E. coli* codon table or that of another prokaryote.

The chimeric domain-swap mutant (called Vip3Dd3to2ZEX) was determined to be active (insecticidal) against black cutworm (BCW) ($LC_{50}$~700 ng/cm$^2$) and partially active toward fall armyworm (FAW) and western corn rootworm (WCR).

Example 2. Additional Domain III Swaps in P021

Based on the success of Vip3Dd3to2ZEX, eight other CBMs from eubacterial β-1,4 mannanase enzymes were substituted for Vip3D Domain III (amino acids 542-667) (Vip3Dd3) from the P021 sequence. The eight CBMs used were SEQ ID NO:8, SEQ ID NO:9, SEQ ID NO:10, SEQ ID NO:11, SEQ ID NO:12, SEQ ID NO:13, SEQ ID NO:14, and SEQ ID NO:15. One domain swap (Vip3Dd3 to 1WKy (SEQ ID NO:15) was insoluble after expression in E. coli, but the remaining 7 killed 100% BCW larvae after 7 days when assayed as an E. coli soluble crude extract (Table 1).

TABLE 1

E.coli crude extract efficacy against black cutworm at 5 and 7 days in a diet surface overlay assay.

| E.coli crude extract Treatment | Day 5 | | | Day 7 | | |
|---|---|---|---|---|---|---|
| | Total # | # Dead | % Mortality | Total # | # Dead | % Mortality |
| Empty vector control | 12 | 2 | 17% | 12 | 3 | 25% |
| Buffer control | 12 | 0 | 0% | 12 | 0 | 0% |
| P021 | 12 | 12 | 100% | 12 | 12 | 100% |
| Vip3Dd3to2ZEZ | 12 | 12 | 100% | 12 | 12 | 100% |
| Vip3Dd3to2BGP | 12 | 11 | 92% | 12 | 12 | 100% |
| Vip3Dd3to1OF3 | 12 | 12 | 100% | 12 | 12 | 100% |
| Vip3Dd3to1PMH | 12 | 11 | 92% | 12 | 12 | 100% |
| Vip3Dd3to1WKY (insoluble) | 12 | 0 | 0% | 12 | 0 | 0% |
| Vip3Dd3toCENC | 12 | 10 | 83% | 12 | 12 | 100% |
| Vip3Dd3toGP21 | 12 | 0 | 0% | 12 | 12 | 100% |
| Vip3Dd3toPsHGF7 | 12 | 12 | 100% | 12 | 12 | 100% |

Figure 2:
FIG. 2 shows ribbon diagrams of CBM structures. Top row from left to right: Vip3D Domain III, 2ZEZ, 2BGP. Middle row: 1OF3, 2ZEX, 1PMH. Bottom: 1WKY. Calcium (depicted as spheres) is shown. Sugar ligands of co-crystal structures are shown in their binding grooves (stick structures). Cloning junctions on the polypeptide chain are indicated as sticks.

The soluble fraction of lysed E. coli expressing the various CBM Vip3D Domain III (P021) swaps is provided in FIG. 2. As shown, Vip3D3d to 1WKY did not produce soluble protein. Thus, this fusion could not be tested readily for efficacy.

Each of 2ZEX, 2ZEZ, 1OF3, 1PMH, 1WKY, and 2GBP are from solved structures which contain carbohydrate binding modules from Type B β-1,4 mannanase enzymes (FIG. 3).

Figure 4:
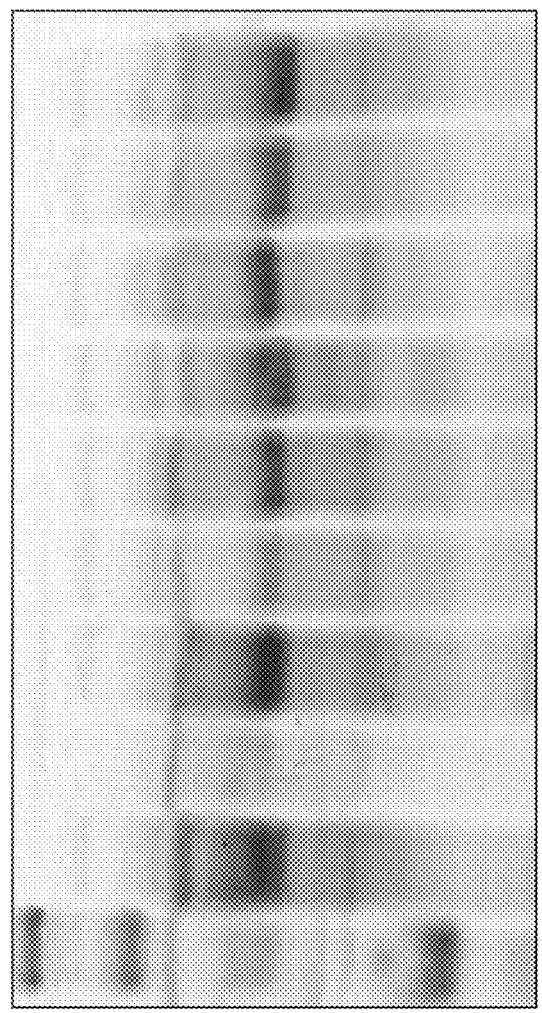
FIG. 4 shows a sodium dodecyl sulfate (SDS) PAGE gel of soluble *E. coli* crude extracts of the induced Vip3A-CBM chimeras (lanes in parentheses): Vip3A (1), 2ZEX (2), 2ZEZ (3), 1OFE (4), 1PMH (5), 2GBP (6), CENC (7), GP21 (8), and PSHGF7 (9)

In addition to testing CBM swaps based on existing Protein Databank entries, three CBM fusions from other β-1,4 mannanase proteins were tested based on their BLAST similarity: CenC, gp21, and PsHGF7 (FIG. 4).

The first swap listed in Table 1 (Vip3Dd3 to2ZEZ) is a CBM from the same enzyme as that used in Vip3Dd3to2ZEX, GenBank ID: AAD09354.1. That particular mannanase has two CBMs in tandem after the catalytic domain. 2ZEX is the first CBM immediately followed by 2ZEZ. Despite apparently having the same substrate and being connected to the same enzyme, the 2ZEZ CBM sequence shares 64% identity with 2ZEX. The 2ZEZ sequence is (756 GMDGWPDWGY PVSAVPEAAY GGTKGFKLSG GKQAGMGQKV ALKPNTTYIL GAWGKFTAKP GTYCDVIVQY HLKDANNTYV QNILRFTETD WTYKQVVFTT PDAFGSDPEF VLWKDDASNA DFYADNITLV EV 899) (SEQ ID NO:25). Both 2ZEX and 2ZEZ have been classified into CBM family 16.

Provided below are the CBM sequences that were substituted in place of amino acids 542 to 667 of P021.

```
                                            (SEQ ID NO: 28)
2BGP GenBank: AAO31761.1 endo-b1,4-mannanase 5C
[Cellvibrio japonicus]. CBM35 (208
TAASASITAP AQLVGNVGEL QGAGSAVIWN VDVPVTGEYR
INLTWSSPYS SKVNTLVMDG TALSYAFAEA TVPVTYVQTK
TLSAGNHSFG VRVGSSDWGY MNVHSLKLEL LG 319)
```

```
                                            (SEQ ID NO: 26)
1OFE is from the C-terminal 176 amino acids of a
Thermotoga maritima endo β-1,4 mannanase. It has
been classified into CBM family 27. NP_229032 amino
acids (505
DFSSPEEVKN WWNSGTWQAE FGSPDIEWNG EVGNGALQLN VKLPGKSDWE
EVRVARKFER LSECEILEYD IYIPNVEGLK GRLRPYAVLN PGWVKIGLDM
NNANVESAEI ITFGGKEYRR FHVRIEFDRT AGVKELHIGV VGDHLRYDGP
IFIDNVRLYKR 665) were cloned into Vip3D domain 3.
```

```
                                            (SEQ ID NO: 27)
1PMH. CBM27-1. GenBank: AAC44232.1. Caldicellulosiruptor
saccharolyticus β-1,4 mannanase. (45
DFEDGTVMSF GEAWGDSLKC IKKVSVSQDL QRPGNKYALR LDVEFNPNNG
WDQGDLGTWI GGWEGQFDF TGYKSVEFEM FIPYDEFSKS QGGFAYKWI
NDGWKELGSE FNITANAGKK VKINGKDYTV IHKAFAIPED FRTKKRAQLV
FQFAGQNSNY KGPIYLDNVR IRPE 218)
```

```
                                            (SEQ ID NO: 32)
1WKY. CBM59. β-1,4-mannanase. Caldicellulosiruptor
saccharolyticus. (alkaline mannanase) (Amn5).
GenBank: AAC44232.1; (345
DFEESTQGWT GSSLSRGPWT VTEWSSKGNH SLKADIQMSS NSQHYLHVIQ
NRSLQQNSRI QATVKHANWG SVGNGMTARL YVKTGHGYTW YSGSFVPING
SSGTTLSLDL SNVQNLSQVR EIGVQFQSES NSSGQTSIYI DNVIVE 490)
```

-continued

```
                                            (SEQ ID NO: 30)
CenC. carbohydrate-binding. CenC domain protein
[Paenibacillus sp. JDR-2]. NCBI Reference Sequence:
YP_003011283.1.; (202
PGLEDGINNW QAWGEGFTAA SDMSHTGSAS LKVLLNNGGR QVVALQPGKS
YKLGVWGKTA GTGTGTQTAT VMINYKKPED DSSHTYGSFQ FGPDNSEFTY
KEITFETPDD MAQEWGTQFV SIWSEGADQV YLDDFTLSEV 341)

(SEQ ID NO: 29)
Gp21. Gp21 [Klebsiella pneumoniae subsp. pneumoniae HS11286].
NCBI Reference Sequence: YP_005220866.1.; (69
PSFERGTEGY TGWSGIATVV TLQVPHLGTK AAKLAAGGSA
GVGQKISFKK DRSYKIGIWA KQDPNTTIQS TDNTKFRVAD
GNGLIASKAY GPFTSNWQEV SWTWKATKDV LADVQFTAFL
SAGAMYFDDF YWDV 203)

(SEQ ID NO: 31)
PsHGF7. carbohydrate binding domain protein [Paenibacillus
sp. HGF7]. NCBI Reference Sequence: WP_009674454.1. (66
PGFEDNLASW TNWGNTSSVT SPAFAGAKAA RIASGEGGAG QIIPGIPSGT
TYVLSGHGSV SAGTDTAIVG VDCLDANNNV LAKNTLRFNQ TLYEFKSTAF
TTVPGTAKLQ VYIYKNADSG ANAFLDDLSL VEV 195)
```

Schematics of the substitutions are provided in FIGS. 6A-6C.

Example 3. Activity Spectrum Test

All soluble constructs were purified via nickel affinity chromatography. The proteins exchanged into phosphate buffered saline (PBS) and tested via diet overlay against a variety of lepidopteran species at the L1-L2 stage (n=12). Two doses were tested: 32 µg/cm$^2$ and 1 µg/cm$^2$. Controls were purified P021, which is 10-histidine tagged Vip3D with amino acids AAPF substituted at the active site (SEQ ID NO:6) and a buffer control (PBS). The activity of each of the constructs was tested against European Corn Borer (ECB), Corn Earworm (CEM), Black Cutworm (BCW), and Fall Armyworm (FAW). The results of the activity tests are provided in Table 2, below.

TABLE 2

Activity of P012 swaps against European Corn Borer (ECB), Corn Earworm (CEM), Black Cutworm (BCW), and Fall Armyworm (FAW).

144 hour assay
Diet overlay

| European Corn Borer | % Mortality 32 µg/cm$^2$ | % Mortality 1 µg/cm$^2$ | Corn Earworm | % Mortality 32 µg/cm$^2$ | % Mortality 1 µg/cm$^2$ |
|---|---|---|---|---|---|
| P021 (HisVip3D_AAPF) | 100 | 8 | P021 (HisVip3D_AAPF) | 100 | 83 |
| Vip3Dd3_to_2ZEX | 17 | 0 | Vip3Dd3_to_2ZEX | 75 | 100 |
| Vip3Dd3_to_2ZEZ | 0 | 0 | Vip3Dd3_to_2ZEZ | 92 | 92 |
| Vip3Dd3_to_1OFE | 0 | 0 | Vip3Dd3_to_1OFE | 0 | 67 |
| Vip3Dd3_to_1PMH | 0 | 8 | Vip3Dd3_to_1PMH | 25 | 8 |
| Vip3Dd3_to_2BGP | 0 | 0 | Vip3Dd3_to_2BGP | 33 | 83 |
| Vip3Dd3_to_GP21 | 67 | 0 | Vip3Dd3_to_GP21 | 100 | 92 |
| Vip3Dd3_to_CENC | 0 | 0 | Vip3Dd3_to_CENC | 0 | 0 |
| Vip3Dd3_to_PSHGF7 | 0 | 0 | Vip3Dd3_to_PSHGF7 | 83 | 33 |
| PBS | 8 | 0 | PBS | 8 | 8 |

| Black Cutworm | % Mortality 32 µg/cm$^2$ | % Mortality 1 µg/cm$^2$ | Fall Armyworm | % Mortality 32 µg/cm$^2$ | % Mortality 1 µg/cm$^2$ |
|---|---|---|---|---|---|
| P021 (HisVip3D_AAPF) | 100 | 100 | P021(HisVip3D_AAPF) | 100 | 100 |
| Vip3Dd3_to_2ZEX | 100 | 92 | Vip3Dd3_to_2ZEX | 100 | 92 |
| Vip3Dd3_to_2ZEZ | 100 | 83 | Vip3Dd3_to_2ZEZ | 100 | 67 |
| Vip3Dd3_to_1OFE | 92 | 0 | Vip3Dd3_to_1OFE | 33 | 8 |
| Vip3Dd3_to_1PMH | 92 | 0 | Vip3Dd3_to_1PMH | 42 | 17 |
| Vip3Dd3_to_2BGP | 92 | 25 | Vip3Dd3_to_2BGP | 25 | 17 |
| Vip3Dd3_to_GP21 | 100 | 100 | VipDd3_to_GP21 | 100 | 100 |
| Vip3Dd3_to_CENC | 100 | 90 | Vip3Dd3_to_CENC | 33 | 8 |
| Vip3Dd3_to_PSHGF7 | 100 | 92 | Vip3Dd3_to_PSHGF7 | 100 | 83 |
| PBS | 0 | 0 | PBS | 0 | 8 |

The results of swapping β-1,4 mannanase Type B CBM sequences in place of Vip3D Domain III are clear. Broad spectrum Lepidoptera control is observed using purified proteins. Certain chimeras were more or less toxic to any given insect at a particular dose. For example Vip3Dd3_to_GP21 seems to be one of the most toxic of the fusions against the particular insects tested; however, it is less toxic against CEW than is Vip3Dd3_to_2ZEX. The chimeras are likely to be useful in controlling multiple lepidopteran and other agricultural pests.

Example 4. Vip3A Swaps

The same CBM domains that were swapped with Domain III of P021 as described in Examples 1 and 2 were swapped with Domain III of Vip3A polypeptides. The CBM domains were cloned onto the Vip3A scaffold at the same junction points (e.g., amino acids 541 and 668) as in Vip3D P021. The Vip3A proteins did not have the AAPF change in the activation site and did not contain an N-terminal histidine tag as in P021. Due to a lack of a single-column purification step, E. coli soluble crude extract diet overlays were used for the spectrum test. These constructs expressed well in crude extracts and as such these assays were a high-dose test. An empty-vector E. coli crude extract was included as a control. The results are provided in Table 3, below.

The SDS-PAGE gel shows that nearly all proteins were highly soluble, with the exception of the 2ZEX and 1OFE chimeras (FIG. 5). These two constructs did have some soluble protein expression and activity as shown in Table 3 (below).

TABLE 3

Activity of Vip3A Domain III swaps against European Corn Borer (ECB), Corn Earworm (CEM), Black Cutworm (BCW), and Fall Army worm (FAW).

144 hour assay
Diet overlay

| European Corn Borer | % Mortality Crude Extract | Corn Earworm | % Mortality Crude Extract |
|---|---|---|---|
| Empty Vector | 0% | Empty Vector | 0% |
| Vip3Ad3_to_2ZEX | 0% | Vip3Ad3_to_2ZEX | 75% |
| Vip3Ad3_to_2ZEZ | 25% | Vip3Ad3_to_2ZEZ | 100% |
| Vip3Ad3_to_1OFE | 0% | Vip3Ad3_to_1OFE | 0% |
| Vip3Ad3_to_1PMH | 0% | Vip3Ad3_to_1PMH | 75% |
| Vip3Ad3_to_2BGP | 0% | Vip3Ad3_to_2BGP | 100% |
| Vip3Ad3_to_GP21 | 33% | Vip3Ad3_to_GP21 | 100% |
| Vip3Ad3_to_CENC | 0% | Vip3Ad3_to_CENC | 83% |
| Vip3Ad3_to_PSHGF7 | 0% | Vip3Ad3_to_PSHGF7 | 100% |
| PBS | 0% | PBS | 0% |

| Black Cutworm | Mortality % Crude Extract | Fall Armyworm | Mortality % Crude Extract |
|---|---|---|---|
| Empty Vector | 0% | Empty Vector | 0% |
| Vip3Ad3_to_2ZEX | 100% | Vip3Ad3_to_2ZEX | 100% |
| Vip3Ad3_to_2ZEZ | 100% | Vip3Ad3_to_2ZEZ | 100% |
| Vip3Ad3_to_1OFE | 100% | Vip3Ad3_to_1OFE | 8% |
| Vip3Ad3_to_1PMH | 100% | Vip3Ad3_to_1PMH | 100% |
| Vip3Ad3_to_2BGP | 100% | Vip3Ad3_to_2BGP | 100% |
| Vip3Ad3_to_GP21 | 100% | Vip3Ad3_to_GP21 | 100% |
| Vip3Ad3_to_CENC | 100% | Vip3Ad3_to_CENC | 100% |
| Vip3Ad3_to_PSHGF7 | 100% | Vip3Ad3_to_PSHGF7 | 100% |
| PBS | 0% | PBS | 0% |

The results show that the same CBM swaps are effective for broad lepidopteran control in Vip3A. The overall pattern in ECB is similar to the high-dose Vip3D swaps with 2ZEZ and GP21 being most active. The other 3 insect species tested were also highly susceptible to these fusions. However, the 1OFE swap was only toxic to BCW. Gel analysis indicates that 1OFE was expressed at much lower levels than most of the other proteins (FIG. 5), which could account for the aberrant inactivity. The 2ZEX fusion was also expressed at lower levels but showed high activity to all insect larvae except ECB. The data in the above examples show that Type B Carbohydrate Binding Modules from β 1,4 mannanase enzymes can be swapped in place of Domain III of Vip3 polypeptides to generate active toxins. These toxins showed differential activity towards the four Lepidoptera species tested with the majority killing FAW, CEW, and BCW. ECB was effectively targeted by two chimeras. Vip3D and Vip3A both served as good scaffolds for these designs and generated differential activities. The insects tested are exemplary of the types that may be controlled by the constructs of this invention. Further, the specific CBMs that are swapped for Domain III of Vip3 polypeptides are also exemplary of the types of CBM domains that can be used with this invention. Thus, any β-1,4 mannanase CBM, in particular any β-1,4 mannanase Type B CBM, may be useful with this invention when introduced into aVip3 polypeptide or exchanged with Domain III of a Vip3 polypeptide. Further, in some embodiments, any CBM having at least 70% homology or identity to any one of the amino acid sequence of SEQ ID NOs:24 to 32 may be useful with this invention when introduced into aVip3 polypeptide or exchanged with Domain III of a Vip3 polypeptide.

Notably, in addition to controlling insects directly with the compositions described herein, the constructs can also be expressed in transgenic plants providing additional tools to the farmer for control of plant pests.

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

That which is claimed is:

1. A modified Vip3 polypeptide comprising a heterologous carbohydrate binding module (CBM), wherein the CBM is from a bacterial β-1,4-mannanase comprising SEQ ID NO:25 and is substituted for all or a portion of Domain III of the Vip3 polypeptide, and wherein the modified Vip3 polypeptide is pesticidal against an insect.

2. The modified Vip3 polypeptide of claim 1, wherein the Vip3 polypeptide comprises all or a portion of SEQ ID NO:1.

3. The modified Vip3 polypeptide of claim 1, wherein all or a portion of Domain III comprises amino acids 542 to 667 of SEQ ID NO:1.

4. The modified Vip3 polypeptide of claim 1, wherein all or a portion of Domain III comprises amino acids 542-667 of SEQ ID NO:2.

5. The modified Vip3 polypeptide of claim 1, wherein the heterologous CBM comprises a metal binding site.

6. The modified Vip3 polypeptide of claim 1, wherein the modified Vip3 polypeptide is pesticidal against a lepidopteran insect.

7. The modified Vip3 polypeptide of claim 1, wherein the modified Vip3 polypeptide is pesticidal against at least one of *Ostrinia nubilalis* (European corn borer), *Plutella xylostella* (diamondback moth), *Spodoptera frugiperda* (fall armyworm), *Agrotis ipsilon* (black cutworm), *Agrotis orthogonia* (pale western cutworm), *Striacosta albicosta* (western bean cutworm), *Helicoverpa zea* (corn earworm), *Heliothis virescens* (tobacco budworm), *Spodoptera exigua* (beet armyworm), *Helicoverpa punctigera* (native budworm), *Helicoverpa armigera* (cotton bollworm), *Manduca sexta* (tobacco hornworm), *Trichoplusia ni* (cabbage looper), *Pectinophora gossypiella* (pink bollworm), *Diatraea grandiosella* (southwestern corn borer), *Diatraea saccharalis* (sugarcane borer), *Elasmopalpus lignosellus* (lesser cornstalk borer), *Psuedoplusia includens* (soybean looper), *Anticarsia gemmatalis* (velvetbean caterpillar), *Plathypena scabra* (green cloverworm), *Homoeosoma electellum* (sunflower head moth), and *Cochylis hospes* (banded sunflower moth), or any combination thereof.

8. A composition comprising the modified Vip3 polypeptide of claim 1 in an agriculturally acceptable carrier.

9. A nucleic acid molecule comprising a nucleotide sequence encoding the polypeptide of claim 1.

10. A transgenic host cell comprising the nucleic acid molecule of claim 9.

11. The transgenic host cell of claim 10, wherein the transgenic host cell is a transgenic plant cell or a transgenic bacterial cell.

12. A transgenic plant comprising the transgenic plant cell of claim 11.

13. The modified Vip3 polypeptide of claim 1, wherein the Vip3 polypeptide comprises all or a portion of SEQ ID NO:2.

14. The modified Vip3 polypeptide of claim 1, wherein the modified Vip3 polypeptide comprises SEQ ID NO:8.

15. The modified Vip3 polypeptide of claim 1, wherein the modified Vip3 polypeptide comprises SEQ ID NO:17.

* * * * *

SEQUENCE LISTING

<160> NUMBER OF SEQ ID NOS: 56

<210> SEQ ID NO 1
<211> LENGTH: 788
<212> TYPE: PRT
<213> ORGANISM: Bacillus thuringiensis
<220> FEATURE:
<221> NAME/KEY: MISC_FEATURE
<222> LOCATION: (1)..(788)
<223> OTHER INFORMATION: Vip3D amino acid sequence

<400> SEQUENCE: 1

```
Met Asn Met Asn Asn Thr Lys Leu Asn Ala Arg Ala Leu Pro Ser Phe
1               5                  10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350
```

```
Pro Gly His Ala Leu Val Gly Phe Glu Met Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Thr Asp Lys Leu Phe
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
            435                 440                 445

Glu Ile Asp Leu Asn Lys Lys Lys Val Glu Ser Ser Glu Ala Glu Tyr
        450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
            515                 520                 525

Val Pro Pro Ser Gly Phe Ile Ser Asn Ile Val Glu Asn Gly Ser Ile
        530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Phe Ser Gln Phe Ile Gly Asp Lys Leu Lys Pro Lys
                580                 585                 590

Thr Glu Tyr Val Ile Gln Tyr Thr Val Lys Gly Lys Pro Ser Ile His
            595                 600                 605

Leu Lys Asp Glu Asn Thr Gly Tyr Ile His Tyr Glu Asp Thr Asn Asn
        610                 615                 620

Asn Leu Lys Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Lys Phe Thr Ile Leu Glu Ile Lys Pro Ala Glu Asp
                660                 665                 670

Leu Leu Ser Pro Glu Leu Ile Asn Pro Asn Ser Trp Ile Thr Thr Pro
            675                 680                 685

Gly Ala Ser Ile Ser Gly Asn Lys Leu Phe Ile Asn Leu Gly Thr Asn
        690                 695                 700

Gly Thr Phe Arg Gln Ser Leu Ser Leu Asn Ser Tyr Ser Thr Tyr Ser
705                 710                 715                 720

Ile Ser Phe Thr Ala Ser Gly Pro Phe Asn Val Thr Val Arg Asn Ser
                725                 730                 735

Arg Glu Val Leu Phe Glu Arg Ser Asn Leu Met Ser Ser Thr Ser His
                740                 745                 750

Ile Ser Gly Thr Phe Lys Thr Glu Ser Asn Asn Thr Gly Leu Tyr Val
            755                 760                 765
```

-continued

Glu Leu Ser Arg Arg Ser Gly Gly Gly His Ile Ser Phe Glu Asn
770                 775                 780

Val Ser Ile Lys
785

<210> SEQ ID NO 2
<211> LENGTH: 789
<212> TYPE: PRT
<213> ORGANISM: Bacillus thuringiensis
<220> FEATURE:
<221> NAME/KEY: MISC_FEATURE
<222> LOCATION: (1)..(789)
<223> OTHER INFORMATION: Vip3A amino acid sequence

<400> SEQUENCE: 2

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Gln Ala Phe Leu Thr
        275                 280                 285

Leu Thr Thr Cys Arg Lys Leu Leu Gly Leu Ala Asp Ile Asp Tyr Thr
290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala

-continued

```
                325                 330                 335
Lys Val Lys Gly Ser Asp Glu Asp Ala Lys Met Ile Val Glu Ala Lys
            340                 345                 350
Pro Gly His Ala Leu Ile Gly Phe Glu Ile Ser Asn Asp Ser Ile Thr
            355                 360                 365
Val Leu Lys Val Tyr Glu Ala Lys Leu Lys Gln Asn Tyr Gln Val Asp
            370                 375                 380
Lys Asp Ser Leu Ser Glu Val Ile Tyr Gly Asp Met Asp Lys Leu Leu
385                 390                 395                 400
Cys Pro Asp Gln Ser Glu Gln Ile Tyr Tyr Thr Asn Asn Ile Val Phe
                405                 410                 415
Pro Asn Glu Tyr Val Ile Thr Lys Ile Asp Phe Thr Lys Lys Met Lys
            420                 425                 430
Thr Leu Arg Tyr Glu Val Thr Ala Asn Phe Tyr Asp Ser Ser Thr Gly
            435                 440                 445
Glu Ile Asp Leu Asn Lys Lys Lys Val Glu Ser Ser Glu Ala Glu Tyr
            450                 455                 460
Arg Thr Leu Ser Ala Asn Asp Asp Gly Val Tyr Met Pro Leu Gly Val
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
            500                 505                 510
Glu Leu Leu Leu Ala Thr Asp Leu Ser Asn Lys Glu Thr Lys Leu Ile
            515                 520                 525
Val Pro Pro Ser Gly Phe Ile Ser Asn Ile Val Glu Asn Gly Ser Ile
            530                 535                 540
Glu Glu Asp Asn Leu Glu Pro Trp Lys Ala Asn Asn Lys Asn Ala Tyr
545                 550                 555                 560
Val Asp His Thr Gly Gly Val Asn Gly Thr Lys Ala Leu Tyr Val His
                565                 570                 575
Lys Asp Gly Gly Ile Ser Gln Phe Ile Gly Asp Lys Leu Lys Pro Lys
            580                 585                 590
Thr Glu Tyr Val Ile Gln Tyr Thr Val Lys Gly Lys Pro Ser Ile His
            595                 600                 605
Leu Lys Asp Glu Asn Thr Gly Tyr Ile His Tyr Glu Asp Thr Asn Asn
            610                 615                 620
Asn Leu Glu Asp Tyr Gln Thr Ile Asn Lys Arg Phe Thr Thr Gly Thr
625                 630                 635                 640
Asp Leu Lys Gly Val Tyr Leu Ile Leu Lys Ser Gln Asn Gly Asp Glu
                645                 650                 655
Ala Trp Gly Asp Asn Phe Ile Ile Leu Glu Ile Ser Pro Ser Glu Lys
            660                 665                 670
Leu Leu Ser Pro Glu Leu Ile Asn Thr Asn Asn Trp Thr Ser Thr Gly
            675                 680                 685
Ser Thr Asn Ile Ser Gly Asn Thr Leu Thr Leu Tyr Gln Gly Gly Arg
            690                 695                 700
Gly Ile Leu Lys Gln Asn Leu Gln Leu Asp Ser Phe Ser Thr Tyr Arg
705                 710                 715                 720
Val Tyr Phe Ser Val Ser Gly Asp Ala Asn Val Arg Ile Arg Asn Ser
                725                 730                 735
Arg Glu Val Leu Phe Glu Lys Arg Tyr Met Ser Gly Ala Lys Asp Val
            740                 745                 750
```

```
Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Tyr
770                 775                 780

Asp Val Ser Ile Lys
785

<210> SEQ ID NO 3
<211> LENGTH: 787
<212> TYPE: PRT
<213> ORGANISM: Bacillus thuringiensis
<220> FEATURE:
<221> NAME/KEY: MISC_FEATURE
<222> LOCATION: (1)

```
Ser Ile Met Asn Glu His Leu Asn Lys Glu Lys Glu Phe Arg Val
305                 310                 315                 320

Asn Ile Leu Pro Thr Leu Ser Asn Thr Phe Ser Asn Pro Asn Tyr Ala
            325                 330                 335

Lys Val Lys Gly Ser Asp Glu Asp Ala Lys Met Ile Val Glu Ala Lys
                340                 345                 350

Pro Gly His Ala Leu Val Gly Phe Glu Ile Ser Asn Asp Ser Met Thr
            355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Ser Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Ser Tyr Asp Ser Ser Thr Gly
        435                 440                 445

Glu Ile Asp Leu Asn Lys Lys Lys Val Glu Ser Ser Glu Ala Glu Tyr
450                 455                 460

Arg Thr Leu Ser Ala Asn Asn Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ile Ser Phe Ile Ser Asn Ile Val Glu Asn Gly Asn Leu
530                 535                 540

Glu Gly Glu Asn Leu Glu Pro Trp Ile Ala Asn Asn Lys Asn Ala Tyr
545                 550                 555                 560

Val Asp His Thr Gly Gly Ile Asn Gly Thr Lys Val Leu Tyr Val His
                565                 570                 575

Lys Asp Gly Glu Phe Ser Gln Phe Val Gly Gly Lys Leu Lys Ser Lys
            580                 585                 590

Thr Glu Tyr Val Ile Gln Tyr Ile Val Lys Gly Lys Ala Ser Ile Tyr
        595                 600                 605

Leu Lys Asp Lys Lys Asn Glu Asn Ser Ile Tyr Glu Glu Ile Asn Asn
610                 615                 620

Asp Leu Glu Gly Phe Gln Thr Val Thr Lys Arg Phe Ile Thr Gly Thr
625                 630                 635                 640

Asp Ser Ser Gly Ile His Leu Ile Phe Thr Ser Gln Asn Gly Glu Gly
                645                 650                 655

Ala Phe Gly Gly Asn Phe Ile Ile Ser Glu Ile Arg Thr Ser Glu Glu
            660                 665                 670

Leu Leu Ser Pro Glu Leu Ile Met Ser Asp Ala Trp Val Gly Ser Gln
        675                 680                 685

Gly Thr Trp Ile Ser Gly Asn Ser Leu Thr Ile Asn Ser Asn Val Asn
690                 695                 700

Gly Thr Phe Arg Gln Asn Leu Pro Leu Glu Ser Tyr Ser Thr Tyr Ser
705                 710                 715                 720

Met Asn Phe Thr Val Asn Gly Phe Gly Lys Val Thr Val Arg Asn Ser
```

```
                    725                 730                 735
Arg Glu Val Leu Phe Glu Lys Ser Tyr Pro Gln Leu Ser Pro Lys Asp
            740                 745                 750

Ile Ser Glu Lys Phe Thr Thr Ala Ala Asn Asn Thr Gly Leu Tyr Val
            755                 760                 765

Glu Leu Ser Arg Ser Thr Ser Gly Gly Ala Ile Asn Phe Arg Asp Phe
        770                 775                 780

Ser Ile Lys
785

<210> SEQ ID NO 4
<211> LENGTH: 803
<212> TYPE: PRT
<213> ORGANISM: Bacillus thuringiensis
<220> FEATURE:
<221> NAME/KEY: MISC_FEATURE
<222> LOCATION: (1)..(803)
<223> OTHER INFORMATION: Vip3C amino acid sequence

<400> SEQUENCE: 4

Met Asn Lys Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Asn Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Arg
    130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
        195                 200                 205

Asn Thr Leu Glu Asn Leu Thr Asp Leu Ala Glu Leu Ala Lys Ser Ile
    210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
            260                 265                 270

Ile Gly Lys Val Tyr Ser Phe Leu Ile Val Leu Thr Ser Leu Gln Ala
        275                 280                 285
```

```
Lys Ala Phe Leu Thr Leu Thr Thr Cys Arg Lys Leu Leu Gly Leu Ser
    290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                    325                 330                 335

Asn Pro Ser Tyr Ala Lys Thr Ile Gly Ser Asp Asn Tyr Ala Lys Val
                340                 345                 350

Ile Leu Glu Ser Glu Pro Gly Tyr Ala Leu Val Gly Phe Glu Ile Ile
            355                 360                 365

Asn Asp Pro Ile Pro Val Leu Lys Ala Tyr Lys Ala Lys Leu Lys Gln
        370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                    405                 410                 415

Lys Asn Leu Thr Phe Pro Asp Gly Tyr Val Ile Thr Lys Ile Thr Phe
                420                 425                 430

Glu Lys Lys Leu Asn Asn Leu Ile Tyr Glu Ala Thr Ala Asn Phe Tyr
            435                 440                 445

Asp Pro Ser Thr Gly Asp Ile Asp Leu Asn Lys Lys Gln Val Glu Ser
        450                 455                 460

Thr Phe Pro Gln Thr Asp Tyr Ile Thr Met Asp Ile Gly Asp Asp Asp
465                 470                 475                 480

Gly Ile Tyr Met Pro Leu Gly Val Ile Ser Glu Thr Phe Leu Thr Pro
                    485                 490                 495

Ile Asn Ser Phe Gly Leu Glu Val Asp Ala Lys Ser Lys Thr Leu Thr
                500                 505                 510

Leu Lys Cys Lys Ser Tyr Leu Arg Glu Tyr Leu Leu Glu Ser Asp Leu
            515                 520                 525

Lys Asn Lys Glu Thr Gly Leu Ile Ala Pro Pro Asn Val Phe Ile Ser
        530                 535                 540

Asn Val Val Lys Asn Trp Asp Ile Glu Glu Asp Ser Leu Glu Pro Trp
545                 550                 555                 560

Val Ala Asn Asn Lys Asn Ala Tyr Val Asp Asn Thr Gly Gly Ile Glu
                    565                 570                 575

Arg Ser Lys Ala Leu Phe Thr Gln Gly Asp Gly Glu Phe Ser Gln Phe
                580                 585                 590

Ile Gly Asp Lys Leu Lys Pro Asn Thr Asp Tyr Ile Ile Gln Tyr Thr
            595                 600                 605

Val Lys Gly Lys Pro Ala Ile Tyr Leu Lys Asn Lys Ser Thr Gly Tyr
        610                 615                 620

Ile Thr Tyr Glu Asp Thr Asn Gly Asn Ser Glu Glu Phe Gln Thr Ile
625                 630                 635                 640

Ala Val Lys Phe Thr Ser Glu Thr Asp Leu Ser Gln Thr His Leu Val
                    645                 650                 655

Phe Lys Ser Gln Asn Gly Tyr Glu Ala Trp Gly Asp Asn Phe Ile Ile
                660                 665                 670

Leu Glu Ala Lys Leu Phe Glu Thr Pro Glu Ser Pro Glu Leu Ile Lys
            675                 680                 685

Phe Asn Asp Trp Glu Arg Phe Gly Thr Thr Tyr Ile Thr Gly Asn Glu
        690                 695                 700
```

```
Leu Arg Ile Asp His Ser Arg Gly Gly Tyr Phe Arg Gln Ser Leu Asn
705                 710                 715                 720

Ile Asp Ser Tyr Ser Thr Tyr Asp Leu Ser Phe Ser Phe Ser Gly Leu
            725                 730                 735

Trp Ala Lys Val Ile Val Lys Asn Ser Arg Gly Val Val Leu Phe Glu
            740                 745                 750

Lys Val Lys Asn Asn Gly Ser Ser Tyr Glu Asp Ile Ser Glu Ser Phe
            755                 760                 765

Thr Thr Ala Ser Asn Lys Asp Gly Phe Phe Ile Glu Leu Thr Ala Glu
            770                 775                 780

Arg Thr Ser Ser Thr Phe His Ser Phe Arg Asp Ile Ser Ile Lys Glu
785                 790                 795                 800

Lys Ile Glu

<210> SEQ ID NO 5
<211> LENGTH: 781
<212> TYPE: PRT
<213> ORGANISM: Artificial
<220> FEATURE:
<223> OTHER INFORMATION: Consensus Vip3 amino acid sequence

<400> SEQUENCE: 5

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
```

```
            260                 265                 270
Asn Phe Leu Ile Val Leu Thr Ala Leu Gln Ala Lys Ala Phe Leu Thr
            275                 280                 285
Leu Thr Thr Cys Arg Lys Leu Leu Gly Leu Ala Asp Ile Asp Tyr Thr
            290                 295                 300
Ser Ile Met Asn Glu His Leu Asn Lys Glu Lys Glu Glu Phe Arg Val
305                 310                 315                 320
Asn Ile Leu Pro Thr Leu Ser Asn Thr Phe Ser Asn Pro Asn Tyr Ala
            325                 330                 335
Lys Val Lys Gly Ser Asp Glu Asp Ala Lys Met Ile Val Glu Ala Lys
            340                 345                 350
Pro Gly His Ala Leu Val Gly Phe Glu Ile Ser Asn Asp Ser Ile Thr
            355                 360                 365
Val Leu Lys Val Tyr Glu Ala Lys Leu Lys Gln Asn Tyr Gln Val Asp
            370                 375                 380
Lys Asp Ser Leu Ser Glu Val Ile Tyr Gly Asp Met Asp Lys Leu Leu
385                 390                 395                 400
Cys Pro Asp Gln Ser Glu Gln Ile Tyr Tyr Thr Asn Asn Ile Val Phe
            405                 410                 415
Pro Asn Glu Tyr Val Ile Thr Lys Ile Asp Phe Thr Lys Lys Met Lys
            420                 425                 430
Thr Leu Arg Tyr Glu Val Thr Ala Asn Phe Tyr Asp Ser Ser Thr Gly
            435                 440                 445
Glu Ile Asp Leu Asn Lys Lys Lys Val Glu Ser Ser Glu Ala Glu Tyr
            450                 455                 460
Arg Thr Leu Ser Ala Asn Asp Asp Gly Val Tyr Met Pro Leu Gly Val
465                 470                 475                 480
Ile Ser Glu Thr Phe Leu Thr Pro Ile Asn Gly Phe Gly Leu Gln Ala
            485                 490                 495
Asp Glu Asn Ser Arg Leu Ile Thr Leu Thr Cys Lys Ser Tyr Leu Arg
            500                 505                 510
Glu Leu Leu Leu Ala Thr Asp Leu Ser Asn Lys Glu Thr Lys Leu Ile
            515                 520                 525
Val Pro Pro Ser Gly Phe Ile Ser Asn Ile Val Glu Asn Gly Ser Ile
            530                 535                 540
Glu Glu Asp Asn Leu Glu Pro Trp Lys Ala Asn Asn Lys Asn Ala Tyr
545                 550                 555                 560
Val Asp His Thr Gly Gly Ile Asn Gly Thr Lys Ala Leu Tyr Val His
            565                 570                 575
Lys Asp Gly Gly Phe Ser Gln Phe Ile Gly Asp Lys Leu Lys Pro Lys
            580                 585                 590
Thr Glu Tyr Val Ile Gln Tyr Thr Val Lys Gly Lys Pro Ser Ile His
            595                 600                 605
Leu Lys Asp Lys Asn Thr Gly Tyr Ile His Tyr Glu Asp Thr Asn Asn
            610                 615                 620
Asn Leu Glu Asp Phe Gln Thr Ile Thr Lys Arg Phe Thr Thr Gly Thr
625                 630                 635                 640
Asp Leu Ser Gly Val His Leu Ile Leu Lys Ser Gln Asn Gly Asp Glu
            645                 650                 655
Ala Trp Gly Asp Asn Phe Ile Ile Leu Glu Ile Lys Pro Ser Glu Asp
            660                 665                 670
Leu Leu Ser Pro Glu Leu Ile Asn Ser Asn Ala Trp Ile Ser Thr Gly
            675                 680                 685
```

```
Gly Thr Trp Ile Ser Gly Asn Ser Leu Thr Ile Asn Gly Asn Gly Thr
            690             695             700

Phe Arg Gln Ser Leu Asn Leu Asp Ser Tyr Ser Thr Tyr Ser Ile Ser
705             710             715             720

Phe Ser Val Ser Gly Phe Ala Asn Val Thr Val Arg Asn Ser Arg Glu
            725             730             735

Val Leu Phe Glu Lys Ser Met Ser Ser Lys Asp Ile Ser Glu Ser Phe
            740             745             750

Thr Thr Ala Ser Asn Asn Thr Gly Leu Tyr Ile Glu Leu Ser Arg Ser
            755             760             765

Thr Ser Gly Gly Ile Ser Phe Arg Asp Val Ser Ile Lys
            770             775             780

<210> SEQ ID NO 6
<211> LENGTH: 798
<212> TYPE: PRT
<213> ORGANISM: Artificial
<220> FEATURE:
<223> OTHER INFORMATION: 10His-Vip3D-AAPH amino acid sequence

<400> SEQUENCE: 6

Met His His His His His His His His Asn Met Asn Asn Thr
1               5                   10                  15

Lys Leu Asn Ala Arg Ala Leu Pro Ser Phe Ile Asp Tyr Phe Asn Gly
            20                  25                  30

Ile Tyr Gly Phe Ala Thr Gly Ile Lys Asp Ile Met Asn Met Ile Phe
        35                  40                  45

Lys Thr Asp Thr Gly Gly Asn Leu Thr Leu Asp Glu Ile Leu Lys Asn
50              55                  60

Gln Gln Leu Leu Asn Glu Ile Ser Gly Lys Leu Asp Gly Val Asn Gly
65                  70                  75                  80

Ser Leu Asn Asp Leu Ile Ala Gln Gly Asn Leu Asn Thr Glu Leu Ser
                85                  90                  95

Lys Glu Ile Leu Lys Ile Ala Asn Glu Gln Asn Gln Val Leu Asn Asp
            100                 105                 110

Val Asn Asn Lys Leu Asp Ala Ile Asn Thr Met Leu His Ile Tyr Leu
        115                 120                 125

Pro Lys Ile Thr Ser Met Leu Ser Asp Val Met Lys Gln Asn Tyr Ala
        130                 135                 140

Leu Ser Leu Gln Ile Glu Tyr Leu Ser Lys Gln Leu Gln Glu Ile Ser
145                 150                 155                 160

Asp Lys Leu Asp Ile Ile Asn Val Asn Val Leu Ile Asn Ser Thr Leu
                165                 170                 175

Thr Glu Ile Thr Pro Ala Tyr Gln Arg Ile Lys Tyr Val Asn Glu Lys
            180                 185                 190

Phe Glu Glu Leu Thr Phe Ala Thr Glu Ala Ala Pro Phe Val Lys Lys
        195                 200                 205

Asp Ser Ser Pro Ala Asp Ile Leu Asp Glu Leu Thr Glu Leu Thr Glu
        210                 215                 220

Leu Ala Lys Ser Val Thr Lys Asn Asp Val Asp Gly Phe Glu Phe Tyr
225                 230                 235                 240

Leu Asn Thr Phe His Asp Val Met Val Gly Asn Asn Leu Phe Gly Arg
                245                 250                 255

Ser Ala Leu Lys Thr Ala Ser Glu Leu Ile Ala Lys Glu Asn Val Lys
            260                 265                 270
```

```
Thr Ser Gly Ser Glu Val Gly Asn Val Tyr Asn Phe Leu Ile Val Leu
        275                 280                 285

Thr Ala Leu Gln Ala Lys Ala Phe Leu Thr Leu Thr Thr Cys Arg Lys
    290                 295                 300

Leu Leu Gly Leu Ala Asp Ile Asp Tyr Thr Ser Ile Met Asn Glu His
305                 310                 315                 320

Leu Asn Lys Glu Lys Glu Phe Arg Val Asn Ile Leu Pro Thr Leu
                325                 330                 335

Ser Asn Thr Phe Ser Asn Pro Asn Tyr Ala Lys Val Lys Gly Ser Asp
            340                 345                 350

Glu Asp Ala Lys Met Ile Val Glu Ala Lys Pro Gly His Ala Leu Val
        355                 360                 365

Gly Phe Glu Met Ser Asn Asp Ser Ile Thr Val Leu Lys Val Tyr Glu
    370                 375                 380

Ala Lys Leu Lys Gln Asn Tyr Gln Val Asp Lys Asp Ser Leu Ser Glu
385                 390                 395                 400

Val Ile Tyr Gly Asp Thr Asp Lys Leu Phe Cys Pro Asp Gln Ser Glu
                405                 410                 415

Gln Ile Tyr Tyr Thr Asn Asn Ile Val Phe Pro Asn Glu Tyr Val Ile
            420                 425                 430

Thr Lys Ile Asp Phe Thr Lys Met Lys Thr Leu Arg Tyr Glu Val
        435                 440                 445

Thr Ala Asn Phe Tyr Asp Ser Ser Thr Gly Glu Ile Asp Leu Asn Lys
    450                 455                 460

Lys Lys Val Glu Ser Ser Glu Ala Glu Tyr Arg Thr Leu Ser Ala Asn
465                 470                 475                 480

Asp Asp Gly Val Tyr Met Pro Leu Gly Val Ile Ser Glu Thr Phe Leu
                485                 490                 495

Thr Pro Ile Asn Gly Phe Gly Leu Gln Ala Asp Glu Asn Ser Arg Leu
            500                 505                 510

Ile Thr Leu Thr Cys Lys Ser Tyr Leu Arg Glu Leu Leu Leu Ala Thr
        515                 520                 525

Asp Leu Ser Asn Lys Glu Thr Lys Leu Ile Val Pro Pro Ser Gly Phe
    530                 535                 540

Ile Ser Asn Ile Val Glu Asn Gly Ser Ile Glu Glu Asp Asn Leu Glu
545                 550                 555                 560

Pro Trp Lys Ala Asn Asn Lys Asn Ala Tyr Val Asp His Thr Gly Gly
                565                 570                 575

Val Asn Gly Thr Lys Ala Leu Tyr Val His Lys Asp Gly Gly Phe Ser
            580                 585                 590

Gln Phe Ile Gly Asp Lys Leu Lys Pro Lys Thr Glu Tyr Val Ile Gln
        595                 600                 605

Tyr Thr Val Lys Gly Lys Pro Ser Ile His Leu Lys Asp Glu Asn Thr
    610                 615                 620

Gly Tyr Ile His Tyr Glu Asp Thr Asn Asn Asn Leu Lys Asp Tyr Gln
625                 630                 635                 640

Thr Ile Thr Lys Arg Phe Thr Thr Gly Thr Asp Leu Lys Gly Val Tyr
                645                 650                 655

Leu Ile Leu Lys Ser Gln Asn Gly Asp Glu Ala Trp Gly Asp Lys Phe
            660                 665                 670

Thr Ile Leu Glu Ile Lys Pro Ala Glu Asp Leu Leu Ser Pro Glu Leu
        675                 680                 685
```

-continued

```
Ile Asn Pro Asn Ser Trp Ile Thr Thr Pro Gly Ala Ser Ile Ser Gly
    690             695                 700

Asn Lys Leu Phe Ile Asn Leu Gly Thr Asn Gly Thr Phe Arg Gln Ser
705             710                 715                 720

Leu Ser Leu Asn Ser Tyr Ser Thr Tyr Ser Ile Ser Phe Thr Ala Ser
                725                 730                 735

Gly Pro Phe Asn Val Thr Val Arg Asn Ser Arg Glu Val Leu Phe Glu
                740                 745                 750

Arg Ser Asn Leu Met Ser Ser Thr Ser His Ile Ser Gly Thr Phe Lys
                755                 760                 765

Thr Glu Ser Asn Asn Thr Gly Leu Tyr Val Glu Leu Ser Arg Arg Ser
770                 775                 780

Gly Gly Gly Gly His Ile Ser Phe Glu Asn Val Ser Ile Lys
785                 790                 795
```

<210> SEQ ID NO 7
<211> LENGTH: 809
<212> TYPE: PRT
<213> ORGANISM: Artificial
<220> FEATURE:
<223> OTHER INFORMATION: P021d3_to_2ZEX sequence
<220> FEATURE:
<221> NAME/KEY: MISC_FEATURE
<222> LOCATION: (552)..(688)
<223> OTHER INFORMATION: 2ZEX domain

<400> SEQUENCE: 7

```
Met His His His His His His His His Asn Met Asn Thr
1               5                   10                  15

Lys Leu Asn Ala Arg Ala Leu Pro Ser Phe Ile Asp Tyr Phe Asn Gly
                20                  25                  30

Ile Tyr Gly Phe Ala Thr Gly Ile Lys Asp Ile Met Asn Met Ile Phe
            35                  40                  45

Lys Thr Asp Thr Gly Gly Asn Leu Thr Leu Asp Glu Ile Leu Lys Asn
50                  55                  60

Gln Gln Leu Leu Asn Glu Ile Ser Gly Lys Leu Asp Gly Val Asn Gly
65                  70                  75                  80

Ser Leu Asn Asp Leu Ile Ala Gln Gly Asn Leu Asn Thr Glu Leu Ser
                85                  90                  95

Lys Glu Ile Leu Lys Ile Ala Asn Glu Gln Asn Gln Val Leu Asn Asp
                100                 105                 110

Val Asn Asn Lys Leu Asp Ala Ile Asn Thr Met Leu His Ile Tyr Leu
                115                 120                 125

Pro Lys Ile Thr Ser Met Leu Ser Asp Val Met Lys Gln Asn Tyr Ala
130                 135                 140

Leu Ser Leu Gln Ile Glu Tyr Leu Ser Lys Gln Leu Gln Glu Ile Ser
145                 150                 155                 160

Asp Lys Leu Asp Ile Ile Asn Val Asn Val Leu Ile Asn Ser Thr Leu
                165                 170                 175

Thr Glu Ile Thr Pro Ala Tyr Gln Arg Ile Lys Tyr Val Asn Glu Lys
                180                 185                 190

Phe Glu Glu Leu Thr Phe Ala Thr Glu Ala Pro Phe Val Lys Lys
                195                 200                 205

Asp Ser Ser Pro Ala Asp Ile Leu Asp Glu Leu Thr Glu Leu Thr Glu
                210                 215                 220

Leu Ala Lys Ser Val Thr Lys Asn Asp Val Asp Gly Phe Glu Phe Tyr
225                 230                 235                 240
```

-continued

Leu Asn Thr Phe His Asp Val Met Val Gly Asn Asn Leu Phe Gly Arg
            245                 250                 255

Ser Ala Leu Lys Thr Ala Ser Glu Leu Ile Ala Lys Glu Asn Val Lys
            260                 265                 270

Thr Ser Gly Ser Glu Val Gly Asn Val Tyr Asn Phe Leu Ile Val Leu
            275                 280                 285

Thr Ala Leu Gln Ala Lys Ala Phe Leu Thr Leu Thr Thr Cys Arg Lys
            290                 295                 300

Leu Leu Gly Leu Ala Asp Ile Asp Tyr Thr Ser Ile Met Asn Glu His
305                 310                 315                 320

Leu Asn Lys Glu Lys Glu Phe Arg Val Asn Ile Leu Pro Thr Leu
            325                 330                 335

Ser Asn Thr Phe Ser Asn Pro Asn Tyr Ala Lys Val Lys Gly Ser Asp
            340                 345                 350

Glu Asp Ala Lys Met Ile Val Glu Ala Lys Pro Gly His Ala Leu Val
            355                 360                 365

Gly Phe Glu Met Ser Asn Asp Ser Ile Thr Val Leu Lys Val Tyr Glu
            370                 375                 380

Ala Lys Leu Lys Gln Asn Tyr Gln Val Asp Lys Asp Ser Leu Ser Glu
385                 390                 395                 400

Val Ile Tyr Gly Asp Thr Asp Lys Leu Phe Cys Pro Asp Gln Ser Glu
            405                 410                 415

Gln Ile Tyr Tyr Thr Asn Asn Ile Val Phe Pro Asn Glu Tyr Val Ile
            420                 425                 430

Thr Lys Ile Asp Phe Thr Lys Lys Met Lys Thr Leu Arg Tyr Glu Val
            435                 440                 445

Thr Ala Asn Phe Tyr Asp Ser Ser Thr Gly Glu Ile Asp Leu Asn Lys
            450                 455                 460

Lys Lys Val Glu Ser Ser Glu Ala Glu Tyr Arg Thr Leu Ser Ala Asn
465                 470                 475                 480

Asp Asp Gly Val Tyr Met Pro Leu Gly Val Ile Ser Glu Thr Phe Leu
            485                 490                 495

Thr Pro Ile Asn Gly Phe Gly Leu Gln Ala Asp Glu Asn Ser Arg Leu
            500                 505                 510

Ile Thr Leu Thr Cys Lys Ser Tyr Leu Arg Glu Leu Leu Leu Ala Thr
            515                 520                 525

Asp Leu Ser Asn Lys Glu Thr Lys Leu Ile Val Pro Pro Ser Gly Phe
            530                 535                 540

Ile Ser Asn Ile Val Glu Asn Pro Gly Phe Glu Asp Gly Leu Asp Ser
545                 550                 555                 560

Trp Gln Asp Trp Gln Gln Asp Met Ser Ala Val Pro Glu Ala Ala His
            565                 570                 575

Asn Gly Ala Leu Gly Leu Lys Ile Gly Gly Gly Lys Ala Ala Gly Gly
            580                 585                 590

Gly Gln Asp Ile Pro Leu Lys Pro Asn Thr Thr Tyr Ile Leu Gly Ala
            595                 600                 605

Trp Ala Lys Phe Asp Ser Lys Pro Ala Gly Thr Phe Asp Val Val Val
            610                 615                 620

Gln Tyr His Leu Lys Asp Ala Asn Asn Thr Tyr Val Gln His Ile Leu
625                 630                 635                 640

Asn Phe Asn Glu Thr Asp Trp Thr Tyr Lys Gln Leu Leu Phe Thr Thr
            645                 650                 655

```
Pro Asp Val Phe Gly Ser Thr Pro Gln Leu Ala Leu Trp Lys Gly Asp
            660                 665                 670

Thr Ser Lys Ala Asn Leu Tyr Val Asp Asp Val Tyr Leu Val Glu Val
        675                 680                 685

Lys Pro Ala Glu Asp Leu Leu Ser Pro Glu Leu Ile Asn Pro Asn Ser
    690                 695                 700

Trp Ile Thr Thr Pro Gly Ala Ser Ile Ser Gly Asn Lys Leu Phe Ile
705                 710                 715                 720

Asn Leu Gly Thr Asn Gly Thr Phe Arg Gln Ser Leu Ser Leu Asn Ser
                725                 730                 735

Tyr Ser Thr Tyr Ser Ile Ser Phe Thr Ala Ser Gly Pro Phe Asn Val
            740                 745                 750

Thr Val Arg Asn Ser Arg Glu Val Leu Phe Glu Arg Ser Asn Leu Met
        755                 760                 765

Ser Ser Thr Ser His Ile Ser Gly Thr Phe Lys Thr Glu Ser Asn Asn
    770                 775                 780

Thr Gly Leu Tyr Val Glu Leu Ser Arg Arg Ser Gly Gly Gly His
785                 790                 795                 800

Ile Ser Phe Glu Asn Val Ser Ile Lys
                805

<210> SEQ ID NO 8
<211> LENGTH: 809
<212> TYPE: PRT
<213> ORGANISM: Artificial
<220> FEATURE:
<223> OTHER INFORMATION: P021d3_to2ZEZ sequence
<220> FEATURE:
<221> NAME/KEY: MISC_FEATURE
<222> LOCATION: (552)..(688)
<223> OTHER INFORMATION: 2ZEZ domain

<400> SEQUENCE: 8

Met His His His His His His His His Asn Met Asn Thr
1               5                   10                  15

Lys Leu Asn Ala Arg Ala Leu Pro Ser Phe Ile Asp Tyr Phe Asn Gly
            20                  25                  30

Ile Tyr Gly Phe Ala Thr Gly Ile Lys Asp Ile Met Asn Met Ile Phe
        35                  40                  45

Lys Thr Asp Thr Gly Gly Asn Leu Thr Leu Asp Glu Ile Leu Lys Asn
    50                  55                  60

Gln Gln Leu Leu Asn Glu Ile Ser Gly Lys Leu Asp Gly Val Asn Gly
65                  70                  75                  80

Ser Leu Asn Asp Leu Ile Ala Gln Gly Asn Leu Asn Thr Glu Leu Ser
                85                  90                  95

Lys Glu Ile Leu Lys Ile Ala Asn Glu Gln Asn Gln Val Leu Asn Asp
            100                 105                 110

Val Asn Asn Lys Leu Asp Ala Ile Asn Thr Met Leu His Ile Tyr Leu
        115                 120                 125

Pro Lys Ile Thr Ser Met Leu Ser Asp Val Met Lys Gln Asn Tyr Ala
    130                 135                 140

Leu Ser Leu Gln Ile Glu Tyr Leu Ser Lys Gln Leu Gln Glu Ile Ser
145                 150                 155                 160

Asp Lys Leu Asp Ile Ile Asn Val Asn Val Leu Ile Asn Ser Thr Leu
                165                 170                 175

Thr Glu Ile Thr Pro Ala Tyr Gln Arg Ile Lys Tyr Val Asn Glu Lys
            180                 185                 190
```

```
Phe Glu Glu Leu Thr Phe Ala Thr Glu Ala Ala Pro Phe Val Lys Lys
            195                 200                 205

Asp Ser Ser Pro Ala Asp Ile Leu Asp Glu Leu Thr Glu Leu Thr Glu
    210                 215                 220

Leu Ala Lys Ser Val Thr Lys Asn Asp Val Asp Gly Phe Glu Phe Tyr
225                 230                 235                 240

Leu Asn Thr Phe His Asp Val Met Val Gly Asn Asn Leu Phe Gly Arg
                245                 250                 255

Ser Ala Leu Lys Thr Ala Ser Glu Leu Ile Ala Lys Glu Asn Val Lys
                260                 265                 270

Thr Ser Gly Ser Glu Val Gly Asn Val Tyr Asn Phe Leu Ile Val Leu
            275                 280                 285

Thr Ala Leu Gln Ala Lys Ala Phe Leu Thr Leu Thr Thr Cys Arg Lys
    290                 295                 300

Leu Leu Gly Leu Ala Asp Ile Asp Tyr Thr Ser Ile Met Asn Glu His
305                 310                 315                 320

Leu Asn Lys Glu Lys Glu Phe Arg Val Asn Ile Leu Pro Thr Leu
                325                 330                 335

Ser Asn Thr Phe Ser Asn Pro Asn Tyr Ala Lys Val Lys Gly Ser Asp
                340                 345                 350

Glu Asp Ala Lys Met Ile Val Glu Ala Lys Pro Gly His Ala Leu Val
            355                 360                 365

Gly Phe Glu Met Ser Asn Asp Ser Ile Thr Val Leu Lys Val Tyr Glu
    370                 375                 380

Ala Lys Leu Lys Gln Asn Tyr Gln Val Asp Lys Asp Ser Leu Ser Glu
385                 390                 395                 400

Val Ile Tyr Gly Asp Thr Asp Lys Leu Phe Cys Pro Asp Gln Ser Glu
                405                 410                 415

Gln Ile Tyr Tyr Thr Asn Asn Ile Val Phe Pro Asn Glu Tyr Val Ile
                420                 425                 430

Thr Lys Ile Asp Phe Thr Lys Lys Met Lys Thr Leu Arg Tyr Glu Val
            435                 440                 445

Thr Ala Asn Phe Tyr Asp Ser Ser Thr Gly Glu Ile Asp Leu Asn Lys
    450                 455                 460

Lys Lys Val Glu Ser Ser Glu Ala Glu Tyr Arg Thr Leu Ser Ala Asn
465                 470                 475                 480

Asp Asp Gly Val Tyr Met Pro Leu Gly Val Ile Ser Glu Thr Phe Leu
                485                 490                 495

Thr Pro Ile Asn Gly Phe Gly Leu Gln Ala Asp Glu Asn Ser Arg Leu
            500                 505                 510

Ile Thr Leu Thr Cys Lys Ser Tyr Leu Arg Glu Leu Leu Leu Ala Thr
    515                 520                 525

Asp Leu Ser Asn Lys Glu Thr Lys Leu Ile Val Pro Pro Ser Gly Phe
530                 535                 540

Ile Ser Asn Ile Val Glu Asn Pro Gly Phe Glu Asn Gly Met Asp Gly
545                 550                 555                 560

Trp Pro Asp Trp Gly Tyr Pro Val Ser Ala Val Pro Glu Ala Ala Tyr
                565                 570                 575

Gly Gly Thr Lys Gly Phe Lys Leu Ser Gly Gly Lys Gln Ala Gly Met
            580                 585                 590

Gly Gln Lys Val Ala Leu Lys Pro Asn Thr Thr Tyr Ile Leu Gly Ala
    595                 600                 605
```

```
Trp Gly Lys Phe Thr Ala Lys Pro Gly Thr Tyr Cys Asp Val Ile Val
            610                 615                 620

Gln Tyr His Leu Lys Asp Ala Asn Asn Thr Tyr Val Gln Asn Ile Leu
625                 630                 635                 640

Arg Phe Thr Glu Thr Asp Trp Thr Tyr Lys Gln Val Val Phe Thr Thr
                645                 650                 655

Pro Asp Ala Phe Gly Ser Asp Pro Glu Phe Val Leu Trp Lys Asp Asp
                660                 665                 670

Ala Ser Asn Ala Asp Phe Tyr Ala Asp Asn Ile Thr Leu Val Glu Val
                675                 680                 685

Lys Pro Ala Glu Asp Leu Leu Ser Pro Glu Leu Ile Asn Pro Asn Ser
690                 695                 700

Trp Ile Thr Thr Pro Gly Ala Ser Ile Ser Gly Asn Lys Leu Phe Ile
705                 710                 715                 720

Asn Leu Gly Thr Asn Gly Thr Phe Arg Gln Ser Leu Ser Leu Asn Ser
                725                 730                 735

Tyr Ser Tyr Ser Ile Ser Phe Thr Ala Ser Gly Pro Phe Asn Val
                740                 745                 750

Thr Val Arg Asn Ser Arg Glu Val Leu Phe Glu Arg Ser Asn Leu Met
                755                 760                 765

Ser Ser Thr Ser His Ile Ser Gly Thr Phe Lys Thr Glu Ser Asn Asn
770                 775                 780

Thr Gly Leu Tyr Val Glu Leu Ser Arg Arg Ser Gly Gly Gly His
785                 790                 795                 800

Ile Ser Phe Glu Asn Val Ser Ile Lys
                805

<210> SEQ ID NO 9
<211> LENGTH: 833
<212> TYPE: PRT
<213> ORGANISM: Artificial
<220> FEATURE:
<223> OTHER INFORMATION: P021d3_to_1OFE sequence
<220> FEATURE:
<221> NAME/KEY: MISC_FEATURE
<222> LOCATION: (552)..(712)
<223> OTHER INFORMATION: 1OFE domain

<400> SEQUENCE: 9

Met His His His His His His His His Asn Met Asn Asn Thr
1               5                   10                  15

Lys Leu Asn Ala Arg Ala Leu Pro Ser Phe Ile Asp Tyr Phe Asn Gly
                20                  25                  30

Ile Tyr Gly Phe Ala Thr Gly Ile Lys Asp Ile Met Asn Met Ile Phe
            35                  40                  45

Lys Thr Asp Thr Gly Gly Asn Leu Thr Leu Asp Glu Ile Leu Lys Asn
50                  55                  60

Gln Gln Leu Leu Asn Glu Ile Ser Gly Lys Leu Asp Gly Val Asn Gly
65                  70                  75                  80

Ser Leu Asn Asp Leu Ile Ala Gln Gly Asn Leu Asn Thr Glu Leu Ser
                85                  90                  95

Lys Glu Ile Leu Lys Ile Ala Asn Glu Gln Asn Gln Val Leu Asn Asp
                100                 105                 110

Val Asn Asn Lys Leu Asp Ala Ile Asn Thr Met Leu His Ile Tyr Leu
            115                 120                 125

Pro Lys Ile Thr Ser Met Leu Ser Asp Val Met Lys Gln Asn Tyr Ala
            130                 135                 140
```

```
Leu Ser Leu Gln Ile Glu Tyr Leu Ser Lys Gln Leu Gln Glu Ile Ser
145                 150                 155                 160

Asp Lys Leu Asp Ile Ile Asn Val Asn Val Leu Ile Asn Ser Thr Leu
            165                 170                 175

Thr Glu Ile Thr Pro Ala Tyr Gln Arg Ile Lys Tyr Val Asn Glu Lys
        180                 185                 190

Phe Glu Glu Leu Thr Phe Ala Thr Glu Ala Ala Pro Phe Val Lys Lys
    195                 200                 205

Asp Ser Ser Pro Ala Asp Ile Leu Asp Glu Leu Thr Glu Leu Thr Glu
210                 215                 220

Leu Ala Lys Ser Val Thr Lys Asn Asp Val Asp Gly Phe Glu Phe Tyr
225                 230                 235                 240

Leu Asn Thr Phe His Asp Val Met Val Gly Asn Asn Leu Phe Gly Arg
                245                 250                 255

Ser Ala Leu Lys Thr Ala Ser Glu Leu Ile Ala Lys Glu Asn Val Lys
            260                 265                 270

Thr Ser Gly Ser Glu Val Gly Asn Val Tyr Asn Phe Leu Ile Val Leu
        275                 280                 285

Thr Ala Leu Gln Ala Lys Ala Phe Leu Thr Leu Thr Thr Cys Arg Lys
290                 295                 300

Leu Leu Gly Leu Ala Asp Ile Asp Tyr Thr Ser Ile Met Asn Glu His
305                 310                 315                 320

Leu Asn Lys Glu Lys Glu Phe Arg Val Asn Ile Leu Pro Thr Leu
                325                 330                 335

Ser Asn Thr Phe Ser Asn Pro Asn Tyr Ala Lys Val Lys Gly Ser Asp
            340                 345                 350

Glu Asp Ala Lys Met Ile Val Glu Ala Lys Pro Gly His Ala Leu Val
            355                 360                 365

Gly Phe Glu Met Ser Asn Asp Ser Ile Thr Val Leu Lys Val Tyr Glu
    370                 375                 380

Ala Lys Leu Lys Gln Asn Tyr Gln Val Asp Lys Asp Ser Leu Ser Glu
385                 390                 395                 400

Val Ile Tyr Gly Asp Thr Asp Lys Leu Phe Cys Pro Asp Gln Ser Glu
                405                 410                 415

Gln Ile Tyr Tyr Thr Asn Asn Ile Val Phe Pro Asn Glu Tyr Val Ile
            420                 425                 430

Thr Lys Ile Asp Phe Thr Lys Lys Met Lys Thr Leu Arg Tyr Glu Val
            435                 440                 445

Thr Ala Asn Phe Tyr Asp Ser Ser Thr Gly Glu Ile Asp Leu Asn Lys
450                 455                 460

Lys Lys Val Glu Ser Ser Glu Ala Glu Tyr Arg Thr Leu Ser Ala Asn
465                 470                 475                 480

Asp Asp Gly Val Tyr Met Pro Leu Gly Val Ile Ser Glu Thr Phe Leu
                485                 490                 495

Thr Pro Ile Asn Gly Phe Gly Leu Gln Ala Asp Glu Asn Ser Arg Leu
            500                 505                 510

Ile Thr Leu Thr Cys Lys Ser Tyr Leu Arg Glu Leu Leu Ala Thr
            515                 520                 525

Asp Leu Ser Asn Lys Glu Thr Lys Leu Ile Val Pro Pro Ser Gly Phe
            530                 535                 540

Ile Ser Asn Ile Val Glu Asn Asp Phe Ser Ser Pro Glu Glu Val Lys
545                 550                 555                 560
```

```
Asn Trp Trp Asn Ser Gly Thr Trp Gln Ala Glu Phe Gly Ser Pro Asp
                565                 570                 575

Ile Glu Trp Asn Gly Glu Val Gly Asn Gly Ala Leu Gln Leu Asn Val
            580                 585                 590

Lys Leu Pro Gly Lys Ser Asp Trp Glu Glu Val Arg Val Ala Arg Lys
        595                 600                 605

Phe Glu Arg Leu Ser Glu Cys Glu Ile Leu Glu Tyr Asp Ile Tyr Ile
    610                 615                 620

Pro Asn Val Glu Gly Leu Lys Gly Arg Leu Arg Pro Tyr Ala Val Leu
625                 630                 635                 640

Asn Pro Gly Trp Val Lys Ile Gly Leu Asp Met Asn Asn Ala Asn Val
                645                 650                 655

Glu Ser Ala Glu Ile Ile Thr Phe Gly Gly Lys Glu Tyr Arg Arg Phe
            660                 665                 670

His Val Arg Ile Glu Phe Asp Arg Thr Ala Gly Val Lys Glu Leu His
        675                 680                 685

Ile Gly Val Val Gly Asp His Leu Arg Tyr Asp Gly Pro Ile Phe Ile
    690                 695                 700

Asp Asn Val Arg Leu Tyr Lys Arg Lys Pro Ala Glu Asp Leu Leu Ser
705                 710                 715                 720

Pro Glu Leu Ile Asn Pro Asn Ser Trp Ile Thr Thr Pro Gly Ala Ser
                725                 730                 735

Ile Ser Gly Asn Lys Leu Phe Ile Asn Leu Gly Thr Asn Gly Thr Phe
            740                 745                 750

Arg Gln Ser Leu Ser Leu Asn Ser Tyr Ser Thr Tyr Ser Ile Ser Phe
        755                 760                 765

Thr Ala Ser Gly Pro Phe Asn Val Thr Val Arg Asn Ser Arg Glu Val
    770                 775                 780

Leu Phe Glu Arg Ser Asn Leu Met Ser Ser Thr Ser His Ile Ser Gly
785                 790                 795                 800

Thr Phe Lys Thr Glu Ser Asn Asn Thr Gly Leu Tyr Val Glu Leu Ser
                805                 810                 815

Arg Arg Ser Gly Gly Gly Gly His Ile Ser Phe Glu Asn Val Ser Ile
            820                 825                 830

Lys

<210> SEQ ID NO 10
<211> LENGTH: 846
<212> TYPE: PRT
<213> ORGANISM: Artificial
<220> FEATURE:
<223> OTHER INFORMATION: P021d3_to_1PMH sequence
<220> FEATURE:
<221> NAME/KEY: MISC_FEATURE
<222> LOCATION: (552)..(725)
<223> OTHER INFORMATION: 1PMH domain

<400> SEQUENCE: 10

Met His His His His His His His His Asn Met Asn Asn Thr
1               5                   10                  15

Lys Leu Asn Ala Arg Ala Leu Pro Ser Phe Ile Asp Tyr Phe Asn Gly
            20                  25                  30

Ile Tyr Gly Phe Ala Thr Gly Ile Lys Asp Ile Met Asn Met Ile Phe
        35                  40                  45

Lys Thr Asp Thr Gly Gly Asn Leu Thr Leu Asp Glu Ile Leu Lys Asn
    50                  55                  60
```

-continued

Gln Gln Leu Leu Asn Glu Ile Ser Gly Lys Leu Asp Gly Val Asn Gly
65                  70                  75                  80

Ser Leu Asn Asp Leu Ile Ala Gln Gly Asn Leu Asn Thr Glu Leu Ser
            85                  90                  95

Lys Glu Ile Leu Lys Ile Ala Asn Glu Gln Asn Gln Val Leu Asn Asp
            100                 105                 110

Val Asn Asn Lys Leu Asp Ala Ile Asn Thr Met Leu His Ile Tyr Leu
        115                 120                 125

Pro Lys Ile Thr Ser Met Leu Ser Asp Val Met Lys Gln Asn Tyr Ala
    130                 135                 140

Leu Ser Leu Gln Ile Glu Tyr Leu Ser Lys Gln Leu Gln Glu Ile Ser
145                 150                 155                 160

Asp Lys Leu Asp Ile Ile Asn Val Asn Val Leu Ile Asn Ser Thr Leu
                165                 170                 175

Thr Glu Ile Thr Pro Ala Tyr Gln Arg Ile Lys Tyr Val Asn Glu Lys
            180                 185                 190

Phe Glu Glu Leu Thr Phe Ala Thr Glu Ala Ala Pro Phe Val Lys Lys
        195                 200                 205

Asp Ser Ser Pro Ala Asp Ile Leu Asp Glu Leu Thr Glu Leu Thr Glu
    210                 215                 220

Leu Ala Lys Ser Val Thr Lys Asn Asp Val Asp Gly Phe Glu Phe Tyr
225                 230                 235                 240

Leu Asn Thr Phe His Asp Val Met Val Gly Asn Leu Phe Gly Arg
                245                 250                 255

Ser Ala Leu Lys Thr Ala Ser Glu Leu Ile Ala Lys Gly Asn Val Lys
            260                 265                 270

Thr Ser Gly Ser Glu Val Gly Asn Val Tyr Asn Phe Leu Ile Val Leu
        275                 280                 285

Thr Ala Leu Gln Ala Lys Ala Phe Leu Thr Leu Thr Thr Cys Arg Lys
    290                 295                 300

Leu Leu Gly Leu Ala Asp Ile Asp Tyr Thr Ser Ile Met Asn Glu His
305                 310                 315                 320

Leu Asn Lys Glu Lys Glu Phe Arg Val Asn Ile Leu Pro Thr Leu
                325                 330                 335

Ser Asn Thr Phe Ser Asn Pro Asn Tyr Ala Lys Val Lys Gly Ser Asp
            340                 345                 350

Glu Asp Ala Lys Met Ile Val Glu Ala Lys Pro Gly His Ala Leu Val
        355                 360                 365

Gly Phe Glu Met Ser Asn Asp Ser Ile Thr Val Leu Lys Val Tyr Glu
    370                 375                 380

Ala Lys Leu Lys Gln Asn Tyr Gln Val Asp Lys Asp Ser Leu Ser Glu
385                 390                 395                 400

Val Ile Tyr Gly Asp Thr Asp Lys Leu Phe Cys Pro Asp Gln Ser Glu
                405                 410                 415

Gln Ile Tyr Tyr Thr Asn Asn Ile Val Phe Pro Asn Glu Tyr Val Ile
            420                 425                 430

Thr Lys Ile Asp Phe Thr Lys Lys Met Lys Thr Leu Arg Tyr Glu Val
        435                 440                 445

Thr Ala Asn Phe Tyr Asp Ser Ser Thr Gly Glu Ile Asp Leu Asn Lys
    450                 455                 460

Lys Lys Val Glu Ser Ser Glu Ala Glu Tyr Arg Thr Leu Ser Ala Asn
465                 470                 475                 480

Asp Asp Gly Val Tyr Met Pro Leu Gly Val Ile Ser Glu Thr Phe Leu

```
                    485                 490                 495
Thr Pro Ile Asn Gly Phe Gly Leu Gln Ala Asp Glu Asn Ser Arg Leu
                500                 505                 510

Ile Thr Leu Thr Cys Lys Ser Tyr Leu Arg Glu Leu Leu Leu Ala Thr
            515                 520                 525

Asp Leu Ser Asn Lys Glu Thr Lys Leu Ile Val Pro Pro Ser Gly Phe
    530                 535                 540

Ile Ser Asn Ile Val Glu Asn Asp Phe Glu Asp Gly Thr Val Met Ser
545                 550                 555                 560

Phe Gly Glu Ala Trp Gly Asp Ser Leu Lys Cys Ile Lys Lys Val Ser
                565                 570                 575

Val Ser Gln Asp Leu Gln Arg Pro Gly Asn Lys Tyr Ala Leu Arg Leu
            580                 585                 590

Asp Val Glu Phe Asn Pro Asn Asn Gly Trp Asp Gln Gly Asp Leu Gly
    595                 600                 605

Thr Trp Ile Gly Gly Val Val Glu Gly Gln Phe Asp Phe Thr Gly Tyr
610                 615                 620

Lys Ser Val Glu Phe Glu Met Phe Ile Pro Tyr Asp Glu Phe Ser Lys
625                 630                 635                 640

Ser Gln Gly Gly Phe Ala Tyr Lys Val Val Ile Asn Asp Gly Trp Lys
                645                 650                 655

Glu Leu Gly Ser Glu Phe Asn Ile Thr Ala Asn Ala Gly Lys Lys Val
            660                 665                 670

Lys Ile Asn Gly Lys Asp Tyr Thr Val Ile His Lys Ala Phe Ala Ile
    675                 680                 685

Pro Glu Asp Phe Arg Thr Lys Lys Arg Ala Gln Leu Val Phe Gln Phe
690                 695                 700

Ala Gly Gln Asn Ser Asn Tyr Lys Gly Pro Ile Tyr Leu Asp Asn Val
705                 710                 715                 720

Arg Ile Arg Pro Glu Lys Pro Ala Glu Asp Leu Leu Ser Pro Glu Leu
                725                 730                 735

Ile Asn Pro Asn Ser Trp Ile Thr Thr Pro Gly Ala Ser Ile Ser Gly
            740                 745                 750

Asn Lys Leu Phe Ile Asn Leu Gly Thr Asn Gly Thr Phe Arg Gln Ser
    755                 760                 765

Leu Ser Leu Asn Ser Tyr Ser Thr Tyr Ser Ile Ser Phe Thr Ala Ser
770                 775                 780

Gly Pro Phe Asn Val Thr Val Arg Asn Ser Arg Glu Val Leu Phe Glu
785                 790                 795                 800

Arg Ser Asn Leu Met Ser Ser Thr Ser His Ile Ser Gly Thr Phe Lys
                805                 810                 815

Thr Glu Ser Asn Asn Thr Gly Leu Tyr Val Glu Leu Ser Arg Arg Ser
            820                 825                 830

Gly Gly Gly Gly His Ile Ser Phe Glu Asn Val Ser Ile Lys
    835                 840                 845

<210> SEQ ID NO 11
<211> LENGTH: 784
<212> TYPE: PRT
<213> ORGANISM: Artificial
<220> FEATURE:
<223> OTHER INFORMATION: P021_to_2BGP sequence
<220> FEATURE:
<221> NAME/KEY: MISC_FEATURE
<222> LOCATION: (552)..(663)
<223> OTHER INFORMATION: 2BGP domain
```

<400> SEQUENCE: 11

Met His His His His His His His His Asn Met Asn Asn Thr
1               5                   10                  15

Lys Leu Asn Ala Arg Ala Leu Pro Ser Phe Ile Asp Tyr Phe Asn Gly
            20                  25                  30

Ile Tyr Gly Phe Ala Thr Gly Ile Lys Asp Ile Met Asn Met Ile Phe
            35                  40                  45

Lys Thr Asp Thr Gly Gly Asn Leu Thr Leu Asp Glu Ile Leu Lys Asn
50                  55                  60

Gln Gln Leu Leu Asn Glu Ile Ser Gly Lys Leu Asp Gly Val Asn Gly
65                  70                  75                  80

Ser Leu Asn Asp Leu Ile Ala Gln Gly Asn Leu Asn Thr Glu Leu Ser
                85                  90                  95

Lys Glu Ile Leu Lys Ile Ala Asn Glu Gln Asn Gln Val Leu Asn Asp
                100                 105                 110

Val Asn Asn Lys Leu Asp Ala Ile Asn Thr Met Leu His Ile Tyr Leu
            115                 120                 125

Pro Lys Ile Thr Ser Met Leu Ser Asp Val Met Lys Gln Asn Tyr Ala
            130                 135                 140

Leu Ser Leu Gln Ile Glu Tyr Leu Ser Lys Gln Leu Gln Glu Ile Ser
145                 150                 155                 160

Asp Lys Leu Asp Ile Ile Asn Val Asn Val Leu Ile Asn Ser Thr Leu
                165                 170                 175

Thr Glu Ile Thr Pro Ala Tyr Gln Arg Ile Lys Tyr Val Asn Glu Lys
                180                 185                 190

Phe Glu Glu Leu Thr Phe Ala Thr Glu Ala Ala Pro Phe Val Lys Lys
            195                 200                 205

Asp Ser Ser Pro Ala Asp Ile Leu Asp Glu Leu Thr Glu Leu Thr Glu
            210                 215                 220

Leu Ala Lys Ser Val Thr Lys Asn Asp Val Asp Gly Phe Glu Phe Tyr
225                 230                 235                 240

Leu Asn Thr Phe His Asp Val Met Val Gly Asn Asn Leu Phe Gly Arg
                245                 250                 255

Ser Ala Leu Lys Thr Ala Ser Glu Leu Ile Ala Lys Glu Asn Val Lys
                260                 265                 270

Thr Ser Gly Ser Glu Val Gly Asn Val Tyr Asn Phe Leu Ile Val Leu
            275                 280                 285

Thr Ala Leu Gln Ala Lys Ala Phe Leu Thr Leu Thr Thr Cys Arg Lys
290                 295                 300

Leu Leu Gly Leu Ala Asp Ile Asp Tyr Thr Ser Ile Met Asn Glu His
305                 310                 315                 320

Leu Asn Lys Glu Lys Glu Phe Arg Val Asn Ile Leu Pro Thr Leu
                325                 330                 335

Ser Asn Thr Phe Ser Asn Pro Asn Tyr Ala Lys Val Lys Gly Ser Asp
            340                 345                 350

Glu Asp Ala Lys Met Ile Val Glu Ala Lys Pro Gly His Ala Leu Val
            355                 360                 365

Gly Phe Glu Met Ser Asn Asp Ser Ile Thr Val Leu Lys Val Tyr Glu
            370                 375                 380

Ala Lys Leu Lys Gln Asn Tyr Gln Val Asp Lys Asp Ser Leu Ser Glu
385                 390                 395                 400

Val Ile Tyr Gly Asp Thr Asp Lys Leu Phe Cys Pro Asp Gln Ser Glu

```
            405                 410                 415
Gln Ile Tyr Tyr Thr Asn Asn Ile Val Phe Pro Asn Glu Tyr Val Ile
            420                 425                 430

Thr Lys Ile Asp Phe Thr Lys Met Lys Thr Leu Arg Tyr Glu Val
        435                 440                 445

Thr Ala Asn Phe Tyr Asp Ser Ser Thr Gly Glu Ile Asp Leu Asn Lys
        450                 455                 460

Lys Lys Val Glu Ser Ser Glu Ala Glu Tyr Arg Thr Leu Ser Ala Asn
465                 470                 475                 480

Asp Asp Gly Val Tyr Met Pro Leu Gly Val Ile Ser Glu Thr Phe Leu
                    485                 490                 495

Thr Pro Ile Asn Gly Phe Gly Leu Gln Ala Asp Glu Asn Ser Arg Leu
            500                 505                 510

Ile Thr Leu Thr Cys Lys Ser Tyr Leu Arg Glu Leu Leu Leu Ala Thr
            515                 520                 525

Asp Leu Ser Asn Lys Glu Thr Lys Leu Ile Val Pro Pro Ser Gly Phe
        530                 535                 540

Ile Ser Asn Ile Val Glu Asn Thr Ala Ala Ser Ala Ser Ile Thr Ala
545                 550                 555                 560

Pro Ala Gln Leu Val Gly Asn Val Gly Glu Leu Gln Gly Ala Gly Ser
                    565                 570                 575

Ala Val Ile Trp Asn Val Asp Val Pro Val Thr Gly Glu Tyr Arg Ile
                580                 585                 590

Asn Leu Thr Trp Ser Ser Pro Tyr Ser Ser Lys Val Asn Thr Leu Val
            595                 600                 605

Met Asp Gly Thr Ala Leu Ser Tyr Ala Phe Ala Glu Ala Thr Val Pro
        610                 615                 620

Val Thr Tyr Val Gln Thr Lys Thr Leu Ser Ala Gly Asn His Ser Phe
625                 630                 635                 640

Gly Val Arg Val Gly Ser Ser Asp Trp Gly Tyr Met Asn Val His Ser
                    645                 650                 655

Leu Lys Leu Glu Leu Leu Gly Lys Pro Ala Glu Asp Leu Leu Ser Pro
                660                 665                 670

Glu Leu Ile Asn Pro Asn Ser Trp Ile Thr Thr Pro Gly Ala Ser Ile
            675                 680                 685

Ser Gly Asn Lys Leu Phe Ile Asn Leu Gly Thr Asn Gly Thr Phe Arg
        690                 695                 700

Gln Ser Leu Ser Leu Asn Ser Tyr Ser Thr Tyr Ser Ile Ser Phe Thr
705                 710                 715                 720

Ala Ser Gly Pro Phe Asn Val Thr Val Arg Asn Ser Arg Glu Val Leu
                    725                 730                 735

Phe Glu Arg Ser Asn Leu Met Ser Ser Thr Ser His Ile Ser Gly Thr
                740                 745                 750

Phe Lys Thr Glu Ser Asn Asn Thr Gly Leu Tyr Val Glu Leu Ser Arg
            755                 760                 765

Arg Ser Gly Gly Gly Gly His Ile Ser Phe Glu Asn Val Ser Ile Lys
        770                 775                 780

<210> SEQ ID NO 12
<211> LENGTH: 807
<212> TYPE: PRT
<213> ORGANISM: Artificial
<220> FEATURE:
<223> OTHER INFORMATION: P021_to_GP21 sequence
<220> FEATURE:
```

```
<221> NAME/KEY: MISC_FEATURE
<222> LOCATION: (552)..(686)
<223> OTHER INFORMATION: GP21 domain

<400> SEQUENCE: 12
```

| | | | | | | | | | | | | | | |
|---|---|---|---|---|---|---|---|---|---|---|---|---|---|---|
| Met | His | His | His | His | His | His | His | His | His | Asn | Met | Asn | Asn | Thr |
| 1 | | | | 5 | | | | | 10 | | | | | 15 |
| Lys | Leu | Asn | Ala | Arg | Ala | Leu | Pro | Ser | Phe | Ile | Asp | Tyr | Phe | Asn | Gly |
| | | | 20 | | | | | 25 | | | | | 30 | | |
| Ile | Tyr | Gly | Phe | Ala | Thr | Gly | Ile | Lys | Asp | Ile | Met | Asn | Met | Ile | Phe |
| | | 35 | | | | | 40 | | | | | 45 | | | |
| Lys | Thr | Asp | Thr | Gly | Gly | Asn | Leu | Thr | Leu | Asp | Glu | Ile | Leu | Lys | Asn |
| 50 | | | | | 55 | | | | | 60 | | | | | |
| Gln | Gln | Leu | Leu | Asn | Glu | Ile | Ser | Gly | Lys | Leu | Asp | Gly | Val | Asn | Gly |
| 65 | | | | | 70 | | | | | 75 | | | | | 80 |
| Ser | Leu | Asn | Asp | Leu | Ile | Ala | Gln | Gly | Asn | Leu | Asn | Thr | Glu | Leu | Ser |
| | | | | 85 | | | | | 90 | | | | | 95 | |
| Lys | Glu | Ile | Leu | Lys | Ile | Ala | Asn | Glu | Gln | Asn | Gln | Val | Leu | Asn | Asp |
| | | | 100 | | | | | 105 | | | | | 110 | | |
| Val | Asn | Asn | Lys | Leu | Asp | Ala | Ile | Asn | Thr | Met | Leu | His | Ile | Tyr | Leu |
| | | 115 | | | | | 120 | | | | | 125 | | | |
| Pro | Lys | Ile | Thr | Ser | Met | Leu | Ser | Asp | Val | Met | Lys | Gln | Asn | Tyr | Ala |
| | 130 | | | | | 135 | | | | | 140 | | | | |
| Leu | Ser | Leu | Gln | Ile | Glu | Tyr | Leu | Ser | Lys | Gln | Leu | Gln | Glu | Ile | Ser |
| 145 | | | | | 150 | | | | | 155 | | | | | 160 |
| Asp | Lys | Leu | Asp | Ile | Ile | Asn | Val | Asn | Val | Leu | Ile | Asn | Ser | Thr | Leu |
| | | | | 165 | | | | | 170 | | | | | 175 | |
| Thr | Glu | Ile | Thr | Pro | Ala | Tyr | Gln | Arg | Ile | Lys | Tyr | Val | Asn | Glu | Lys |
| | | | 180 | | | | | 185 | | | | | 190 | | |
| Phe | Glu | Glu | Leu | Thr | Phe | Ala | Thr | Glu | Ala | Ala | Pro | Phe | Val | Lys | Lys |
| | | 195 | | | | | 200 | | | | | 205 | | | |
| Asp | Ser | Ser | Pro | Ala | Asp | Ile | Leu | Asp | Glu | Leu | Thr | Glu | Leu | Thr | Glu |
| | 210 | | | | | 215 | | | | | 220 | | | | |
| Leu | Ala | Lys | Ser | Val | Thr | Lys | Asn | Asp | Val | Asp | Gly | Phe | Glu | Phe | Tyr |
| 225 | | | | | 230 | | | | | 235 | | | | | 240 |
| Leu | Asn | Thr | Phe | His | Asp | Val | Met | Val | Gly | Asn | Asn | Leu | Phe | Gly | Arg |
| | | | | 245 | | | | | 250 | | | | | 255 | |
| Ser | Ala | Leu | Lys | Thr | Ala | Ser | Glu | Leu | Ile | Ala | Lys | Glu | Asn | Val | Lys |
| | | | 260 | | | | | 265 | | | | | 270 | | |
| Thr | Ser | Gly | Ser | Glu | Val | Gly | Asn | Val | Tyr | Asn | Phe | Leu | Ile | Val | Leu |
| | | 275 | | | | | 280 | | | | | 285 | | | |
| Thr | Ala | Leu | Gln | Ala | Lys | Ala | Phe | Leu | Thr | Leu | Thr | Thr | Cys | Arg | Lys |
| | 290 | | | | | 295 | | | | | 300 | | | | |
| Leu | Leu | Gly | Leu | Ala | Asp | Ile | Asp | Tyr | Thr | Ser | Ile | Met | Asn | Glu | His |
| 305 | | | | | 310 | | | | | 315 | | | | | 320 |
| Leu | Asn | Lys | Glu | Lys | Glu | Phe | Arg | Val | Asn | Ile | Leu | Pro | Thr | Leu |
| | | | | 325 | | | | | 330 | | | | | 335 |
| Ser | Asn | Thr | Phe | Ser | Asn | Pro | Asn | Tyr | Ala | Lys | Val | Lys | Gly | Ser | Asp |
| | | | 340 | | | | | 345 | | | | | 350 | | |
| Glu | Asp | Ala | Lys | Met | Ile | Val | Glu | Ala | Lys | Pro | Gly | His | Ala | Leu | Val |
| | | 355 | | | | | 360 | | | | | 365 | | | |
| Gly | Phe | Glu | Met | Ser | Asn | Asp | Ser | Ile | Thr | Val | Leu | Lys | Val | Tyr | Glu |
| | 370 | | | | | 375 | | | | | 380 | | | | |
| Ala | Lys | Leu | Lys | Gln | Asn | Tyr | Gln | Val | Asp | Lys | Asp | Ser | Leu | Ser | Glu |

-continued

```
385                 390                 395                 400
Val Ile Tyr Gly Asp Thr Asp Lys Leu Phe Cys Pro Asp Gln Ser Glu
                405                 410                 415
Gln Ile Tyr Tyr Thr Asn Asn Ile Val Phe Pro Asn Glu Tyr Val Ile
                420                 425                 430
Thr Lys Ile Asp Phe Thr Lys Lys Met Lys Thr Leu Arg Tyr Glu Val
                435                 440                 445
Thr Ala Asn Phe Tyr Asp Ser Ser Thr Gly Glu Ile Asp Leu Asn Lys
            450                 455                 460
Lys Lys Val Glu Ser Ser Glu Ala Glu Tyr Arg Thr Leu Ser Ala Asn
465                 470                 475                 480
Asp Asp Gly Val Tyr Met Pro Leu Gly Val Ile Ser Glu Thr Phe Leu
                485                 490                 495
Thr Pro Ile Asn Gly Phe Gly Leu Gln Ala Asp Glu Asn Ser Arg Leu
            500                 505                 510
Ile Thr Leu Thr Cys Lys Ser Tyr Leu Arg Glu Leu Leu Leu Ala Thr
                515                 520                 525
Asp Leu Ser Asn Lys Glu Thr Lys Leu Ile Val Pro Pro Ser Gly Phe
            530                 535                 540
Ile Ser Asn Ile Val Glu Asn Pro Ser Phe Glu Arg Gly Thr Glu Gly
545                 550                 555                 560
Tyr Thr Gly Trp Ser Gly Ile Ala Thr Val Val Thr Leu Gln Val Pro
                565                 570                 575
His Leu Gly Thr Lys Ala Ala Lys Leu Ala Ala Gly Ser Ala Gly
                580                 585                 590
Val Gly Gln Lys Ile Ser Phe Lys Lys Asp Arg Ser Tyr Lys Ile Gly
            595                 600                 605
Ile Trp Ala Lys Gln Asp Pro Asn Thr Thr Ile Gln Ser Thr Asp Asn
            610                 615                 620
Thr Lys Phe Arg Val Ala Asp Gly Asn Gly Leu Ile Ala Ser Lys Ala
625                 630                 635                 640
Tyr Gly Pro Phe Thr Ser Asn Trp Gln Glu Val Ser Trp Thr Trp Lys
                645                 650                 655
Ala Thr Lys Asp Val Leu Ala Asp Val Gln Phe Thr Ala Phe Leu Ser
                660                 665                 670
Ala Gly Ala Met Tyr Phe Asp Asp Phe Tyr Val Asp Val Lys Pro
            675                 680                 685
Ala Glu Asp Leu Leu Ser Pro Glu Leu Ile Asn Pro Asn Ser Trp Ile
            690                 695                 700
Thr Thr Pro Gly Ala Ser Ile Ser Gly Asn Lys Leu Phe Ile Asn Leu
705                 710                 715                 720
Gly Thr Asn Gly Thr Phe Arg Gln Ser Leu Ser Leu Asn Ser Tyr Ser
                725                 730                 735
Thr Tyr Ser Ile Ser Phe Thr Ala Ser Gly Pro Phe Asn Val Thr Val
            740                 745                 750
Arg Asn Ser Arg Glu Val Leu Phe Glu Arg Ser Asn Leu Met Ser Ser
                755                 760                 765
Thr Ser His Ile Ser Gly Thr Phe Lys Thr Glu Ser Asn Asn Thr Gly
            770                 775                 780
Leu Tyr Val Glu Leu Ser Arg Arg Ser Gly Gly Gly His Ile Ser
785                 790                 795                 800
Phe Glu Asn Val Ser Ile Lys
            805
```

<210> SEQ ID NO 13
<211> LENGTH: 812
<212> TYPE: PRT
<213> ORGANISM: Artificial
<220> FEATURE:
<223> OTHER INFORMATION: P021_to_CENC sequence
<220> FEATURE:
<221> NAME/KEY: MISC_FEATURE
<222> LOCATION: (552)..(691)
<223> OTHER INFORMATION: CenC domain

<400> SEQUENCE: 13

```
Met His His His His His His His His Asn Met Asn Thr
1               5                   10                  15

Lys Leu Asn Ala Arg Ala Leu Pro Ser Phe Ile Asp Tyr Phe Asn Gly
            20                  25                  30

Ile Tyr Gly Phe Ala Thr Gly Ile Lys Asp Ile Met Asn Met Ile Phe
        35                  40                  45

Lys Thr Asp Thr Gly Gly Asn Leu Thr Leu Asp Glu Ile Leu Lys Asn
    50                  55                  60

Gln Gln Leu Leu Asn Glu Ile Ser Gly Lys Leu Asp Gly Val Asn Gly
65                  70                  75                  80

Ser Leu Asn Asp Leu Ile Ala Gln Gly Asn Leu Asn Thr Glu Leu Ser
                85                  90                  95

Lys Glu Ile Leu Lys Ile Ala Asn Glu Gln Asn Gln Val Leu Asn Asp
            100                 105                 110

Val Asn Asn Lys Leu Asp Ala Ile Asn Thr Met Leu His Ile Tyr Leu
        115                 120                 125

Pro Lys Ile Thr Ser Met Leu Ser Asp Val Met Lys Gln Asn Tyr Ala
    130                 135                 140

Leu Ser Leu Gln Ile Glu Tyr Leu Ser Lys Gln Leu Gln Glu Ile Ser
145                 150                 155                 160

Asp Lys Leu Asp Ile Ile Asn Val Asn Val Leu Ile Asn Ser Thr Leu
                165                 170                 175

Thr Glu Ile Thr Pro Ala Tyr Gln Arg Ile Lys Tyr Val Asn Glu Lys
            180                 185                 190

Phe Glu Glu Leu Thr Phe Ala Thr Glu Ala Ala Pro Phe Val Lys Lys
        195                 200                 205

Asp Ser Ser Pro Ala Asp Ile Leu Asp Glu Leu Thr Glu Leu Thr Glu
    210                 215                 220

Leu Ala Lys Ser Val Thr Lys Asn Asp Val Asp Gly Phe Glu Phe Tyr
225                 230                 235                 240

Leu Asn Thr Phe His Asp Val Met Val Gly Asn Asn Leu Phe Gly Arg
                245                 250                 255

Ser Ala Leu Lys Thr Ala Ser Glu Leu Ile Ala Lys Glu Asn Val Lys
            260                 265                 270

Thr Ser Gly Ser Glu Val Gly Asn Val Tyr Asn Phe Leu Ile Val Leu
        275                 280                 285

Thr Ala Leu Gln Ala Lys Ala Phe Leu Thr Leu Thr Thr Cys Arg Lys
    290                 295                 300

Leu Leu Gly Leu Ala Asp Ile Asp Tyr Thr Ser Ile Met Asn Glu His
305                 310                 315                 320

Leu Asn Lys Glu Lys Glu Glu Phe Arg Val Asn Ile Leu Pro Thr Leu
                325                 330                 335

Ser Asn Thr Phe Ser Asn Pro Asn Tyr Ala Lys Val Lys Gly Ser Asp
```

```
            340                 345                 350
Glu Asp Ala Lys Met Ile Val Glu Ala Lys Pro Gly His Ala Leu Val
            355                 360                 365
Gly Phe Glu Met Ser Asn Asp Ser Ile Thr Val Leu Lys Val Tyr Glu
            370                 375                 380
Ala Lys Leu Lys Gln Asn Tyr Gln Val Asp Lys Asp Ser Leu Ser Glu
385                 390                 395                 400
Val Ile Tyr Gly Asp Thr Asp Lys Leu Phe Cys Pro Asp Gln Ser Glu
            405                 410                 415
Gln Ile Tyr Tyr Thr Asn Asn Ile Val Phe Pro Asn Glu Tyr Val Ile
            420                 425                 430
Thr Lys Ile Asp Phe Thr Lys Lys Met Lys Thr Leu Arg Tyr Glu Val
            435                 440                 445
Thr Ala Asn Phe Tyr Asp Ser Ser Thr Gly Glu Ile Asp Leu Asn Lys
            450                 455                 460
Lys Lys Val Glu Ser Ser Glu Ala Glu Tyr Arg Thr Leu Ser Ala Asn
465                 470                 475                 480
Asp Asp Gly Val Tyr Met Pro Leu Gly Val Ile Ser Glu Thr Phe Leu
            485                 490                 495
Thr Pro Ile Asn Gly Phe Gly Leu Gln Ala Asp Glu Asn Ser Arg Leu
            500                 505                 510
Ile Thr Leu Thr Cys Lys Ser Tyr Leu Arg Glu Leu Leu Leu Ala Thr
            515                 520                 525
Asp Leu Ser Asn Lys Glu Thr Lys Leu Ile Val Pro Pro Ser Gly Phe
            530                 535                 540
Ile Ser Asn Ile Val Glu Asn Pro Gly Leu Glu Asp Gly Ile Asn Asn
545                 550                 555                 560
Trp Gln Ala Trp Gly Glu Gly Phe Thr Ala Ala Ser Asp Met Ser His
                565                 570                 575
Thr Gly Ser Ala Ser Leu Lys Val Leu Leu Asn Asn Gly Gly Arg Gln
            580                 585                 590
Val Val Ala Leu Gln Pro Gly Lys Ser Tyr Lys Leu Gly Val Trp Gly
            595                 600                 605
Lys Thr Ala Gly Thr Gly Thr Gly Thr Gln Thr Ala Thr Val Met Ile
            610                 615                 620
Asn Tyr Lys Lys Pro Glu Asp Asp Ser Ser His Thr Tyr Gly Ser Phe
625                 630                 635                 640
Gln Phe Gly Pro Asp Asn Ser Glu Phe Thr Tyr Lys Glu Ile Thr Phe
                645                 650                 655
Glu Thr Pro Asp Asp Met Ala Gln Glu Trp Gly Thr Gln Phe Val Ser
                660                 665                 670
Ile Trp Ser Glu Gly Ala Asp Gln Val Tyr Leu Asp Asp Phe Thr Leu
            675                 680                 685
Ser Glu Val Lys Pro Ala Glu Asp Leu Leu Ser Pro Glu Leu Ile Asn
            690                 695                 700
Pro Asn Ser Trp Ile Thr Thr Pro Gly Ala Ser Ile Ser Gly Asn Lys
705                 710                 715                 720
Leu Phe Ile Asn Leu Gly Thr Asn Gly Thr Phe Arg Gln Ser Leu Ser
                725                 730                 735
Leu Asn Ser Tyr Ser Thr Tyr Ser Ile Ser Phe Thr Ala Ser Gly Pro
                740                 745                 750
Phe Asn Val Thr Val Arg Asn Ser Arg Glu Val Leu Phe Glu Arg Ser
                755                 760                 765
```

```
Asn Leu Met Ser Ser Thr Ser His Ile Ser Gly Thr Phe Lys Thr Glu
    770                 775                 780

Ser Asn Asn Thr Gly Leu Tyr Val Glu Leu Ser Arg Arg Ser Gly Gly
785                 790                 795                 800

Gly Gly His Ile Ser Phe Glu Asn Val Ser Ile Lys
            805                 810

<210> SEQ ID NO 14
<211> LENGTH: 805
<212> TYPE: PRT
<213> ORGANISM: Artificial
<220> FEATURE:
<223> OTHER INFORMATION: P021_to_PsHGF7 sequence
<220> FEATURE:
<221> NAME/KEY: MISC_FEATURE
<222> LOCATION: (552)..(684)
<223> OTHER INFORMATION: PSHGF7 domain

<400> SEQUENCE: 14

Met His His His His His His His His Asn Met Asn Asn Thr
1               5                   10                  15

Lys Leu Asn Ala Arg Ala Leu Pro Ser Phe Ile Asp Tyr Phe Asn Gly
            20                  25                  30

Ile Tyr Gly Phe Ala Thr Gly Ile Lys Asp Ile Met Asn Met Ile Phe
        35                  40                  45

Lys Thr Asp Thr Gly Gly Asn Leu Thr Leu Asp Glu Ile Leu Lys Asn
    50                  55                  60

Gln Gln Leu Leu Asn Glu Ile Ser Gly Lys Leu Asp Gly Val Asn Gly
65                  70                  75                  80

Ser Leu Asn Asp Leu Ile Ala Gln Gly Asn Leu Asn Thr Glu Leu Ser
                85                  90                  95

Lys Glu Ile Leu Lys Ile Ala Asn Glu Gln Asn Gln Val Leu Asn Asp
            100                 105                 110

Val Asn Asn Lys Leu Asp Ala Ile Asn Thr Met Leu His Ile Tyr Leu
        115                 120                 125

Pro Lys Ile Thr Ser Met Leu Ser Asp Val Met Lys Gln Asn Tyr Ala
    130                 135                 140

Leu Ser Leu Gln Ile Glu Tyr Leu Ser Lys Gln Leu Gln Glu Ile Ser
145                 150                 155                 160

Asp Lys Leu Asp Ile Ile Asn Val Asn Val Leu Ile Asn Ser Thr Leu
                165                 170                 175

Thr Glu Ile Thr Pro Ala Tyr Gln Arg Ile Lys Tyr Val Asn Glu Lys
            180                 185                 190

Phe Glu Glu Leu Thr Phe Ala Thr Glu Ala Ala Pro Phe Val Lys Lys
        195                 200                 205

Asp Ser Ser Pro Ala Asp Ile Leu Asp Glu Leu Thr Glu Leu Thr Glu
    210                 215                 220

Leu Ala Lys Ser Val Thr Lys Asn Asp Val Asp Gly Phe Glu Phe Tyr
225                 230                 235                 240

Leu Asn Thr Phe His Asp Val Met Val Gly Asn Asn Leu Phe Gly Arg
                245                 250                 255

Ser Ala Leu Lys Thr Ala Ser Glu Leu Ile Ala Lys Glu Asn Val Lys
            260                 265                 270

Thr Ser Gly Ser Glu Val Gly Asn Val Tyr Asn Phe Leu Ile Val Leu
        275                 280                 285

Thr Ala Leu Gln Ala Lys Ala Phe Leu Thr Leu Thr Thr Cys Arg Lys
```

```
                290                 295                 300
Leu Leu Gly Leu Ala Asp Ile Asp Tyr Thr Ser Ile Met Asn Glu His
305                 310                 315                 320

Leu Asn Lys Glu Lys Glu Phe Arg Val Asn Ile Leu Pro Thr Leu
                325                 330                 335

Ser Asn Thr Phe Ser Asn Pro Asn Tyr Ala Lys Val Lys Gly Ser Asp
                340                 345                 350

Glu Asp Ala Lys Met Ile Val Glu Ala Lys Pro Gly His Ala Leu Val
                355                 360                 365

Gly Phe Glu Met Ser Asn Asp Ser Ile Thr Val Leu Lys Val Tyr Glu
                370                 375                 380

Ala Lys Leu Lys Gln Asn Tyr Gln Val Asp Lys Asp Ser Leu Ser Glu
385                 390                 395                 400

Val Ile Tyr Gly Asp Thr Asp Lys Leu Phe Cys Pro Asp Gln Ser Glu
                405                 410                 415

Gln Ile Tyr Tyr Thr Asn Asn Ile Val Phe Pro Asn Glu Tyr Val Ile
                420                 425                 430

Thr Lys Ile Asp Phe Thr Lys Lys Met Lys Thr Leu Arg Tyr Glu Val
                435                 440                 445

Thr Ala Asn Phe Tyr Asp Ser Ser Thr Gly Glu Ile Asp Leu Asn Lys
                450                 455                 460

Lys Lys Val Glu Ser Ser Glu Ala Glu Tyr Arg Thr Leu Ser Ala Asn
465                 470                 475                 480

Asp Asp Gly Val Tyr Met Pro Leu Gly Val Ile Ser Glu Thr Phe Leu
                485                 490                 495

Thr Pro Ile Asn Gly Phe Gly Leu Gln Ala Asp Glu Asn Ser Arg Leu
                500                 505                 510

Ile Thr Leu Thr Cys Lys Ser Tyr Leu Arg Glu Leu Leu Leu Ala Thr
                515                 520                 525

Asp Leu Ser Asn Lys Glu Thr Lys Leu Ile Val Pro Pro Ser Gly Phe
                530                 535                 540

Ile Ser Asn Ile Val Glu Asn Pro Gly Phe Glu Asp Asn Leu Ala Ser
545                 550                 555                 560

Trp Thr Asn Trp Gly Asn Thr Ser Ser Val Thr Ser Pro Ala Phe Ala
                565                 570                 575

Gly Ala Lys Ala Ala Arg Ile Ala Ser Gly Glu Gly Ala Gly Gln
                580                 585                 590

Ile Ile Pro Gly Ile Pro Ser Gly Thr Thr Tyr Val Leu Ser Gly His
                595                 600                 605

Gly Ser Val Ser Ala Gly Thr Asp Thr Ala Ile Val Gly Val Asp Cys
                610                 615                 620

Leu Asp Ala Asn Asn Val Leu Ala Lys Asn Thr Leu Arg Phe Asn
625                 630                 635                 640

Gln Thr Leu Tyr Glu Phe Lys Ser Thr Ala Phe Thr Thr Val Pro Gly
                645                 650                 655

Thr Ala Lys Leu Gln Val Tyr Ile Tyr Lys Asn Ala Asp Ser Gly Ala
                660                 665                 670

Asn Ala Phe Leu Asp Asp Leu Ser Leu Val Glu Val Lys Pro Ala Glu
                675                 680                 685

Asp Leu Leu Ser Pro Glu Leu Ile Asn Pro Asn Ser Trp Ile Thr Thr
                690                 695                 700

Pro Gly Ala Ser Ile Ser Gly Asn Lys Leu Phe Ile Asn Leu Gly Thr
705                 710                 715                 720
```

```
Asn Gly Thr Phe Arg Gln Ser Leu Ser Leu Asn Ser Tyr Ser Thr Tyr
            725                 730                 735

Ser Ile Ser Phe Thr Ala Ser Gly Pro Phe Asn Val Thr Val Arg Asn
            740                 745                 750

Ser Arg Glu Val Leu Phe Glu Arg Ser Asn Leu Met Ser Ser Thr Ser
            755                 760                 765

His Ile Ser Gly Thr Phe Lys Thr Glu Ser Asn Asn Thr Gly Leu Tyr
            770                 775                 780

Val Glu Leu Ser Arg Arg Ser Gly Gly Gly His Ile Ser Phe Glu
785                 790                 795                 800

Asn Val Ser Ile Lys
            805

<210> SEQ ID NO 15
<211> LENGTH: 818
<212> TYPE: PRT
<213> ORGANISM: Artificial
<220> FEATURE:
<223> OTHER INFORMATION: P021_to_1WKY sequence
<220> FEATURE:
<221> NAME/KEY: MISC_FEATURE
<222> LOCATION: (552)..(697)
<223> OTHER INFORMATION: 1WKY domain

<400> SEQUENCE: 15

Met His His His His His His His Asn Met Asn Asn Thr
1               5                   10                  15

Lys Leu Asn Ala Arg Ala Leu Pro Ser Phe Ile Asp Tyr Phe Asn Gly
            20                  25                  30

Ile Tyr Gly Phe Ala Thr Gly Ile Lys Asp Ile Met Asn Met Ile Phe
            35                  40                  45

Lys Thr Asp Thr Gly Gly Asn Leu Thr Leu Asp Glu Ile Leu Lys Asn
        50                  55                  60

Gln Gln Leu Leu Asn Glu Ile Ser Gly Lys Leu Asp Gly Val Asn Gly
65                  70                  75                  80

Ser Leu Asn Asp Leu Ile Ala Gln Gly Asn Leu Asn Thr Glu Leu Ser
            85                  90                  95

Lys Glu Ile Leu Lys Ile Ala Asn Glu Gln Asn Gln Val Leu Asn Asp
            100                 105                 110

Val Asn Asn Lys Leu Asp Ala Ile Asn Thr Met Leu His Ile Tyr Leu
        115                 120                 125

Pro Lys Ile Thr Ser Met Leu Ser Asp Val Met Lys Gln Asn Tyr Ala
        130                 135                 140

Leu Ser Leu Gln Ile Glu Tyr Leu Ser Lys Gln Leu Gln Glu Ile Ser
145                 150                 155                 160

Asp Lys Leu Asp Ile Ile Asn Val Asn Val Leu Ile Asn Ser Thr Leu
            165                 170                 175

Thr Glu Ile Thr Pro Ala Tyr Gln Arg Ile Lys Tyr Val Asn Glu Lys
            180                 185                 190

Phe Glu Glu Leu Thr Phe Ala Thr Glu Ala Ala Pro Phe Val Lys Lys
        195                 200                 205

Asp Ser Ser Pro Ala Asp Ile Leu Asp Glu Leu Thr Glu Leu Thr Glu
        210                 215                 220

Leu Ala Lys Ser Val Thr Lys Asn Asp Val Asp Gly Phe Glu Phe Tyr
225                 230                 235                 240

Leu Asn Thr Phe His Asp Val Met Val Gly Asn Asn Leu Phe Gly Arg
```

```
                245                 250                 255
Ser Ala Leu Lys Thr Ala Ser Glu Leu Ile Ala Lys Glu Asn Val Lys
            260                 265                 270

Thr Ser Gly Ser Glu Val Gly Asn Val Tyr Asn Phe Leu Ile Val Leu
        275                 280                 285

Thr Ala Leu Gln Ala Lys Ala Phe Leu Thr Leu Thr Thr Cys Arg Lys
    290                 295                 300

Leu Leu Gly Leu Ala Asp Ile Asp Tyr Thr Ser Ile Met Asn Glu His
305                 310                 315                 320

Leu Asn Lys Glu Lys Glu Phe Arg Val Asn Ile Leu Pro Thr Leu
            325                 330                 335

Ser Asn Thr Phe Ser Asn Pro Asn Tyr Ala Lys Val Lys Gly Ser Asp
            340                 345                 350

Glu Asp Ala Lys Met Ile Val Glu Ala Lys Pro Gly His Ala Leu Val
            355                 360                 365

Gly Phe Glu Met Ser Asn Asp Ser Ile Thr Val Leu Lys Val Tyr Glu
        370                 375                 380

Ala Lys Leu Lys Gln Asn Tyr Gln Val Asp Lys Asp Ser Leu Ser Glu
385                 390                 395                 400

Val Ile Tyr Gly Asp Thr Asp Lys Leu Phe Cys Pro Asp Gln Ser Glu
                405                 410                 415

Gln Ile Tyr Tyr Thr Asn Asn Ile Val Phe Pro Asn Glu Tyr Val Ile
            420                 425                 430

Thr Lys Ile Asp Phe Thr Lys Lys Met Lys Thr Leu Arg Tyr Glu Val
            435                 440                 445

Thr Ala Asn Phe Tyr Asp Ser Ser Thr Gly Glu Ile Asp Leu Asn Lys
    450                 455                 460

Lys Lys Val Glu Ser Ser Glu Ala Glu Tyr Arg Thr Leu Ser Ala Asn
465                 470                 475                 480

Asp Asp Gly Val Tyr Met Pro Leu Gly Val Ile Ser Glu Thr Phe Leu
                485                 490                 495

Thr Pro Ile Asn Gly Phe Gly Leu Gln Ala Asp Glu Asn Ser Arg Leu
            500                 505                 510

Ile Thr Leu Thr Cys Lys Ser Tyr Leu Arg Glu Leu Leu Leu Ala Thr
            515                 520                 525

Asp Leu Ser Asn Lys Glu Thr Lys Leu Ile Val Pro Pro Ser Gly Phe
    530                 535                 540

Ile Ser Asn Ile Val Glu Asn Asp Phe Glu Glu Ser Thr Gln Gly Trp
545                 550                 555                 560

Thr Gly Ser Ser Leu Ser Arg Gly Pro Trp Thr Val Thr Glu Trp Ser
                565                 570                 575

Ser Lys Gly Asn His Ser Leu Lys Ala Asp Ile Gln Met Ser Ser Asn
            580                 585                 590

Ser Gln His Tyr Leu His Val Ile Gln Asn Arg Ser Leu Gln Gln Asn
            595                 600                 605

Ser Arg Ile Gln Ala Thr Val Lys His Ala Asn Trp Gly Ser Val Gly
        610                 615                 620

Asn Gly Met Thr Ala Arg Leu Tyr Val Lys Thr Gly His Gly Tyr Thr
625                 630                 635                 640

Trp Tyr Ser Gly Ser Phe Val Pro Ile Asn Gly Ser Ser Gly Thr Thr
                645                 650                 655

Leu Ser Leu Asp Leu Ser Asn Val Gln Asn Leu Ser Gln Val Arg Glu
            660                 665                 670
```

-continued

Ile Gly Val Gln Phe Gln Ser Glu Ser Asn Ser Ser Gly Gln Thr Ser
            675                 680                 685

Ile Tyr Ile Asp Asn Val Ile Val Glu Lys Pro Ala Glu Asp Leu Leu
690                 695                 700

Ser Pro Glu Leu Ile Asn Pro Asn Ser Trp Ile Thr Thr Pro Gly Ala
705                 710                 715                 720

Ser Ile Ser Gly Asn Lys Leu Phe Ile Asn Leu Gly Thr Asn Gly Thr
            725                 730                 735

Phe Arg Gln Ser Leu Ser Leu Asn Ser Tyr Ser Thr Tyr Ser Ile Ser
            740                 745                 750

Phe Thr Ala Ser Gly Pro Phe Asn Val Thr Val Arg Asn Ser Arg Glu
            755                 760                 765

Val Leu Phe Glu Arg Ser Asn Leu Met Ser Ser Thr Ser His Ile Ser
770                 775                 780

Gly Thr Phe Lys Thr Glu Ser Asn Asn Thr Gly Leu Tyr Val Glu Leu
785                 790                 795                 800

Ser Arg Arg Ser Gly Gly Gly His Ile Ser Phe Glu Asn Val Ser
            805                 810                 815

Ile Lys

<210> SEQ ID NO 16
<211> LENGTH: 800
<212> TYPE: PRT
<213> ORGANISM: Artificial
<220> FEATURE:
<223> OTHER INFORMATION: Vip3Ad3_to_2ZEX sequence
<220> FEATURE:
<221> NAME/KEY: MISC_FEATURE
<222> LOCATION: (542)..(678)
<223> OTHER INFORMATION: 2ZEX domain

<400> SEQUENCE: 16

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
            85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
            165                 170                 175

Lys Tyr Val Asn Glu Lys Phe Glu Glu Leu Thr Phe Ala Thr Glu Thr
            180                 185                 190

```
Ser Ser Lys Val Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
                260                 265                 270

Asn Phe Leu Ile Val Leu Thr Ala Leu Gln Ala Gln Ala Phe Leu Thr
                275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Phe Arg Val
305                 310                 315                 320

Asn Ile Leu Pro Thr Leu Ser Asn Thr Phe Ser Pro Asn Tyr Ala
                325                 330                 335

Lys Val Lys Gly Ser Asp Glu Asp Ala Lys Met Ile Val Glu Ala Lys
                340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
        435                 440                 445

Glu Ile Asp Leu Asn Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Pro Gly Phe
    530                 535                 540

Glu Asp Gly Leu Asp Ser Trp Gln Asp Trp Gln Asp Met Ser Ala
545                 550                 555                 560

Val Pro Glu Ala Ala His Asn Gly Ala Leu Gly Leu Lys Ile Gly Gly
                565                 570                 575

Gly Lys Ala Ala Gly Gly Gln Asp Ile Pro Leu Lys Pro Asn Thr
                580                 585                 590

Thr Tyr Ile Leu Gly Ala Trp Ala Lys Phe Asp Ser Lys Pro Ala Gly
        595                 600                 605
```

-continued

```
Thr Phe Asp Val Val Gln Tyr His Leu Lys Asp Ala Asn Asn Thr
610             615                 620

Tyr Val Gln His Ile Leu Asn Phe Asn Glu Thr Asp Trp Thr Tyr Lys
625                 630                 635                 640

Gln Leu Leu Phe Thr Thr Pro Asp Val Phe Gly Ser Thr Pro Gln Leu
                645                 650                 655

Ala Leu Trp Lys Gly Asp Thr Ser Lys Ala Asn Leu Tyr Val Asp Asp
                660                 665                 670

Val Tyr Leu Val Glu Val Ser Pro Ser Glu Lys Leu Leu Ser Pro Glu
                675                 680                 685

Leu Ile Asn Thr Asn Asn Trp Thr Ser Thr Gly Ser Thr Asn Ile Ser
690                 695                 700

Gly Asn Thr Leu Thr Leu Tyr Gln Gly Gly Arg Gly Ile Leu Lys Gln
705                 710                 715                 720

Asn Leu Gln Leu Asp Ser Phe Ser Thr Tyr Arg Val Tyr Phe Ser Val
                725                 730                 735

Ser Gly Asp Ala Asn Val Arg Ile Arg Asn Ser Arg Glu Val Leu Phe
                740                 745                 750

Glu Lys Arg Tyr Met Ser Gly Ala Lys Asp Val Ser Glu Met Phe Thr
                755                 760                 765

Thr Lys Phe Glu Lys Asp Asn Phe Tyr Ile Glu Leu Ser Gln Gly Asn
770                 775                 780

Asn Leu Tyr Gly Gly Pro Ile Val His Phe Tyr Asp Val Ser Ile Lys
785                 790                 795                 800
```

<210> SEQ ID NO 17
<211> LENGTH: 800
<212> TYPE: PRT
<213> ORGANISM: Artificial
<220> FEATURE:
<223> OTHER INFORMATION: Vip3Ad3_to_2ZEZ sequence
<220> FEATURE:
<221> NAME/KEY: MISC_FEATURE
<222> LOCATION: (542)..(678)
<223> OTHER INFORMATION: 2ZEZ domain

<400> SEQUENCE: 17

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asp Leu Thr Leu
            35                  40                  45

Asp Glu Ile Leu Lys Asn Gln Gln Leu Leu Asn Asp Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
                100                 105                 110

Met Leu Arg Val Tyr Leu Pro Lys Ile Thr Ser Met Leu Ser Asp Val
            115                 120                 125

Met Lys Gln Asn Tyr Ala Leu Ser Leu Gln Ile Glu Tyr Leu Ser Lys
        130                 135                 140

Gln Leu Gln Glu Ile Ser Asp Lys Leu Asp Ile Ile Asn Val Asn Val
145                 150                 155                 160
```

```
Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Gln Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Pro Gly Phe
    530                 535                 540

Glu Asn Gly Met Asp Gly Trp Pro Asp Trp Gly Tyr Pro Val Ser Ala
545                 550                 555                 560

Val Pro Glu Ala Ala Tyr Gly Gly Thr Lys Gly Phe Lys Leu Ser Gly
                565                 570                 575
```

-continued

```
Gly Lys Gln Ala Gly Met Gly Gln Lys Val Ala Leu Lys Pro Asn Thr
            580                 585                 590

Thr Tyr Ile Leu Gly Ala Trp Gly Lys Phe Thr Ala Lys Pro Gly Thr
        595                 600                 605

Tyr Cys Asp Val Ile Val Gln Tyr His Leu Lys Asp Ala Asn Asn Thr
    610                 615                 620

Tyr Val Gln Asn Ile Leu Arg Phe Thr Glu Thr Asp Trp Thr Tyr Lys
625                 630                 635                 640

Gln Val Val Phe Thr Thr Pro Asp Ala Phe Gly Ser Asp Pro Glu Phe
                645                 650                 655

Val Leu Trp Lys Asp Asp Ala Ser Asn Ala Asp Phe Tyr Ala Asp Asn
            660                 665                 670

Ile Thr Leu Val Glu Val Ser Pro Ser Glu Lys Leu Leu Ser Pro Glu
        675                 680                 685

Leu Ile Asn Thr Asn Asn Trp Thr Ser Thr Gly Ser Thr Asn Ile Ser
    690                 695                 700

Gly Asn Thr Leu Thr Leu Tyr Gln Gly Gly Arg Gly Ile Leu Lys Gln
705                 710                 715                 720

Asn Leu Gln Leu Asp Ser Phe Ser Thr Tyr Arg Val Tyr Phe Ser Val
                725                 730                 735

Ser Gly Asp Ala Asn Val Arg Ile Arg Asn Ser Arg Glu Val Leu Phe
            740                 745                 750

Glu Lys Arg Tyr Met Ser Gly Ala Lys Asp Val Ser Glu Met Phe Thr
        755                 760                 765

Thr Lys Phe Glu Lys Asp Asn Phe Tyr Ile Glu Leu Ser Gln Gly Asn
    770                 775                 780

Asn Leu Tyr Gly Gly Pro Ile Val His Phe Tyr Asp Val Ser Ile Lys
785                 790                 795                 800

<210> SEQ ID NO 18
<211> LENGTH: 824
<212> TYPE: PRT
<213> ORGANISM: Artificial
<220> FEATURE:
<223> OTHER INFORMATION: Vip3Ad3_to_1OFE sequence
<220> FEATURE:
<221> NAME/KEY: MISC_FEATURE
<222> LOCATION: (542)..(702)
<223> OTHER INFORMATION: OFE domain
<220> FEATURE:
<221> NAME/KEY: MISC_FEATURE
<222> LOCATION: (542)..(702)
<223> OTHER INFORMATION: 1OFE domain

<400> SEQUENCE: 18

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
```

```
                100                 105                 110
Met Leu Arg Val Tyr Leu Pro Lys Ile Thr Ser Met Leu Ser Asp Val
            115                 120                 125

Met Lys Gln Asn Tyr Ala Leu Ser Leu Gln Ile Glu Tyr Leu Ser Lys
130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
            165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
            195                 200                 205

Leu Thr Glu Leu Thr Glu Leu Ala Lys Ser Val Thr Lys Asn Asp Val
210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
            245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Gln Ala Phe Leu Thr
            275                 280                 285

Leu Thr Thr Cys Arg Lys Leu Leu Gly Leu Ala Asp Ile Asp Tyr Thr
            290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
            325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
            355                 360                 365

Val Leu Lys Val Tyr Glu Ala Lys Leu Lys Gln Asn Tyr Gln Val Asp
            370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
            405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
            435                 440                 445

Glu Ile Asp Leu Asn Lys Lys Val Glu Ser Ser Glu Ala Glu Tyr
            450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
            485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
            515                 520                 525
```

```
Val Pro Pro Ser Gly Phe Ile Ser Asn Ile Val Glu Asn Asp Phe Ser
        530                 535                 540

Ser Pro Glu Glu Val Lys Asn Trp Trp Asn Ser Gly Thr Trp Gln Ala
545                 550                 555                 560

Glu Phe Gly Ser Pro Asp Ile Glu Trp Asn Gly Glu Val Gly Asn Gly
                565                 570                 575

Ala Leu Gln Leu Asn Val Lys Leu Pro Gly Lys Ser Asp Trp Glu Glu
            580                 585                 590

Val Arg Val Ala Arg Lys Phe Glu Arg Leu Ser Glu Cys Glu Ile Leu
        595                 600                 605

Glu Tyr Asp Ile Tyr Ile Pro Asn Val Glu Gly Leu Lys Gly Arg Leu
    610                 615                 620

Arg Pro Tyr Ala Val Leu Asn Pro Gly Trp Val Lys Ile Gly Leu Asp
625                 630                 635                 640

Met Asn Asn Ala Asn Val Glu Ser Ala Glu Ile Ile Thr Phe Gly Gly
                645                 650                 655

Lys Glu Tyr Arg Arg Phe His Val Arg Ile Glu Phe Asp Arg Thr Ala
            660                 665                 670

Gly Val Lys Glu Leu His Ile Gly Val Val Gly Asp His Leu Arg Tyr
        675                 680                 685

Asp Gly Pro Ile Phe Ile Asp Asn Val Arg Leu Tyr Lys Arg Ser Pro
    690                 695                 700

Ser Glu Lys Leu Leu Ser Pro Glu Leu Ile Asn Thr Asn Asn Trp Thr
705                 710                 715                 720

Ser Thr Gly Ser Thr Asn Ile Ser Gly Asn Thr Leu Thr Leu Tyr Gln
                725                 730                 735

Gly Gly Arg Gly Ile Leu Lys Gln Asn Leu Gln Leu Asp Ser Phe Ser
            740                 745                 750

Thr Tyr Arg Val Tyr Phe Ser Val Ser Gly Asp Ala Asn Val Arg Ile
        755                 760                 765

Arg Asn Ser Arg Glu Val Leu Phe Glu Lys Arg Tyr Met Ser Gly Ala
    770                 775                 780

Lys Asp Val Ser Glu Met Phe Thr Thr Lys Phe Glu Lys Asp Asn Phe
785                 790                 795                 800

Tyr Ile Glu Leu Ser Gln Gly Asn Asn Leu Tyr Gly Gly Pro Ile Val
                805                 810                 815

His Phe Tyr Asp Val Ser Ile Lys
            820

<210> SEQ ID NO 19
<211> LENGTH: 837
<212> TYPE: PRT
<213> ORGANISM: Artificial
<220> FEATURE:
<223> OTHER INFORMATION: Vip3Ad3_to_1PMH sequence
<220> FEATURE:
<221> NAME/KEY: MISC_FEATURE
<222> LOCATION: (542)..(715)
<223> OTHER INFORMATION: 1PMH domain

<400> SEQUENCE: 19

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
```

```
                35                  40                  45
Asp Glu Ile Leu Lys Asn Gln Gln Leu Leu Asn Asp Ile Ser Gly Lys
                50                  55                  60
Leu Asp Gly Val Asn Gly Ser Leu Asn Asp Leu Ile Ala Gln Gly Asn
 65                 70                  75                  80
Leu Asn Thr Glu Leu Ser Lys Glu Ile Leu Lys Ile Ala Asn Glu Gln
                85                  90                  95
Asn Gln Val Leu Asn Asp Val Asn Asn Lys Leu Asp Ala Ile Asn Thr
                100                 105                 110
Met Leu Arg Val Tyr Leu Pro Lys Ile Thr Ser Met Leu Ser Asp Val
                115                 120                 125
Met Lys Gln Asn Tyr Ala Leu Ser Leu Gln Ile Glu Tyr Leu Ser Lys
                130                 135                 140
Gln Leu Gln Glu Ile Ser Asp Lys Leu Asp Ile Ile Asn Val Asn Val
145                 150                 155                 160
Leu Ile Asn Ser Thr Leu Thr Glu Ile Thr Pro Ala Tyr Gln Arg Ile
                165                 170                 175
Lys Tyr Val Asn Glu Lys Phe Glu Glu Leu Thr Phe Ala Thr Glu Thr
                180                 185                 190
Ser Ser Lys Val Lys Lys Asp Gly Ser Pro Ala Asp Ile Leu Asp Glu
                195                 200                 205
Leu Thr Glu Leu Thr Glu Leu Ala Lys Ser Val Thr Lys Asn Asp Val
                210                 215                 220
Asp Gly Phe Glu Phe Tyr Leu Asn Thr Phe His Asp Val Met Val Gly
225                 230                 235                 240
Asn Asn Leu Phe Gly Arg Ser Ala Leu Lys Thr Ala Ser Glu Leu Ile
                245                 250                 255
Thr Lys Glu Asn Val Lys Thr Ser Gly Ser Glu Val Gly Asn Val Tyr
                260                 265                 270
Asn Phe Leu Ile Val Leu Thr Ala Leu Gln Ala Gln Ala Phe Leu Thr
                275                 280                 285
Leu Thr Thr Cys Arg Lys Leu Leu Gly Leu Ala Asp Ile Asp Tyr Thr
                290                 295                 300
Ser Ile Met Asn Glu His Leu Asn Lys Glu Lys Glu Glu Phe Arg Val
305                 310                 315                 320
Asn Ile Leu Pro Thr Leu Ser Asn Thr Phe Ser Asn Pro Asn Tyr Ala
                325                 330                 335
Lys Val Lys Gly Ser Asp Glu Asp Ala Lys Met Ile Val Glu Ala Lys
                340                 345                 350
Pro Gly His Ala Leu Ile Gly Phe Glu Ile Ser Asn Asp Ser Ile Thr
                355                 360                 365
Val Leu Lys Val Tyr Glu Ala Lys Leu Lys Gln Asn Tyr Gln Val Asp
                370                 375                 380
Lys Asp Ser Leu Ser Glu Val Ile Tyr Gly Asp Met Asp Lys Leu Leu
385                 390                 395                 400
Cys Pro Asp Gln Ser Glu Gln Ile Tyr Tyr Thr Asn Asn Ile Val Phe
                405                 410                 415
Pro Asn Glu Tyr Val Ile Thr Lys Ile Asp Phe Thr Lys Lys Met Lys
                420                 425                 430
Thr Leu Arg Tyr Glu Val Thr Ala Asn Phe Tyr Asp Ser Ser Thr Gly
                435                 440                 445
Glu Ile Asp Leu Asn Lys Lys Lys Val Glu Ser Ser Glu Ala Glu Tyr
                450                 455                 460
```

Arg Thr Leu Ser Ala Asn Asp Gly Val Tyr Met Pro Leu Gly Val
465                 470                 475                 480

Ile Ser Glu Thr Phe Leu Thr Pro Ile Asn Gly Phe Gly Leu Gln Ala
            485                 490                 495

Asp Glu Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
            515                 520                 525

Val Pro Pro Ser Gly Phe Ile Ser Asn Ile Val Glu Asn Asp Phe Glu
530                 535                 540

Asp Gly Thr Val Met Ser Phe Gly Glu Ala Trp Gly Asp Ser Leu Lys
545                 550                 555                 560

Cys Ile Lys Lys Val Ser Val Ser Gln Asp Leu Gln Arg Pro Gly Asn
                565                 570                 575

Lys Tyr Ala Leu Arg Leu Asp Val Glu Phe Asn Pro Asn Asn Gly Trp
            580                 585                 590

Asp Gln Gly Asp Leu Gly Thr Trp Ile Gly Val Glu Gly Gln
            595                 600                 605

Phe Asp Phe Thr Gly Tyr Lys Ser Val Glu Phe Glu Met Phe Ile Pro
610                 615                 620

Tyr Asp Glu Phe Ser Lys Ser Gln Gly Gly Phe Ala Tyr Lys Val Val
625                 630                 635                 640

Ile Asn Asp Gly Trp Lys Glu Leu Gly Ser Glu Phe Asn Ile Thr Ala
                645                 650                 655

Asn Ala Gly Lys Lys Val Lys Ile Asn Gly Lys Asp Tyr Thr Val Ile
            660                 665                 670

His Lys Ala Phe Ala Ile Pro Glu Asp Phe Arg Thr Lys Lys Arg Ala
            675                 680                 685

Gln Leu Val Phe Gln Phe Ala Gly Gln Asn Ser Asn Tyr Lys Gly Pro
            690                 695                 700

Ile Tyr Leu Asp Asn Val Arg Ile Arg Pro Glu Ser Pro Ser Glu Lys
705                 710                 715                 720

Leu Leu Ser Pro Glu Leu Ile Asn Thr Asn Trp Thr Ser Thr Gly
                725                 730                 735

Ser Thr Asn Ile Ser Gly Asn Thr Leu Thr Leu Tyr Gln Gly Gly Arg
            740                 745                 750

Gly Ile Leu Lys Gln Asn Leu Gln Leu Asp Ser Phe Ser Thr Tyr Arg
            755                 760                 765

Val Tyr Phe Ser Val Ser Gly Asp Ala Asn Val Arg Ile Arg Asn Ser
    770                 775                 780

Arg Glu Val Leu Phe Glu Lys Arg Tyr Met Ser Gly Ala Lys Asp Val
785                 790                 795                 800

Ser Glu Met Phe Thr Thr Lys Phe Glu Lys Asp Asn Phe Tyr Ile Glu
                805                 810                 815

Leu Ser Gln Gly Asn Asn Leu Tyr Gly Gly Pro Ile Val His Phe Tyr
            820                 825                 830

Asp Val Ser Ile Lys
            835

<210> SEQ ID NO 20
<211> LENGTH: 775
<212> TYPE: PRT
<213> ORGANISM: Artificial
<220> FEATURE:

<223> OTHER INFORMATION: Vip3Ad3_to_2BGP sequence
<220> FEATURE:
<221> NAME/KEY: MISC_FEATURE

```
Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
            405                 410                 415

Pro Asn Glu Tyr Val Ile Thr Lys Ile Asp Phe Thr Lys Lys Met Lys
        420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Thr Ala Ala
    530                 535                 540

Ser Ala Ser Ile Thr Ala Pro Ala Gln Leu Val Gly Asn Val Gly Glu
545                 550                 555                 560

Leu Gln Gly Ala Gly Ser Ala Val Ile Trp Asn Val Asp Val Pro Val
                565                 570                 575

Thr Gly Glu Tyr Arg Ile Asn Leu Thr Trp Ser Ser Pro Tyr Ser Ser
            580                 585                 590

Lys Val Asn Thr Leu Val Met Asp Gly Thr Ala Leu Ser Tyr Ala Phe
        595                 600                 605

Ala Glu Ala Thr Val Pro Val Thr Tyr Val Gln Thr Lys Thr Leu Ser
610                 615                 620

Ala Gly Asn His Ser Phe Gly Val Arg Val Gly Ser Ser Asp Trp Gly
625                 630                 635                 640

Tyr Met Asn Val His Ser Leu Lys Leu Glu Leu Leu Gly Ser Pro Ser
                645                 650                 655

Glu Lys Leu Leu Ser Pro Glu Leu Ile Asn Thr Asn Asn Trp Thr Ser
            660                 665                 670

Thr Gly Ser Thr Asn Ile Ser Gly Asn Thr Leu Thr Leu Tyr Gln Gly
        675                 680                 685

Gly Arg Gly Ile Leu Lys Gln Asn Leu Gln Leu Asp Ser Phe Ser Thr
    690                 695                 700

Tyr Arg Val Tyr Phe Ser Val Ser Gly Asp Ala Asn Val Arg Ile Arg
705                 710                 715                 720

Asn Ser Arg Glu Val Leu Phe Glu Lys Arg Tyr Met Ser Gly Ala Lys
                725                 730                 735

Asp Val Ser Glu Met Phe Thr Thr Lys Phe Glu Lys Asp Asn Phe Tyr
            740                 745                 750

Ile Glu Leu Ser Gln Gly Asn Asn Leu Tyr Gly Gly Pro Ile Val His
        755                 760                 765

Phe Tyr Asp Val Ser Ile Lys
770                 775

<210> SEQ ID NO 21
<211> LENGTH: 798
```

<212> TYPE: PRT
<213> ORGANISM: Artificial
<220> FEATURE:
<223> OTHER INFORMATION: Vip3Ad3_to_Gp21 sequence
<220> FEATURE:
<221> NAME/KEY: MISC_FEATURE
<222> LOCATION: (542)..(676)
<223> OTHER INFORMATION: Gp21 domain

<400> SEQUENCE: 21

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Gln Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365
```

```
Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
            435                 440                 445

Glu Ile Asp Leu Asn Lys Lys Val Glu Ser Ser Glu Ala Glu Tyr
450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
            515                 520                 525

Val Pro Pro Ser Gly Phe Ile Ser Asn Ile Val Glu Asn Pro Ser Phe
530                 535                 540

Glu Arg Gly Thr Glu Gly Tyr Thr Gly Trp Ser Gly Ile Ala Thr Val
545                 550                 555                 560

Val Thr Leu Gln Val Pro His Leu Gly Thr Lys Ala Ala Lys Leu Ala
                565                 570                 575

Ala Gly Gly Ser Ala Gly Val Gly Gln Lys Ile Ser Phe Lys Lys Asp
                580                 585                 590

Arg Ser Tyr Lys Ile Gly Ile Trp Ala Lys Gln Asp Pro Asn Thr Thr
            595                 600                 605

Ile Gln Ser Thr Asp Asn Thr Lys Phe Arg Val Ala Asp Gly Asn Gly
610                 615                 620

Leu Ile Ala Ser Lys Ala Tyr Gly Pro Phe Thr Ser Asn Trp Gln Glu
625                 630                 635                 640

Val Ser Trp Thr Trp Lys Ala Thr Lys Asp Val Leu Ala Asp Val Gln
                645                 650                 655

Phe Thr Ala Phe Leu Ser Ala Gly Ala Met Tyr Phe Asp Asp Phe Tyr
                660                 665                 670

Val Val Asp Val Ser Pro Ser Glu Lys Leu Leu Ser Pro Glu Leu Ile
            675                 680                 685

Asn Thr Asn Asn Trp Thr Ser Thr Gly Ser Thr Asn Ile Ser Gly Asn
690                 695                 700

Thr Leu Thr Leu Tyr Gln Gly Gly Arg Gly Ile Leu Lys Gln Asn Leu
705                 710                 715                 720

Gln Leu Asp Ser Phe Ser Thr Tyr Arg Val Tyr Phe Ser Val Ser Gly
                725                 730                 735

Asp Ala Asn Val Arg Ile Arg Asn Ser Arg Glu Val Leu Phe Glu Lys
                740                 745                 750

Arg Tyr Met Ser Gly Ala Lys Asp Val Ser Glu Met Phe Thr Thr Lys
            755                 760                 765

Phe Glu Lys Asp Asn Phe Tyr Ile Glu Leu Ser Gln Gly Asn Asn Leu
770                 775                 780
```

-continued

Tyr Gly Gly Pro Ile Val His Phe Tyr Asp Val Ser Ile Lys
785                 790                 795

<210> SEQ ID NO 22
<211> LENGTH: 803
<212> TYPE: PRT
<213> ORGANISM: Artificial
<220> FEATURE:
<223> OTHER INFORMATION: Vip3Ad3_to_CenC sequence
<220> FEATURE:
<221> NAME/KEY: MISC_FEATURE
<222> LOCATION: (542)..(681)
<223> OTHER INFORMATION: CenC domain

<400> SEQUENCE: 22

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Gln Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
                340                 345                 350

Pro Gly His Ala Leu Ile Gly Phe Glu Ile Ser Asn Asp Ser Ile Thr
                355                 360                 365

Val Leu Lys Val Tyr Glu Ala Lys Leu Lys Gln Asn Tyr Gln Val Asp
                370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
                435                 440                 445

Glu Ile Asp Leu Asn Lys Lys Lys Val Glu Ser Ser Glu Ala Glu Tyr
                450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
                515                 520                 525

Val Pro Pro Ser Gly Phe Ile Ser Asn Ile Val Glu Asn Pro Gly Leu
                530                 535                 540

Glu Asp Gly Ile Asn Asn Trp Gln Ala Trp Gly Glu Gly Phe Thr Ala
545                 550                 555                 560

Ala Ser Asp Met Ser His Thr Gly Ser Ala Ser Leu Lys Val Leu Leu
                565                 570                 575

Asn Asn Gly Gly Arg Gln Val Val Ala Leu Gln Pro Gly Lys Ser Tyr
                580                 585                 590

Lys Leu Gly Val Trp Gly Lys Thr Ala Gly Thr Gly Thr Gly Thr Gln
                595                 600                 605

Thr Ala Thr Val Met Ile Asn Tyr Lys Lys Pro Glu Asp Asp Ser Ser
                610                 615                 620

His Thr Tyr Gly Ser Phe Gln Phe Gly Pro Asp Asn Ser Glu Phe Thr
625                 630                 635                 640

Tyr Lys Glu Ile Thr Phe Glu Thr Pro Asp Met Ala Gln Glu Trp
                645                 650                 655

Gly Thr Gln Phe Val Ser Ile Trp Ser Glu Gly Ala Asp Gln Val Tyr
                660                 665                 670

Leu Asp Asp Phe Thr Leu Ser Glu Val Ser Pro Ser Glu Lys Leu Leu
                675                 680                 685

Ser Pro Glu Leu Ile Asn Thr Asn Asn Trp Thr Ser Thr Gly Ser Thr
                690                 695                 700

Asn Ile Ser Gly Asn Thr Leu Thr Leu Tyr Gln Gly Gly Arg Gly Ile
705                 710                 715                 720

Leu Lys Gln Asn Leu Gln Leu Asp Ser Phe Ser Thr Tyr Arg Val Tyr
                725                 730                 735

Phe Ser Val Ser Gly Asp Ala Asn Val Arg Ile Arg Asn Ser Arg Glu
                740                 745                 750

```
Val Leu Phe Glu Lys Arg Tyr Met Ser Gly Ala Lys Asp Val Ser Glu
        755                 760                 765

Met Phe Thr Thr Lys Phe Glu Lys Asp Asn Phe Tyr Ile Glu Leu Ser
        770                 775                 780

Gln Gly Asn Asn Leu Tyr Gly Gly Pro Ile Val His Phe Tyr Asp Val
785                 790                 795                 800

Ser Ile Lys

<210> SEQ ID NO 23
<211> LENGTH: 796
<212> TYPE: PRT
<213> ORGANISM: Artificial
<220> FEATURE:
<223> OTHER INFORMATION: Vip3Ad3_to_PsHGF7 sequence
<220> FEATURE:
<221> NAME/KEY: MISC_FEATURE
<222> LOCATION: (542)..(674)
<223> OTHER INFORMATION: PsHGF7 domain

<400> SEQUENCE: 23

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Gln Ala Phe Leu Thr
        275                 280                 285
```

-continued

```
Leu Thr Thr Cys Arg Lys Leu Leu Gly Leu Ala Asp Ile Asp Tyr Thr
290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Pro Gly Phe
    530                 535                 540

Glu Asp Asn Leu Ala Ser Trp Thr Asn Trp Gly Asn Thr Ser Ser Val
545                 550                 555                 560

Thr Ser Pro Ala Phe Ala Gly Ala Lys Ala Ala Arg Ile Ala Ser Gly
                565                 570                 575

Glu Gly Gly Ala Gly Gln Ile Ile Pro Gly Ile Pro Ser Gly Thr Thr
            580                 585                 590

Tyr Val Leu Ser Gly His Gly Ser Val Ser Ala Gly Thr Asp Thr Ala
        595                 600                 605

Ile Val Gly Val Asp Cys Leu Asp Ala Asn Asn Asn Val Leu Ala Lys
    610                 615                 620

Asn Thr Leu Arg Phe Asn Gln Thr Leu Tyr Glu Phe Lys Ser Thr Ala
625                 630                 635                 640

Phe Thr Thr Val Pro Gly Thr Ala Lys Leu Gln Val Tyr Ile Tyr Lys
                645                 650                 655

Asn Ala Asp Ser Gly Ala Asn Ala Phe Leu Asp Asp Leu Ser Leu Val
            660                 665                 670

Glu Val Ser Pro Ser Glu Lys Leu Leu Ser Pro Glu Leu Ile Asn Thr
        675                 680                 685

Asn Asn Trp Thr Ser Thr Gly Ser Thr Asn Ile Ser Gly Asn Thr Leu
690                 695                 700

Thr Leu Tyr Gln Gly Gly Arg Gly Ile Leu Lys Gln Asn Leu Gln Leu
```

```
                705                 710                 715                 720
Asp Ser Phe Ser Thr Tyr Arg Val Tyr Phe Ser Val Ser Gly Asp Ala
                    725                 730                 735

Asn Val Arg Ile Arg Asn Ser Arg Glu Val Leu Phe Glu Lys Arg Tyr
                740                 745                 750

Met Ser Gly Ala Lys Asp Val Ser Glu Met Phe Thr Thr Lys Phe Glu
            755                 760                 765

Lys Asp Asn Phe Tyr Ile Glu Leu Ser Gln Gly Asn Asn Leu Tyr Gly
        770                 775                 780

Gly Pro Ile Val His Phe Tyr Asp Val Ser Ile Lys
785                 790                 795

<210> SEQ ID NO 24
<211> LENGTH: 137
<212> TYPE: PRT
<213> ORGANISM: Thermoanaerobacterium polysaccharolyticum

<400> SEQUENCE: 24

Pro Gly Phe Glu Asp Gly Leu Asp Ser Trp Gln Asp Trp Gln Gln Asp
1               5                   10                  15

Met Ser Ala Val Pro Glu Ala Ala His Asn Gly Ala Leu Gly Leu Lys
            20                  25                  30

Ile Gly Gly Gly Lys Ala Ala Gly Gly Gln Asp Ile Pro Leu Lys
        35                  40                  45

Pro Asn Thr Thr Tyr Ile Leu Gly Ala Trp Ala Lys Phe Asp Ser Lys
    50                  55                  60

Pro Ala Gly Thr Phe Asp Val Val Val Gln Tyr His Leu Lys Asp Ala
65                  70                  75                  80

Asn Asn Thr Tyr Val Gln His Ile Leu Asn Phe Asn Glu Thr Asp Trp
                85                  90                  95

Thr Tyr Lys Gln Leu Leu Phe Thr Thr Pro Asp Val Phe Gly Ser Thr
            100                 105                 110

Pro Gln Leu Ala Leu Trp Lys Gly Asp Thr Ser Lys Ala Asn Leu Tyr
        115                 120                 125

Val Asp Asp Val Tyr Leu Val Glu Val
    130                 135

<210> SEQ ID NO 25
<211> LENGTH: 137
<212> TYPE: PRT
<213> ORGANISM: Thermoanaerobacterium polysaccharolyticum

<400> SEQUENCE: 25

Pro Gly Phe Glu Asn Gly Met Asp Gly Trp Pro Asp Trp Gly Tyr Pro
1               5                   10                  15

Val Ser Ala Val Pro Glu Ala Ala Tyr Gly Gly Thr Lys Gly Phe Lys
            20                  25                  30

Leu Ser Gly Gly Lys Gln Ala Gly Met Gly Gln Lys Val Ala Leu Lys
        35                  40                  45

Pro Asn Thr Thr Tyr Ile Leu Gly Ala Trp Gly Lys Phe Thr Ala Lys
    50                  55                  60

Pro Gly Thr Tyr Cys Asp Val Ile Val Gln Tyr His Leu Lys Asp Ala
65                  70                  75                  80

Asn Asn Thr Tyr Val Gln Asn Ile Leu Arg Phe Thr Glu Thr Asp Trp
                85                  90                  95

Thr Tyr Lys Gln Val Val Phe Thr Thr Pro Asp Ala Phe Gly Ser Asp
```

```
                   100                 105                 110

Pro Glu Phe Val Leu Trp Lys Asp Asp Ala Ser Asn Ala Asp Phe Tyr
        115                 120                 125

Ala Asp Asn Ile Thr Leu Val Glu Val
        130                 135

<210> SEQ ID NO 26
<211> LENGTH: 161
<212> TYPE: PRT
<213> ORGANISM: Thermotoga maritima

<400> SEQUENCE: 26

Asp Phe Ser Ser Pro Glu Glu Val Lys Asn Trp Trp Asn Ser Gly Thr
1               5                   10                  15

Trp Gln Ala Glu Phe Gly Ser Pro Asp Ile Glu Trp Asn Gly Glu Val
            20                  25                  30

Gly Asn Gly Ala Leu Gln Leu Asn Val Lys Leu Pro Gly Lys Ser Asp
        35                  40                  45

Trp Glu Glu Val Arg Val Ala Arg Lys Phe Glu Arg Leu Ser Glu Cys
    50                  55                  60

Glu Ile Leu Glu Tyr Asp Ile Tyr Ile Pro Asn Val Glu Gly Leu Lys
65                  70                  75                  80

Gly Arg Leu Arg Pro Tyr Ala Val Leu Asn Pro Gly Trp Val Lys Ile
                85                  90                  95

Gly Leu Asp Met Asn Asn Ala Asn Val Glu Ser Ala Glu Ile Ile Thr
            100                 105                 110

Phe Gly Gly Lys Glu Tyr Arg Arg Phe His Val Arg Ile Glu Phe Asp
        115                 120                 125

Arg Thr Ala Gly Val Lys Glu Leu His Ile Gly Val Val Gly Asp His
    130                 135                 140

Leu Arg Tyr Asp Gly Pro Ile Phe Ile Asp Asn Val Arg Leu Tyr Lys
145                 150                 155                 160

Arg

<210> SEQ ID NO 27
<211> LENGTH: 174
<212> TYPE: PRT
<213> ORGANISM: Caldicellulosiruptor saccharolyticus

<400> SEQUENCE: 27

Asp Phe Glu Asp Gly Thr Val Met Ser Phe Gly Glu Ala Trp Gly Asp
1               5                   10                  15

Ser Leu Lys Cys Ile Lys Lys Val Ser Val Ser Gln Asp Leu Gln Arg
            20                  25                  30

Pro Gly Asn Lys Tyr Ala Leu Arg Leu Asp Val Glu Phe Asn Pro Asn
        35                  40                  45

Asn Gly Trp Asp Gln Gly Asp Leu Gly Thr Trp Ile Gly Gly Val Val
    50                  55                  60

Glu Gly Gln Phe Asp Phe Thr Gly Tyr Lys Ser Val Glu Phe Glu Met
65                  70                  75                  80

Phe Ile Pro Tyr Asp Glu Phe Ser Lys Ser Gln Gly Phe Ala Tyr
                85                  90                  95

Lys Val Val Ile Asn Asp Gly Trp Lys Glu Leu Gly Ser Glu Phe Asn
            100                 105                 110

Ile Thr Ala Asn Ala Gly Lys Lys Val Lys Ile Asn Gly Lys Asp Tyr
        115                 120                 125
```

```
Thr Val Ile His Lys Ala Phe Ala Ile Pro Glu Asp Phe Arg Thr Lys
    130                 135                 140

Lys Arg Ala Gln Leu Val Phe Gln Phe Ala Gly Gln Asn Ser Asn Tyr
145                 150                 155                 160

Lys Gly Pro Ile Tyr Leu Asp Asn Val Arg Ile Arg Pro Glu
                165                 170

<210> SEQ ID NO 28
<211> LENGTH: 112
<212> TYPE: PRT
<213> ORGANISM: Cellvibrio japonicus

<400> SEQUENCE: 28

Thr Ala Ala Ser Ala Ser Ile Thr Ala Pro Ala Gln Leu Val Gly Asn
1               5                   10                  15

Val Gly Glu Leu Gln Gly Ala Gly Ser Ala Val Ile Trp Asn Val Asp
            20                  25                  30

Val Pro Val Thr Gly Glu Tyr Arg Ile Asn Leu Thr Trp Ser Ser Pro
        35                  40                  45

Tyr Ser Ser Lys Val Asn Thr Leu Val Met Asp Gly Thr Ala Leu Ser
    50                  55                  60

Tyr Ala Phe Ala Glu Ala Thr Val Pro Val Thr Tyr Val Gln Thr Lys
65                  70                  75                  80

Thr Leu Ser Ala Gly Asn His Ser Phe Gly Val Arg Val Gly Ser Ser
                85                  90                  95

Asp Trp Gly Tyr Met Asn Val His Ser Leu Lys Leu Glu Leu Leu Gly
            100                 105                 110

<210> SEQ ID NO 29
<211> LENGTH: 135
<212> TYPE: PRT
<213> ORGANISM: Klebsiella pneumoniae

<400> SEQUENCE: 29

Pro Ser Phe Glu Arg Gly Thr Glu Gly Tyr Thr Gly Trp Ser Gly Ile
1               5                   10                  15

Ala Thr Val Val Thr Leu Gln Val Pro His Leu Gly Thr Lys Ala Ala
            20                  25                  30

Lys Leu Ala Ala Gly Gly Ser Ala Gly Val Gly Gln Lys Ile Ser Phe
        35                  40                  45

Lys Lys Asp Arg Ser Tyr Lys Ile Gly Ile Trp Ala Lys Gln Asp Pro
    50                  55                  60

Asn Thr Thr Ile Gln Ser Thr Asp Asn Thr Lys Phe Arg Val Ala Asp
65                  70                  75                  80

Gly Asn Gly Leu Ile Ala Ser Lys Ala Tyr Gly Pro Phe Thr Ser Asn
                85                  90                  95

Trp Gln Glu Val Ser Trp Thr Trp Lys Ala Thr Lys Asp Val Leu Ala
            100                 105                 110

Asp Val Gln Phe Thr Ala Phe Leu Ser Ala Gly Ala Met Tyr Phe Asp
        115                 120                 125

Asp Phe Tyr Val Val Asp Val
    130                 135

<210> SEQ ID NO 30
<211> LENGTH: 140
<212> TYPE: PRT
<213> ORGANISM: Paenibacillus sp. JDR-2
```

<400> SEQUENCE: 30

```
Pro Gly Leu Glu Asp Gly Ile Asn Asn Trp Gln Ala Trp Gly Glu Gly
1               5                   10                  15
Phe Thr Ala Ala Ser Asp Met Ser His Thr Gly Ser Ala Ser Leu Lys
            20                  25                  30
Val Leu Leu Asn Asn Gly Gly Arg Gln Val Val Ala Leu Gln Pro Gly
        35                  40                  45
Lys Ser Tyr Lys Leu Gly Val Trp Gly Lys Thr Ala Gly Thr Gly Thr
    50                  55                  60
Gly Thr Gln Thr Ala Thr Val Met Ile Asn Tyr Lys Lys Pro Glu Asp
65                  70                  75                  80
Asp Ser Ser His Thr Tyr Gly Ser Phe Gln Phe Gly Pro Asp Asn Ser
                85                  90                  95
Glu Phe Thr Tyr Lys Glu Ile Thr Phe Glu Thr Pro Asp Asp Met Ala
            100                 105                 110
Gln Glu Trp Gly Thr Gln Phe Val Ser Ile Trp Ser Gly Gly Ala Asp
        115                 120                 125
Gln Val Tyr Leu Asp Asp Phe Thr Leu Ser Glu Val
    130                 135                 140
```

<210> SEQ ID NO 31
<211> LENGTH: 133
<212> TYPE: PRT
<213> ORGANISM: Paenibacillus sp. HGF7

<400> SEQUENCE: 31

```
Pro Gly Phe Glu Asp Asn Leu Ala Ser Trp Thr Asn Trp Gly Asn Thr
1               5                   10                  15
Ser Ser Val Thr Ser Pro Ala Phe Ala Gly Ala Lys Ala Ala Arg Ile
            20                  25                  30
Ala Ser Gly Glu Gly Gly Ala Gly Gln Ile Ile Pro Gly Ile Pro Ser
        35                  40                  45
Gly Thr Thr Tyr Val Leu Ser Gly His Gly Ser Val Ser Ala Gly Thr
    50                  55                  60
Asp Thr Ala Ile Val Gly Val Asp Cys Leu Asp Ala Asn Asn Asn Val
65                  70                  75                  80
Leu Ala Lys Asn Thr Leu Arg Phe Asn Gln Thr Leu Tyr Glu Phe Lys
                85                  90                  95
Ser Thr Ala Phe Thr Thr Val Pro Gly Thr Ala Lys Leu Gln Val Tyr
            100                 105                 110
Ile Tyr Lys Asn Ala Asp Ser Gly Ala Asn Ala Phe Leu Asp Asp Leu
        115                 120                 125
Ser Leu Val Glu Val
    130
```

<210> SEQ ID NO 32
<211> LENGTH: 146
<212> TYPE: PRT
<213> ORGANISM: Caldicellulosiruptor saccharolyticus

<400> SEQUENCE: 32

```
Asp Phe Glu Glu Ser Thr Gln Gly Trp Thr Gly Ser Ser Leu Ser Arg
1               5                   10                  15
Gly Pro Trp Thr Val Thr Glu Trp Ser Ser Lys Gly Asn His Ser Leu
            20                  25                  30
```

```
Lys Ala Asp Ile Gln Met Ser Asn Ser Gln His Tyr Leu His Val
             35                  40                  45

Ile Gln Asn Arg Ser Leu Gln Gln Asn Ser Arg Ile Gln Ala Thr Val
 50                  55                  60

Lys His Ala Asn Trp Gly Ser Val Gly Asn Gly Met Thr Ala Arg Leu
 65                  70                  75                  80

Tyr Val Lys Thr Gly His Gly Tyr Thr Trp Tyr Ser Gly Ser Phe Val
                 85                  90                  95

Pro Ile Asn Gly Ser Ser Gly Thr Thr Leu Ser Leu Asp Leu Ser Asn
             100                 105                 110

Val Gln Asn Leu Ser Gln Val Arg Glu Ile Gly Val Gln Phe Gln Ser
         115                 120                 125

Glu Ser Asn Ser Ser Gly Gln Thr Ser Ile Tyr Ile Asp Asn Val Ile
         130                 135                 140

Val Glu
145
```

```
<210> SEQ ID NO 33
<211> LENGTH: 799
<212> TYPE: PRT
<213> ORGANISM: Artificial
<220> FEATURE:
<223> OTHER INFORMATION: Vip3Dd3_to_2ZEX sequence

<400> SEQUENCE: 33

Met Asn Met Asn Asn Thr Lys Leu Asn Ala Arg Ala Leu Pro Ser Phe
 1               5                  10                  15

Ile Asp Tyr Phe Asn Gly Ile Tyr Gly Phe Ala Thr Gly Ile Lys Asp
                 20                  25                  30

Ile Met Asn Met Ile Phe Lys Thr Asp Thr Gly Gly Asn Leu Thr Leu
             35                  40                  45

Asp Glu Ile Leu Lys Asn Gln Gln Leu Leu Asn Glu Ile Ser Gly Lys
 50                  55                  60

Leu Asp Gly Val Asn Gly Ser Leu Asn Asp Leu Ile Ala Gln Gly Asn
 65                  70                  75                  80

Leu Asn Thr Glu Leu Ser Lys Glu Ile Leu Lys Ile Ala Asn Glu Gln
                 85                  90                  95

Asn Gln Val Leu Asn Asp Val Asn Asn Lys Leu Asp Ala Ile Asn Thr
             100                 105                 110

Met Leu His Ile Tyr Leu Pro Lys Ile Thr Ser Met Leu Ser Asp Val
         115                 120                 125

Met Lys Gln Asn Tyr Ala Leu Ser Leu Gln Ile Glu Tyr Leu Ser Lys
130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                 165                 170                 175

Lys Tyr Val Asn Glu Lys Phe Glu Glu Leu Thr Phe Ala Thr Glu Thr
             180                 185                 190

Thr Leu Lys Val Lys Lys Asp Ser Ser Pro Ala Asp Ile Leu Asp Glu
         195                 200                 205

Leu Thr Glu Leu Thr Glu Leu Ala Lys Ser Val Thr Lys Asn Asp Val
         210                 215                 220

Asp Gly Phe Glu Phe Tyr Leu Asn Thr Phe His Asp Val Met Val Gly
225                 230                 235                 240
```

```
Asn Asn Leu Phe Gly Arg Ser Ala Leu Lys Thr Ala Ser Glu Leu Ile
            245                 250                 255
Ala Lys Glu Asn Val Lys Thr Ser Gly Ser Glu Val Gly Asn Val Tyr
        260                 265                 270
Asn Phe Leu Ile Val Leu Thr Ala Leu Gln Ala Lys Ala Phe Leu Thr
    275                 280                 285
Leu Thr Thr Cys Arg Lys Leu Leu Gly Leu Ala Asp Ile Asp Tyr Thr
290                 295                 300
Ser Ile Met Asn Glu His Leu Asn Lys Glu Lys Glu Phe Arg Val
305                 310                 315                 320
Asn Ile Leu Pro Thr Leu Ser Asn Thr Phe Ser Asn Pro Asn Tyr Ala
                325                 330                 335
Lys Val Lys Gly Ser Asp Glu Asp Ala Lys Met Ile Val Glu Ala Lys
            340                 345                 350
Pro Gly His Ala Leu Val Gly Phe Glu Met Ser Asn Asp Ser Ile Thr
        355                 360                 365
Val Leu Lys Val Tyr Glu Ala Lys Leu Lys Gln Asn Tyr Gln Val Asp
    370                 375                 380
Lys Asp Ser Leu Ser Glu Val Ile Tyr Gly Asp Thr Asp Lys Leu Phe
385                 390                 395                 400
Cys Pro Asp Gln Ser Glu Gln Ile Tyr Tyr Thr Asn Asn Ile Val Phe
                405                 410                 415
Pro Asn Glu Tyr Val Ile Thr Lys Ile Asp Phe Thr Lys Lys Met Lys
            420                 425                 430
Thr Leu Arg Tyr Glu Val Thr Ala Asn Phe Tyr Asp Ser Ser Thr Gly
        435                 440                 445
Glu Ile Asp Leu Asn Lys Lys Lys Val Glu Ser Ser Glu Ala Glu Tyr
    450                 455                 460
Arg Thr Leu Ser Ala Asn Asp Asp Gly Val Tyr Met Pro Leu Gly Val
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
            500                 505                 510
Glu Leu Leu Leu Ala Thr Asp Leu Ser Asn Lys Glu Thr Lys Leu Ile
        515                 520                 525
Val Pro Pro Ser Gly Phe Ile Ser Asn Ile Val Glu Asn Pro Gly Phe
    530                 535                 540
Glu Asp Gly Leu Asp Ser Trp Gln Asp Trp Gln Gln Asp Met Ser Ala
545                 550                 555                 560
Val Pro Glu Ala Ala His Asn Gly Ala Leu Gly Leu Lys Ile Gly Gly
                565                 570                 575
Gly Lys Ala Ala Gly Gly Gln Asp Ile Pro Leu Lys Pro Asn Thr
            580                 585                 590
Thr Tyr Ile Leu Gly Ala Trp Ala Lys Phe Asp Ser Lys Pro Ala Gly
        595                 600                 605
Thr Phe Asp Val Val Gln Tyr His Leu Lys Asp Ala Asn Asn Thr
    610                 615                 620
Tyr Val Gln His Ile Leu Asn Phe Asn Glu Thr Asp Trp Thr Tyr Lys
625                 630                 635                 640
Gln Leu Leu Phe Thr Thr Pro Asp Val Phe Gly Ser Thr Pro Gln Leu
                645                 650                 655
Ala Leu Trp Lys Gly Asp Thr Ser Lys Ala Asn Leu Tyr Val Asp Asp
```

```
                    660                 665                 670
Val Tyr Leu Val Glu Val Lys Pro Ala Glu Asp Leu Leu Ser Pro Glu
                675                 680                 685

Leu Ile Asn Pro Asn Ser Trp Ile Thr Thr Pro Gly Ala Ser Ile Ser
                690                 695                 700

Gly Asn Lys Leu Phe Ile Asn Leu Gly Thr Asn Gly Thr Phe Arg Gln
705                 710                 715                 720

Ser Leu Ser Leu Asn Ser Tyr Ser Thr Tyr Ser Ile Ser Phe Thr Ala
                725                 730                 735

Ser Gly Pro Phe Asn Val Thr Val Arg Asn Ser Arg Glu Val Leu Phe
                740                 745                 750

Glu Arg Ser Asn Leu Met Ser Ser Thr Ser His Ile Ser Gly Thr Phe
                755                 760                 765

Lys Thr Glu Ser Asn Asn Thr Gly Leu Tyr Val Glu Leu Ser Arg Arg
                770                 775                 780

Ser Gly Gly Gly Gly His Ile Ser Phe Glu Asn Val Ser Ile Lys
785                 790                 795

<210> SEQ ID NO 34
<211> LENGTH: 799
<212> TYPE: PRT
<213> ORGANISM: Artificial
<220> FEATURE:
<223> OTHER INFORMATION: Vip3Dd3_to_2ZEZ sequence

<400> SEQUENCE: 34

Met Asn Met Asn Asn Thr Lys Leu Asn Ala Arg Ala Leu Pro Ser Phe
1                   5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asn Leu Thr Leu
            35                  40                  45

Asp Glu Ile Leu Lys Asn Gln Gln Leu Leu Asn Glu Ile Ser Gly Lys
        50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
```

-continued

```
              225                 230                 235                 240
Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
                260                 265                 270

Asn Phe Leu Ile Val Leu Thr Ala Leu Gln Ala Lys Ala Phe Leu Thr
                275                 280                 285

Leu Thr Thr Cys Arg Lys Leu Leu Gly Leu Ala Asp Ile Asp Tyr Thr
                290                 295                 300

Ser Ile Met Asn Glu His Leu Asn Lys Glu Lys Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
                340                 345                 350

Pro Gly His Ala Leu Val Gly Phe Glu Met Ser Asn Asp Ser Ile Thr
                355                 360                 365

Val Leu Lys Val Tyr Glu Ala Lys Leu Lys Gln Asn Tyr Gln Val Asp
                370                 375                 380

Lys Asp Ser Leu Ser Glu Val Ile Tyr Gly Asp Thr Asp Lys Leu Phe
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
                435                 440                 445

Glu Ile Asp Leu Asn Lys Lys Val Glu Ser Glu Ala Glu Tyr
                450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
                515                 520                 525

Val Pro Pro Ser Gly Phe Ile Ser Asn Ile Val Glu Asn Pro Gly Phe
                530                 535                 540

Glu Asn Gly Met Asp Gly Trp Pro Asp Trp Gly Tyr Pro Val Ser Ala
545                 550                 555                 560

Val Pro Glu Ala Ala Tyr Gly Gly Thr Lys Gly Phe Lys Leu Ser Gly
                565                 570                 575

Gly Lys Gln Ala Gly Met Gly Gln Lys Val Ala Leu Lys Pro Asn Thr
                580                 585                 590

Thr Tyr Ile Leu Gly Ala Trp Gly Lys Phe Thr Ala Lys Pro Gly Thr
                595                 600                 605

Tyr Cys Asp Val Ile Val Gln Tyr His Leu Lys Asp Ala Asn Asn Thr
                610                 615                 620

Tyr Val Gln Asn Ile Leu Arg Phe Thr Glu Thr Asp Trp Thr Tyr Lys
625                 630                 635                 640

Gln Val Val Phe Thr Thr Pro Asp Ala Phe Gly Ser Asp Pro Glu Phe
                645                 650                 655
```

```
Val Leu Trp Lys Asp Asp Ala Ser Asn Ala Asp Phe Tyr Ala Asp Asn
            660                 665                 670

Ile Thr Leu Val Glu Val Lys Pro Ala Glu Asp Leu Ser Pro Glu
        675                 680                 685

Leu Ile Asn Pro Asn Ser Trp Ile Thr Thr Pro Gly Ala Ser Ile Ser
    690                 695                 700

Gly Asn Lys Leu Phe Ile Asn Leu Gly Thr Asn Gly Thr Phe Arg Gln
705                 710                 715                 720

Ser Leu Ser Leu Asn Ser Tyr Ser Thr Tyr Ser Ile Ser Phe Thr Ala
                725                 730                 735

Ser Gly Pro Phe Asn Val Thr Val Arg Asn Ser Arg Glu Val Leu Phe
            740                 745                 750

Glu Arg Ser Asn Leu Met Ser Ser Thr Ser His Ile Ser Gly Thr Phe
        755                 760                 765

Lys Thr Glu Ser Asn Asn Thr Gly Leu Tyr Val Glu Leu Ser Arg Arg
    770                 775                 780

Ser Gly Gly Gly Gly His Ile Ser Phe Glu Asn Val Ser Ile Lys
785                 790                 795

<210> SEQ ID NO 35
<211> LENGTH: 823
<212> TYPE: PRT
<213> ORGANISM: Artificial
<220> FEATURE:
<223> OTHER INFORMATION: Vip3Dd3_to_1OFE sequence

<400> SEQUENCE: 35

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220
```

```
Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
            245                 250                 255

Ala Lys Glu Asn Val Lys Thr Ser Gly Ser Glu Val Gly Asn Val Tyr
        260                 265                 270

Asn Phe Leu Ile Val Leu Thr Ala Leu Gln Ala Lys Ala Phe Leu Thr
    275                 280                 285

Leu Thr Thr Cys Arg Lys Leu Leu Gly Leu Ala Asp Ile Asp Tyr Thr
290                 295                 300

Ser Ile Met Asn Glu His Leu Asn Lys Glu Lys Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Met Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Thr Asp Lys Leu Phe
385                 390                 395                 400

Cys Pro Asp Gln Ser Glu Gln Ile Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Val Glu Ser Ser Glu Ala Glu Tyr
450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Asp Phe Ser
    530                 535                 540

Ser Pro Glu Glu Val Lys Asn Trp Trp Asn Ser Gly Thr Trp Gln Ala
545                 550                 555                 560

Glu Phe Gly Ser Pro Asp Ile Glu Trp Asn Gly Glu Val Gly Asn Gly
                565                 570                 575

Ala Leu Gln Leu Asn Val Lys Leu Pro Gly Lys Ser Asp Trp Glu Glu
            580                 585                 590

Val Arg Val Ala Arg Lys Phe Glu Arg Leu Ser Glu Cys Glu Ile Leu
        595                 600                 605

Glu Tyr Asp Ile Tyr Ile Pro Asn Val Glu Gly Leu Lys Gly Arg Leu
    610                 615                 620

Arg Pro Tyr Ala Val Leu Asn Pro Gly Trp Val Lys Ile Gly Leu Asp
625                 630                 635                 640
```

```
Met Asn Asn Ala Asn Val Glu Ser Ala Glu Ile Ile Thr Phe Gly Gly
                645                 650                 655

Lys Glu Tyr Arg Arg Phe His Val Arg Ile Glu Phe Asp Arg Thr Ala
            660                 665                 670

Gly Val Lys Glu Leu His Ile Gly Val Val Gly Asp His Leu Arg Tyr
        675                 680                 685

Asp Gly Pro Ile Phe Ile Asp Asn Val Arg Leu Tyr Lys Arg Lys Pro
    690                 695                 700

Ala Glu Asp Leu Leu Ser Pro Glu Leu Ile Asn Pro Asn Ser Trp Ile
705                 710                 715                 720

Thr Thr Pro Gly Ala Ser Ile Ser Gly Asn Lys Leu Phe Ile Asn Leu
            725                 730                 735

Gly Thr Asn Gly Thr Phe Arg Gln Ser Leu Ser Leu Asn Ser Tyr Ser
        740                 745                 750

Thr Tyr Ser Ile Ser Phe Thr Ala Ser Gly Pro Phe Asn Val Thr Val
    755                 760                 765

Arg Asn Ser Arg Glu Val Leu Phe Glu Arg Ser Asn Leu Met Ser Ser
770                 775                 780

Thr Ser His Ile Ser Gly Thr Phe Lys Thr Glu Ser Asn Asn Thr Gly
785                 790                 795                 800

Leu Tyr Val Glu Leu Ser Arg Arg Ser Gly Gly Gly His Ile Ser
            805                 810                 815

Phe Glu Asn Val Ser Ile Lys
            820

<210> SEQ ID NO 36
<211> LENGTH: 836
<212> TYPE: PRT
<213> ORGANISM: Artificial
<220> FEATURE:
<223> OTHER INFORMATION: Vip3Dd3_to_1PMH sequence

<400> SEQUENCE: 36

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
            85                  90                  95

Asn Gln Val Leu Asn Asp Val Asn Asn Lys Leu Asp Ala Ile Asn Thr
        100                 105                 110

Met Leu His Ile Tyr Leu Pro Lys Ile Thr Ser Met Leu Ser Asp Val
    115                 120                 125

Met Lys Gln Asn Tyr Ala Leu Ser Leu Gln Ile Glu Tyr Leu Ser Lys
130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
            165                 170                 175
```

```
Lys Tyr Val Asn Glu Lys Phe Glu Glu Leu Thr Phe Ala Thr Glu Thr
                180                 185                 190

Thr Leu Lys Val Lys Lys Asp Ser Ser Pro Ala Asp Ile Leu Asp Glu
            195                 200                 205

Leu Thr Glu Leu Thr Glu Leu Ala Lys Ser Val Thr Lys Asn Asp Val
        210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Met Ser Asn Asp Ser Ile Thr
        355                 360                 365

Val Leu Lys Val Tyr Glu Ala Lys Leu Lys Gln Asn Tyr Gln Val Asp
370                 375                 380

Lys Asp Ser Leu Ser Glu Val Ile Tyr Gly Asp Thr Asp Lys Leu Phe
385                 390                 395                 400

Cys Pro Asp Gln Ser Glu Gln Ile Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
            435                 440                 445

Glu Ile Asp Leu Asn Lys Lys Val Glu Ser Ser Glu Ala Glu Tyr
        450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Asp Phe Glu
530                 535                 540

Asp Gly Thr Val Met Ser Phe Gly Glu Ala Trp Gly Asp Ser Leu Lys
545                 550                 555                 560

Cys Ile Lys Lys Val Ser Val Ser Gln Asp Leu Gln Arg Pro Gly Asn
                565                 570                 575

Lys Tyr Ala Leu Arg Leu Asp Val Glu Phe Asn Pro Asn Asn Gly Trp
            580                 585                 590

Asp Gln Gly Asp Leu Gly Thr Trp Ile Gly Gly Val Val Glu Gly Gln
```

-continued

```
                595                 600                 605

Phe Asp Phe Thr Gly Tyr Lys Ser Val Glu Phe Glu Met Phe Ile Pro
610                 615                 620

Tyr Asp Glu Phe Ser Lys Ser Gln Gly Gly Phe Ala Tyr Lys Val Val
625                 630                 635                 640

Ile Asn Asp Gly Trp Lys Glu Leu Gly Ser Glu Phe Asn Ile Thr Ala
                645                 650                 655

Asn Ala Gly Lys Lys Val Lys Ile Asn Gly Lys Asp Tyr Thr Val Ile
                660                 665                 670

His Lys Ala Phe Ala Ile Pro Glu Asp Phe Arg Thr Lys Lys Arg Ala
                675                 680                 685

Gln Leu Val Phe Gln Phe Ala Gly Gln Asn Ser Asn Tyr Lys Gly Pro
690                 695                 700

Ile Tyr Leu Asp Asn Val Arg Ile Arg Pro Glu Lys Pro Ala Glu Asp
705                 710                 715                 720

Leu Leu Ser Pro Glu Leu Ile Asn Pro Asn Ser Trp Ile Thr Thr Pro
                725                 730                 735

Gly Ala Ser Ile Ser Gly Asn Lys Leu Phe Ile Asn Leu Gly Thr Asn
                740                 745                 750

Gly Thr Phe Arg Gln Ser Leu Ser Leu Asn Ser Tyr Ser Thr Tyr Ser
                755                 760                 765

Ile Ser Phe Thr Ala Ser Gly Pro Phe Asn Val Thr Val Arg Asn Ser
770                 775                 780

Arg Glu Val Leu Phe Glu Arg Ser Asn Leu Met Ser Ser Thr Ser His
785                 790                 795                 800

Ile Ser Gly Thr Phe Lys Thr Glu Ser Asn Asn Thr Gly Leu Tyr Val
                805                 810                 815

Glu Leu Ser Arg Arg Ser Gly Gly Gly His Ile Ser Phe Glu Asn
                820                 825                 830

Val Ser Ile Lys
        835

<210> SEQ ID NO 37
<211> LENGTH: 774
<212> TYPE: PRT
<213> ORGANISM: Artificial
<220> FEATURE:
<223> OTHER INFORMATION: Vip3Dd3_to_2BGP sequence

<400> SEQUENCE: 37

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asn Leu Thr Leu
                35                  40                  45

Asp Gl

```
            115                 120                 125
Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
                180                 185                 190

Thr Leu Lys Val Lys Lys Asp Ser Ser Pro Ala Asp Ile Leu Asp Glu
            195                 200                 205

Leu Thr Glu Leu Thr Glu Leu Ala Lys Ser Val Thr Lys Asn Asp Val
            210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
                260                 265                 270

Asn Phe Leu Ile Val Leu Thr Ala Leu Gln Ala Lys Ala Phe Leu Thr
            275                 280                 285

Leu Thr Thr Cys Arg Lys Leu Leu Gly Leu Ala Asp Ile Asp Tyr Thr
            290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
                340                 345                 350

Pro Gly His Ala Leu Val Gly Phe Glu Met Ser Asn Asp Ser Ile Thr
            355                 360                 365

Val Leu Lys Val Tyr Glu Ala Lys Leu Lys Gln Asn Tyr Gln Val Asp
            370                 375                 380

Lys Asp Ser Leu Ser Glu Val Ile Tyr Gly Asp Thr Asp Lys Leu Phe
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
            435                 440                 445

Glu Ile Asp Leu Asn Lys Lys Val Glu Ser Ser Glu Ala Glu Tyr
            450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
            515                 520                 525

Val Pro Pro Ser Gly Phe Ile Ser Asn Ile Val Glu Asn Thr Ala Ala
            530                 535                 540
```

```
Ser Ala Ser Ile Thr Ala Pro Ala Gln Leu Val Gly Asn Val Gly Glu
545                 550                 555                 560

Leu Gln Gly Ala Gly Ser Ala Val Ile Trp Asn Val Asp Val Pro Val
            565                 570                 575

Thr Gly Glu Tyr Arg Ile Asn Leu Thr Trp Ser Ser Pro Tyr Ser Ser
        580                 585                 590

Lys Val Asn Thr Leu Val Met Asp Gly Thr Ala Leu Ser Tyr Ala Phe
                595                 600                 605

Ala Glu Ala Thr Val Pro Val Thr Tyr Val Gln Thr Lys Thr Leu Ser
            610                 615                 620

Ala Gly Asn His Ser Phe Gly Val Arg Val Gly Ser Ser Asp Trp Gly
625                 630                 635                 640

Tyr Met Asn Val His Ser Leu Lys Leu Glu Leu Leu Gly Lys Pro Ala
                645                 650                 655

Glu Asp Leu Leu Ser Pro Glu Leu Ile Asn Pro Asn Ser Trp Ile Thr
            660                 665                 670

Thr Pro Gly Ala Ser Ile Ser Gly Asn Lys Leu Phe Ile Asn Leu Gly
        675                 680                 685

Thr Asn Gly Thr Phe Arg Gln Ser Leu Ser Leu Asn Ser Tyr Ser Thr
690                 695                 700

Tyr Ser Ile Ser Phe Thr Ala Ser Gly Pro Phe Asn Val Thr Val Arg
705                 710                 715                 720

Asn Ser Arg Glu Val Leu Phe Glu Arg Ser Asn Leu Met Ser Ser Thr
                725                 730                 735

Ser His Ile Ser Gly Thr Phe Lys Thr Glu Ser Asn Asn Thr Gly Leu
            740                 745                 750

Tyr Val Glu Leu Ser Arg Arg Ser Gly Gly Gly Gly His Ile Ser Phe
        755                 760                 765

Glu Asn Val Ser Ile Lys
    770

<210> SEQ ID NO 38
<211> LENGTH: 797
<212> TYPE: PRT
<213> ORGANISM: Artificial
<220> FEATURE:
<223> OTHER INFORMATION: Vip3Dd3_to_GP21 sequence

<400> SEQUENCE: 38

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125
```

```
Met Lys Gln Asn Tyr Ala Leu Ser Leu Gln Ile Glu Tyr Leu Ser Lys
            130                 135                 140
Gln Leu Gln Glu Ile Ser Asp Lys Leu Asp Ile Ile Asn Val Asn Val
145                 150                 155                 160
Leu Ile Asn Ser Thr Leu Thr Glu Ile Thr Pro Ala Tyr Gln Arg Ile
                165                 170                 175
Lys Tyr Val Asn Glu Lys Phe Glu Glu Leu Thr Phe Ala Thr Glu Thr
            180                 185                 190
Thr Leu Lys Val Lys Lys Asp Ser Ser Pro Ala Asp Ile Leu Asp Glu
            195                 200                 205
Leu Thr Glu Leu Thr Glu Leu Ala Lys Ser Val Thr Lys Asn Asp Val
210                 215                 220
Asp Gly Phe Glu Phe Tyr Leu Asn Thr Phe His Asp Val Met Val Gly
225                 230                 235                 240
Asn Asn Leu Phe Gly Arg Ser Ala Leu Lys Thr Ala Ser Glu Leu Ile
                245                 250                 255
Ala Lys Glu Asn Val Lys Thr Ser Gly Ser Glu Val Gly Asn Val Tyr
                260                 265                 270
Asn Phe Leu Ile Val Leu Thr Ala Leu Gln Ala Lys Ala Phe Leu Thr
            275                 280                 285
Leu Thr Thr Cys Arg Lys Leu Leu Gly Leu Ala Asp Ile Asp Tyr Thr
290                 295                 300
Ser Ile Met Asn Glu His Leu Asn Lys Glu Lys Glu Glu Phe Arg Val
305                 310                 315                 320
Asn Ile Leu Pro Thr Leu Ser Asn Thr Phe Ser Asn Pro Asn Tyr Ala
                325                 330                 335
Lys Val Lys Gly Ser Asp Glu Asp Ala Lys Met Ile Val Glu Ala Lys
            340                 345                 350
Pro Gly His Ala Leu Val Gly Phe Glu Met Ser Asn Asp Ser Ile Thr
            355                 360                 365
Val Leu Lys Val Tyr Glu Ala Lys Leu Lys Gln Asn Tyr Gln Val Asp
            370                 375                 380
Lys Asp Ser Leu Ser Glu Val Ile Tyr Gly Asp Thr Lys Leu Phe
385                 390                 395                 400
Cys Pro Asp Gln Ser Glu Gln Ile Tyr Tyr Thr Asn Asn Ile Val Phe
                405                 410                 415
Pro Asn Glu Tyr Val Ile Thr Lys Ile Asp Phe Thr Lys Met Lys
                420                 425                 430
Thr Leu Arg Tyr Glu Val Thr Ala Asn Phe Tyr Asp Ser Ser Thr Gly
            435                 440                 445
Glu Ile Asp Leu Asn Lys Lys Val Glu Ser Ser Glu Ala Glu Tyr
450                 455                 460
Arg Thr Leu Ser Ala Asn Asp Asp Gly Val Tyr Met Pro Leu Gly Val
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
            500                 505                 510
Glu Leu Leu Leu Ala Thr Asp Leu Ser Asn Lys Glu Thr Lys Leu Ile
            515                 520                 525
Val Pro Pro Ser Gly Phe Ile Ser Asn Ile Val Glu Asn Pro Ser Phe
            530                 535                 540
```

```
Glu Arg Gly Thr Glu Gly Tyr Thr Gly Trp Ser Gly Ile Ala Thr Val
545                 550                 555                 560

Val Thr Leu Gln Val Pro His Leu Gly Thr Lys Ala Ala Lys Leu Ala
                565                 570                 575

Ala Gly Gly Ser Ala Gly Val Gly Gln Lys Ile Ser Phe Lys Lys Asp
            580                 585                 590

Arg Ser Tyr Lys Ile Gly Ile Trp Ala Lys Gln Asp Pro Asn Thr Thr
        595                 600                 605

Ile Gln Ser Thr Asp Asn Thr Lys Phe Arg Val Ala Asp Gly Asn Gly
    610                 615                 620

Leu Ile Ala Ser Lys Ala Tyr Gly Pro Phe Thr Ser Asn Trp Gln Glu
625                 630                 635                 640

Val Ser Trp Thr Trp Lys Ala Thr Lys Asp Val Leu Ala Asp Val Gln
                645                 650                 655

Phe Thr Ala Phe Leu Ser Ala Gly Ala Met Tyr Phe Asp Asp Phe Tyr
            660                 665                 670

Val Val Asp Val Lys Pro Ala Glu Asp Leu Leu Ser Pro Glu Leu Ile
        675                 680                 685

Asn Pro Asn Ser Trp Ile Thr Thr Pro Gly Ala Ser Ile Ser Gly Asn
    690                 695                 700

Lys Leu Phe Ile Asn Leu Gly Thr Asn Gly Thr Phe Arg Gln Ser Leu
705                 710                 715                 720

Ser Leu Asn Ser Tyr Ser Thr Tyr Ser Ile Ser Phe Thr Ala Ser Gly
                725                 730                 735

Pro Phe Asn Val Thr Val Arg Asn Ser Arg Glu Val Leu Phe Glu Arg
            740                 745                 750

Ser Asn Leu Met Ser Ser Thr Ser His Ile Ser Gly Thr Phe Lys Thr
        755                 760                 765

Glu Ser Asn Asn Thr Gly Leu Tyr Val Glu Leu Ser Arg Arg Ser Gly
    770                 775                 780

Gly Gly Gly His Ile Ser Phe Glu Asn Val Ser Ile Lys
785                 790                 795

<210> SEQ ID NO 39
<211> LENGTH: 802
<212> TYPE: PRT
<213> ORGANISM: Artificial
<220> FEATURE:
<223> OTHER INFORMATION: Vip3Dd3_to_CenC sequence

<400> SEQUENCE: 39

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asn Leu Thr Leu
            35                  40                  45

Asp Glu Ile Leu Lys Asn Gln Gln Leu Leu Asn Glu Ile Ser Gly Lys
        50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110
```

```
Met Leu His Ile Tyr Leu Pro Lys Ile Thr Ser Met Leu Ser Asp Val
            115                 120                 125

Met Lys Gln Asn Tyr Ala Leu Ser Leu Gln Ile Glu Tyr Leu Ser Lys
        130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Met Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Thr Asp Lys Leu Phe
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Pro Gly Leu
```

```
                530             535             540
Glu Asp Gly Ile Asn Asn Trp Gln Ala Trp Gly Glu Gly Phe Thr Ala
545                 550             555                 560

Ala Ser Asp Met Ser His Thr Gly Ser Ala Ser Leu Lys Val Leu Leu
                565             570             575

Asn Asn Gly Gly Arg Gln Val Val Ala Leu Gln Pro Gly Lys Ser Tyr
            580             585             590

Lys Leu Gly Val Trp Gly Lys Thr Ala Gly Thr Gly Thr Gly Thr Gln
                595             600             605

Thr Ala Thr Val Met Ile Asn Tyr Lys Lys Pro Glu Asp Asp Ser Ser
610             615             620

His Thr Tyr Gly Ser Phe Gln Phe Gly Pro Asp Asn Ser Glu Phe Thr
625             630             635             640

Tyr Lys Glu Ile Thr Phe Glu Thr Pro Asp Asp Met Ala Gln Glu Trp
                645             650             655

Gly Thr Gln Phe Val Ser Ile Trp Ser Glu Gly Ala Asp Gln Val Tyr
            660             665             670

Leu Asp Asp Phe Thr Leu Ser Glu Val Lys Pro Ala Glu Asp Leu Leu
                675             680             685

Ser Pro Glu Leu Ile Asn Pro Asn Ser Trp Ile Thr Thr Pro Gly Ala
690             695             700

Ser Ile Ser Gly Asn Lys Leu Phe Ile Asn Leu Gly Thr Asn Gly Thr
705                 710             715                 720

Phe Arg Gln Ser Leu Ser Leu Asn Ser Tyr Ser Thr Tyr Ser Ile Ser
                725             730             735

Phe Thr Ala Ser Gly Pro Phe Asn Val Thr Val Arg Asn Ser Arg Glu
            740             745             750

Val Leu Phe Glu Arg Ser Asn Leu Met Ser Ser Thr Ser His Ile Ser
                755             760             765

Gly Thr Phe Lys Thr Glu Ser Asn Asn Thr Gly Leu Tyr Val Glu Leu
            770             775             780

Ser Arg Arg Ser Gly Gly Gly His Ile Ser Phe Glu Asn Val Ser
785             790             795             800

Ile Lys

<210> SEQ ID NO 40
<211> LENGTH: 795
<212> TYPE: PRT
<213> ORGANISM: Artificial
<220> FEATURE:
<223> OTHER INFORMATION: Vip3Dd3_to_PSHGF7 sequence

<400> SEQUENCE: 40

Met Asn Met Asn Asn Thr Lys Leu Asn Ala Arg Ala Leu Pro Ser Phe
1               5               10              15

Ile Asp Tyr Phe Asn Gly Ile Tyr Gly Phe Ala Thr Gly Ile Lys Asp
                20              25              30

Ile Met Asn Met Ile Phe Lys Thr Asp Thr Gly Gly Asn Leu Thr Leu
            35              40              45

Asp Glu Ile Leu Lys Asn Gln Gln Leu Leu Asn Glu Ile Ser Gly Lys
        50              55              60

Leu Asp Gly Val Asn Gly Ser Leu Asn Asp Leu Ile Ala Gln Gly Asn
65              70              75              80

Leu Asn Thr Glu Leu Ser Lys Glu Ile Leu Lys Ile Ala Asn Glu Gln
                85              90              95
```

```
Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
            115                 120                 125

Met Lys Gln Asn Tyr Ala Leu Ser Leu Gln Ile Glu Tyr Leu Ser Lys
            130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
            195                 200                 205

Leu Thr Glu Leu Thr Glu Leu Ala Lys Ser Val Thr Lys Asn Asp Val
            210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
            275                 280                 285

Leu Thr Thr Cys Arg Lys Leu Gly Leu Ala Asp Ile Asp Tyr Thr
            290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Met Ser Asn Asp Ser Ile Thr
            355                 360                 365

Val Leu Lys Val Tyr Glu Ala Lys Leu Lys Gln Asn Tyr Gln Val Asp
            370                 375                 380

Lys Asp Ser Leu Ser Glu Val Ile Tyr Gly Asp Thr Asp Lys Leu Phe
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Met Lys
            420                 425                 430

Thr Leu Arg Tyr Glu Val Thr Ala Asn Phe Tyr Asp Ser Ser Thr Gly
            435                 440                 445

Glu Ile Asp Leu Asn Lys Lys Val Glu Ser Ser Glu Ala Glu Tyr
            450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510
```

```
Glu Leu Leu Leu Ala Thr Asp Leu Ser Asn Lys Glu Thr Lys Leu Ile
            515                 520                 525

Val Pro Pro Ser Gly Phe Ile Ser Asn Ile Val Glu Asn Pro Gly Phe
530                 535                 540

Glu Asp Asn Leu Ala Ser Trp Thr Asn Trp Gly Asn Thr Ser Ser Val
545                 550                 555                 560

Thr Ser Pro Ala Phe Ala Gly Ala Lys Ala Ala Arg Ile Ala Ser Gly
                565                 570                 575

Glu Gly Gly Ala Gly Gln Ile Ile Pro Gly Ile Pro Ser Gly Thr Thr
            580                 585                 590

Tyr Val Leu Ser Gly His Gly Ser Val Ser Ala Gly Thr Asp Thr Ala
            595                 600                 605

Ile Val Gly Val Asp Cys Leu Asp Ala Asn Asn Asn Val Leu Ala Lys
            610                 615                 620

Asn Thr Leu Arg Phe Asn Gln Thr Leu Tyr Glu Phe Lys Ser Thr Ala
625                 630                 635                 640

Phe Thr Thr Val Pro Gly Thr Ala Lys Leu Gln Val Tyr Ile Tyr Lys
                645                 650                 655

Asn Ala Asp Ser Gly Ala Asn Ala Phe Leu Asp Asp Leu Ser Leu Val
                660                 665                 670

Glu Val Lys Pro Ala Glu Asp Leu Leu Ser Pro Glu Leu Ile Asn Pro
            675                 680                 685

Asn Ser Trp Ile Thr Thr Pro Gly Ala Ser Ile Ser Gly Asn Lys Leu
            690                 695                 700

Phe Ile Asn Leu Gly Thr Asn Gly Thr Phe Arg Gln Ser Leu Ser Leu
705                 710                 715                 720

Asn Ser Tyr Ser Thr Tyr Ser Ile Ser Phe Thr Ala Ser Gly Pro Phe
                725                 730                 735

Asn Val Thr Val Arg Asn Ser Arg Glu Val Leu Phe Glu Arg Ser Asn
                740                 745                 750

Leu Met Ser Ser Thr Ser His Ile Ser Gly Thr Phe Lys Thr Glu Ser
            755                 760                 765

Asn Asn Thr Gly Leu Tyr Val Glu Leu Ser Arg Arg Ser Gly Gly Gly
            770                 775                 780

Gly His Ile Ser Phe Glu Asn Val Ser Ile Lys
785                 790                 795

<210> SEQ ID NO 41
<211> LENGTH: 798
<212> TYPE: PRT
<213> ORGANISM: Artificial
<220> FEATURE:
<223> OTHER INFORMATION: Vip3Bd3_to_2ZEX sequence

<400> SEQUENCE: 41

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asn Leu Thr Leu
            35                  40                  45

Asp Glu Ile Leu Lys Asn Gln Gln Leu Leu Asn Glu Ile Ser Gly Lys
        50                  55                  60

Leu Asp Gly Val Asn Gly Ser Leu Asn Asp Leu Ile Ala Gln Gly Asn
65                  70                  75                  80
```

```
Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Val Glu Tyr Leu Ser Lys
    130                 135                 140

Gln Leu Lys Glu Ile Ser Asp Lys Leu Asp Val Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Ile Ser Asn Asp Ser Met Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Ser Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Ser Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
```

500                 505                 510
Glu Leu Leu Leu Ala Thr Asp Leu Ser Asn Lys Glu Thr Lys Leu Ile
                515                 520                 525
Val Pro Pro Ile Ser Phe Ile Ser Asn Ile Val Glu Asn Pro Gly Phe
            530                 535                 540
Glu Asp Gly Leu Asp Ser Trp Gln Asp Trp Gln Gln Asp Met Ser Ala
545                 550                 555                 560
Val Pro Glu Ala Ala His Asn Gly Ala Leu Gly Leu Lys Ile Gly Gly
                565                 570                 575
Gly Lys Ala Ala Gly Gly Gln Asp Ile Pro Leu Lys Pro Asn Thr
            580                 585                 590
Thr Tyr Ile Leu Gly Ala Trp Ala Lys Phe Asp Ser Lys Pro Ala Gly
                595                 600                 605
Thr Phe Asp Val Val Gln Tyr His Leu Lys Asp Ala Asn Asn Thr
            610                 615                 620
Tyr Val Gln His Ile Leu Asn Phe Asn Glu Thr Asp Trp Thr Tyr Lys
625                 630                 635                 640
Gln Leu Leu Phe Thr Thr Pro Asp Val Phe Gly Ser Thr Pro Gln Leu
                645                 650                 655
Ala Leu Trp Lys Gly Asp Thr Ser Lys Ala Asn Leu Tyr Val Asp Asp
                660                 665                 670
Val Tyr Leu Val Glu Val Arg Thr Ser Glu Glu Leu Leu Ser Pro Glu
            675                 680                 685
Leu Ile Met Ser Asp Ala Trp Val Gly Ser Gln Gly Thr Trp Ile Ser
            690                 695                 700
Gly Asn Ser Leu Thr Ile Asn Ser Asn Val Asn Gly Thr Phe Arg Gln
705                 710                 715                 720
Asn Leu Pro Leu Glu Ser Tyr Ser Thr Tyr Ser Met Asn Phe Thr Val
                725                 730                 735
Asn Gly Phe Gly Lys Val Thr Val Arg Asn Ser Arg Glu Val Leu Phe
            740                 745                 750
Glu Lys Ser Tyr Pro Gln Leu Ser Pro Lys Asp Ile Ser Glu Lys Phe
            755                 760                 765
Thr Thr Ala Ala Asn Asn Thr Gly Leu Tyr Val Glu Leu Ser Arg Ser
            770                 775                 780
Thr Ser Gly Gly Ala Ile Asn Phe Arg Asp Phe Ser Ile Lys
785                 790                 795

<210> SEQ ID NO 42
<211> LENGTH: 798
<212> TYPE: PRT
<213> ORGANISM: Artificial
<220> FEATURE:
<223> OTHER INFORMATION: Vip3Bd3_to_2ZEZ sequence

<400> SEQUENCE: 42

Met Asn Met Asn Asn Thr Lys Leu Asn Ala Arg Ala Leu Pro Ser Phe
1               5                   10                  15
Ile Asp Tyr Phe Asn Gly Ile Tyr Gly Phe Ala Thr Gly Ile Lys Asp
            20                  25                  30
Ile Met Asn Met Ile Phe Lys Thr Asp Thr Gly Gly Asn Leu Thr Leu
        35                  40                  45
Asp Glu Ile Leu Lys Asn Gln Gln Leu Leu Asn Glu Ile Ser Gly Lys
    50                  55                  60
Leu Asp Gly Val Asn Gly Ser Leu Asn Asp Leu Ile Ala Gln Gly Asn

```
                65                  70                  75                  80
Leu Asn Thr Glu Leu Ser Lys Glu Ile Leu Lys Ile Ala Asn Glu Gln
                    85                  90                  95

Asn Gln Val Leu Asn Asp Val Asn Lys Leu Asp Ala Ile Asn Thr
            100                 105                 110

Met Leu His Ile Tyr Leu Pro Lys Ile Thr Ser Met Leu Ser Asp Val
            115                 120                 125

Met Lys Gln Asn Tyr Ala Leu Ser Leu Gln Val Glu Tyr Leu Ser Lys
    130                 135                 140

Gln Leu Lys Glu Ile Ser Asp Lys Leu Asp Val Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
                180                 185                 190

Thr Leu Lys Val Lys Lys Asp Ser Ser Pro Ala Asp Ile Leu Asp Glu
            195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
    275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Ile Ser Asn Asp Ser Met Thr
            355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Ser Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Ser Tyr Asp Ser Ser Thr Gly
    435                 440                 445

Glu Ile Asp Leu Asn Lys Lys Val Glu Ser Glu Ala Glu Tyr
    450                 455                 460

Arg Thr Leu Ser Ala Asn Asn Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495
```

```
Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
            515                 520                 525

Val Pro Pro Ile Ser Phe Ile Ser Asn Ile Val Glu Asn Pro Gly Phe
            530                 535                 540

Glu Asn Gly Met Asp Gly Trp Pro Asp Trp Gly Tyr Pro Val Ser Ala
545                 550                 555                 560

Val Pro Glu Ala Ala Tyr Gly Thr Lys Gly Phe Lys Leu Ser Gly
            565                 570                 575

Gly Lys Gln Ala Gly Met Gly Gln Lys Val Ala Leu Lys Pro Asn Thr
            580                 585                 590

Thr Tyr Ile Leu Gly Ala Trp Gly Lys Phe Thr Ala Lys Pro Gly Thr
            595                 600                 605

Tyr Cys Asp Val Ile Val Gln Tyr His Leu Lys Asp Ala Asn Asn Thr
            610                 615                 620

Tyr Val Gln Asn Ile Leu Arg Phe Thr Glu Thr Asp Trp Thr Tyr Lys
625                 630                 635                 640

Gln Val Val Phe Thr Thr Pro Asp Ala Phe Gly Ser Asp Pro Glu Phe
            645                 650                 655

Val Leu Trp Lys Asp Asp Ala Ser Asn Ala Asp Phe Tyr Ala Asp Asn
            660                 665                 670

Ile Thr Leu Val Glu Val Arg Thr Ser Glu Glu Leu Leu Ser Pro Glu
            675                 680                 685

Leu Ile Met Ser Asp Ala Trp Val Gly Ser Gln Gly Thr Trp Ile Ser
            690                 695                 700

Gly Asn Ser Leu Thr Ile Asn Ser Asn Val Asn Gly Thr Phe Arg Gln
705                 710                 715                 720

Asn Leu Pro Leu Glu Ser Tyr Ser Thr Tyr Ser Met Asn Phe Thr Val
            725                 730                 735

Asn Gly Phe Gly Lys Val Thr Val Arg Asn Ser Arg Glu Val Leu Phe
            740                 745                 750

Glu Lys Ser Tyr Pro Gln Leu Ser Pro Lys Asp Ile Ser Glu Lys Phe
            755                 760                 765

Thr Thr Ala Ala Asn Asn Thr Gly Leu Tyr Val Glu Leu Ser Arg Ser
            770                 775                 780

Thr Ser Gly Gly Ala Ile Asn Phe Arg Asp Phe Ser Ile Lys
785                 790                 795

<210> SEQ ID NO 43
<211> LENGTH: 822
<212> TYPE: PRT
<213> ORGANISM: Artificial
<220> FEATURE:
<223> OTHER INFORMATION: Vip3Bd3_to_1OFE sequence

<400> SEQUENCE: 43

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
            35                  40                  45

Asp Glu Ile Leu Lys Asn Gln Gln Leu Leu Asn Glu Ile Ser Gly Lys
            50                  55                  60
```

```
Leu Asp Gly Val Asn Gly Ser Leu Asn Asp Leu Ile Ala Gln Gly Asn
 65                  70                  75                  80

Leu Asn Thr Glu Leu Ser Lys Glu Ile Leu Lys Ile Ala Asn Glu Gln
                 85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
            115                 120                 125

Met Lys Gln Asn Tyr Ala Leu Ser Leu Gln Val Glu Tyr Leu Ser Lys
            130                 135                 140

Gln Leu Lys Glu Ile Ser Asp Lys Leu Asp Val Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
            195                 200                 205

Leu Thr Glu Leu Thr Glu Leu Ala Lys Ser Val Thr Lys Asn Asp Val
210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
            275                 280                 285

Leu Thr Thr Cys Arg Lys Leu Leu Gly Leu Ala Asp Ile Asp Tyr Thr
            290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Ile Ser Asn Asp Ser Met Thr
            355                 360                 365

Val Leu Lys Val Tyr Glu Ala Lys Leu Lys Gln Asn Tyr Gln Val Asp
            370                 375                 380

Lys Asp Ser Leu Ser Glu Val Ile Tyr Ser Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Ser Tyr Asp Ser Ser Thr Gly
            435                 440                 445

Glu Ile Asp Leu Asn Lys Lys Lys Val Glu Ser Ser Glu Ala Glu Tyr
            450                 455                 460

Arg Thr Leu Ser Ala Asn Asn Asp Gly Val Tyr Met Pro Leu Gly Val
465                 470                 475                 480
```

Ile Ser Glu Thr Phe Leu Thr Pro Ile Asn Gly Phe Gly Leu Gln Ala
            485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
            515                 520                 525

Val Pro Pro Ile Ser Phe Ile Ser Asn Ile Val Glu Asn Asp Phe Ser
            530                 535                 540

Ser Pro Glu Glu Val Lys Asn Trp Trp Asn Ser Gly Thr Trp Gln Ala
545                 550                 555                 560

Glu Phe Gly Ser Pro Asp Ile Glu Trp Asn Gly Glu Val Gly Asn Gly
            565                 570                 575

Ala Leu Gln Leu Asn Val Lys Leu Pro Gly Lys Ser Asp Trp Glu Glu
            580                 585                 590

Val Arg Val Ala Arg Lys Phe Glu Arg Leu Ser Glu Cys Glu Ile Leu
            595                 600                 605

Glu Tyr Asp Ile Tyr Ile Pro Asn Val Glu Gly Leu Lys Gly Arg Leu
            610                 615                 620

Arg Pro Tyr Ala Val Leu Asn Pro Gly Trp Val Lys Ile Gly Leu Asp
625                 630                 635                 640

Met Asn Asn Ala Asn Val Glu Ser Ala Glu Ile Ile Thr Phe Gly Gly
            645                 650                 655

Lys Glu Tyr Arg Arg Phe His Val Arg Ile Glu Phe Asp Arg Thr Ala
            660                 665                 670

Gly Val Lys Glu Leu His Ile Gly Val Val Gly Asp His Leu Arg Tyr
            675                 680                 685

Asp Gly Pro Ile Phe Ile Asp Asn Val Arg Leu Tyr Lys Arg Arg Thr
            690                 695                 700

Ser Glu Glu Leu Leu Ser Pro Glu Leu Ile Met Ser Asp Ala Trp Val
705                 710                 715                 720

Gly Ser Gln Gly Thr Trp Ile Ser Gly Asn Ser Leu Thr Ile Asn Ser
            725                 730                 735

Asn Val Asn Gly Thr Phe Arg Gln Asn Leu Pro Leu Glu Ser Tyr Ser
            740                 745                 750

Thr Tyr Ser Met Asn Phe Thr Val Asn Gly Phe Gly Lys Val Thr Val
            755                 760                 765

Arg Asn Ser Arg Glu Val Leu Phe Glu Lys Ser Tyr Pro Gln Leu Ser
            770                 775                 780

Pro Lys Asp Ile Ser Glu Lys Phe Thr Thr Ala Ala Asn Asn Thr Gly
785                 790                 795                 800

Leu Tyr Val Glu Leu Ser Arg Ser Thr Ser Gly Gly Ala Ile Asn Phe
            805                 810                 815

Arg Asp Phe Ser Ile Lys
            820

<210> SEQ ID NO 44
<211> LENGTH: 876
<212> TYPE: PRT
<213> ORGANISM: Artificial
<220> FEATURE:
<223> OTHER INFORMATION: Vip3Bd3_to_1PMH sequence

<400> SEQUENCE: 44

Met Asn Met Asn Asn Thr Lys Leu Asn Ala Arg Ala Leu Pro Ser Phe
1               5                   10                  15

```
Ile Asp Tyr Phe Asn Gly Ile Tyr Phe Ala Thr Gly Ile Lys Asp
             20                  25                  30

Ile Met Asn Met Ile Phe Lys Thr Asp Thr Gly Gly Asn Leu Thr Leu
         35                  40                  45

Asp Glu Ile Leu Lys Asn Gln Gln Leu Leu Asn Glu Ile Ser Gly Lys
 50                  55                  60

Leu Asp Gly Val Asn Gly Ser Leu Asn Asp Leu Ile Ala Gln Gly Asn
 65                  70                  75                  80

Leu Asn Thr Glu Leu Ser Lys Glu Ile Leu Lys Ile Ala Asn Glu Gln
                 85                  90                  95

Asn Gln Val Leu Asn Asp Val Asn Asn Lys Leu Asp Ala Ile Asn Thr
             100                 105                 110

Met Leu His Ile Tyr Leu Pro Lys Ile Thr Ser Met Leu Ser Asp Val
         115                 120                 125

Met Lys Gln Asn Tyr Ala Leu Ser Leu Gln Val Glu Tyr Leu Ser Lys
     130                 135                 140

Gln Leu Lys Glu Ile Ser Asp Lys Leu Asp Val Ile Asn Val Asn Val
145                 150                 155                 160

Leu Ile Asn Ser Thr Leu Thr Glu Ile Thr Pro Ala Tyr Gln Arg Ile
                 165                 170                 175

Lys Tyr Val Asn Glu Lys Phe Glu Glu Leu Thr Phe Ala Thr Glu Thr
             180                 185                 190

Thr Leu Lys Val Lys Lys Asp Ser Pro Ala Asp Ile Leu Asp Glu
         195                 200                 205

Leu Thr Glu Leu Thr Glu Leu Ala Lys Ser Val Thr Lys Asn Asp Val
 210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                 245                 250                 255

Ala Lys Glu Asn Val Lys Thr Ser Gly Ser Glu Val Gly Asn Val Tyr
             260                 265                 270

Asn Phe Leu Ile Val Leu Thr Ala Leu Gln Ala Lys Ala Phe Leu Thr
         275                 280                 285

Leu Thr Thr Cys Arg Lys Leu Leu Gly Leu Ala Asp Ile Asp Tyr Thr
     290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                 325                 330                 335

Lys Val Lys Gly Ser Asp Glu Asp Ala Lys Met Ile Val Glu Ala Lys
             340                 345                 350

Pro Gly His Ala Leu Val Gly Phe Glu Ile Ser Asn Asp Ser Met Thr
         355                 360                 365

Val Leu Lys Val Tyr Glu Ala Lys Leu Lys Gln Asn Tyr Gln Val Asp
     370                 375                 380

Lys Asp Ser Leu Ser Glu Val Ile Tyr Ser Asp Met Asp Lys Leu Leu
385                 390                 395                 400

Cys Pro Asp Gln Ser Glu Gln Ile Tyr Tyr Thr Asn Asn Ile Val Phe
                 405                 410                 415

Pro Asn Glu Tyr Val Ile Thr Lys Ile Asp Phe Thr Lys Lys Met Lys
             420                 425                 430

Thr Leu Arg Tyr Glu Val Thr Ala Asn Ser Tyr Asp Ser Ser Thr Gly
```

```
            435                 440                 445
Glu Ile Asp Leu Asn Lys Lys Val Glu Ser Ser Glu Ala Glu Tyr
450                 455                 460

Arg Thr Leu Ser Ala Asn Asn Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
                515                 520                 525

Val Pro Pro Ile Ser Phe Ile Ser Asn Ile Val Glu Asn Asp Phe Glu
530                 535                 540

Asp Gly Thr Val Met Ser Phe Gly Glu Ala Trp Gly Asp Ser Leu Lys
545                 550                 555                 560

Cys Ile Lys Lys Val Ser Val Ser Gln Asp Leu Gln Arg Pro Gly Asn
                565                 570                 575

Lys Tyr Ala Leu Arg Leu Asp Val Glu Phe Asn Pro Asn Asn Gly Trp
                580                 585                 590

Asp Gln Gly Asp Leu Gly Thr Trp Ile Gly Val Glu Gly Gln
                595                 600                 605

Phe Asp Phe Thr Gly Tyr Lys Ser Val Glu Phe Glu Met Phe Ile Pro
610                 615                 620

Tyr Asp Glu Phe Ser Lys Ser Gln Gly Gly Phe Ala Tyr Lys Val Val
625                 630                 635                 640

Ile Asn Asp Gly Trp Lys Glu Leu Gly Ser Glu Phe Asn Ile Thr Ala
                645                 650                 655

Asn Ala Gly Lys Lys Val Lys Ile Asn Gly Lys Asp Tyr Thr Val Ile
                660                 665                 670

His Lys Ala Phe Ala Ile Pro Glu Asp Phe Arg Thr Lys Lys Arg Ala
                675                 680                 685

Gln Leu Val Phe Gln Phe Ala Gly Gln Asn Ser Asn Tyr Lys Gly Pro
                690                 695                 700

Ile Tyr Leu Asp Asn Val Arg Ile Arg Pro Glu Phe His Val Arg Ile
705                 710                 715                 720

Glu Phe Asp Arg Thr Ala Gly Val Lys Glu Leu His Ile Gly Val Val
                725                 730                 735

Gly Asp His Leu Arg Tyr Asp Gly Pro Ile Phe Ile Asp Asn Val Arg
                740                 745                 750

Leu Tyr Lys Arg Arg Thr Ser Glu Glu Leu Leu Ser Pro Glu Leu Ile
                755                 760                 765

Met Ser Asp Ala Trp Val Ser Gln Gly Thr Trp Ile Ser Gly Asn
                770                 775                 780

Ser Leu Thr Ile Asn Ser Asn Val Asn Gly Thr Phe Arg Gln Asn Leu
785                 790                 795                 800

Pro Leu Glu Ser Tyr Ser Thr Tyr Ser Met Asn Phe Thr Val Asn Gly
                805                 810                 815

Phe Gly Lys Val Thr Val Arg Asn Ser Arg Glu Val Leu Phe Glu Lys
                820                 825                 830

Ser Tyr Pro Gln Leu Ser Pro Lys Asp Ile Ser Glu Lys Phe Thr Thr
                835                 840                 845

Ala Ala Asn Asn Thr Gly Leu Tyr Val Glu Leu Ser Arg Ser Thr Ser
850                 855                 860
```

```
Gly Gly Ala Ile Asn Phe Arg Asp Phe Ser Ile Lys
865                 870                 875

<210> SEQ ID NO 45
<211> LENGTH: 773
<212> TYPE: PRT
<213> ORGANISM: Artificial
<220> FEATURE:
<223> OTHER INFORMATION: Vip3Bd3_to_2BGP sequence

<400> SEQUENCE: 45

Met Asn Met Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65              70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Val Glu Tyr Leu Ser Lys
    130                 135                 140

Gln Leu Lys Glu Ile Ser Asp Lys Leu Asp Val Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350
```

```
Pro Gly His Ala Leu Val Gly Phe Glu Ile Ser Asn Asp Ser Met Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Ser Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Ser Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asn Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ile Ser Phe Ile Ser Asn Ile Val Glu Asn Thr Ala Ala
    530                 535                 540

Ser Ala Ser Ile Thr Ala Pro Ala Gln Leu Val Gly Asn Val Gly Glu
545                 550                 555                 560

Leu Gln Gly Ala Gly Ser Ala Val Ile Trp Asn Val Asp Val Pro Val
                565                 570                 575

Thr Gly Glu Tyr Arg Ile Asn Leu Thr Trp Ser Ser Pro Tyr Ser Ser
            580                 585                 590

Lys Val Asn Thr Leu Val Met Asp Gly Thr Ala Leu Ser Tyr Ala Phe
        595                 600                 605

Ala Glu Ala Thr Val Pro Val Thr Tyr Val Gln Thr Lys Thr Leu Ser
    610                 615                 620

Ala Gly Asn His Ser Phe Gly Val Arg Val Gly Ser Ser Asp Trp Gly
625                 630                 635                 640

Tyr Met Asn Val His Ser Leu Lys Leu Glu Leu Leu Gly Arg Thr Ser
                645                 650                 655

Glu Glu Leu Leu Ser Pro Glu Leu Ile Met Ser Asp Ala Trp Val Gly
            660                 665                 670

Ser Gln Gly Thr Trp Ile Ser Gly Asn Ser Leu Thr Ile Asn Ser Asn
        675                 680                 685

Val Asn Gly Thr Phe Arg Gln Asn Leu Pro Leu Glu Ser Tyr Ser Thr
    690                 695                 700

Tyr Ser Met Asn Phe Thr Val Asn Gly Phe Gly Lys Val Thr Val Arg
705                 710                 715                 720

Asn Ser Arg Glu Val Leu Phe Glu Lys Ser Tyr Pro Gln Leu Ser Pro
                725                 730                 735

Lys Asp Ile Ser Glu Lys Phe Thr Thr Ala Ala Asn Asn Thr Gly Leu
            740                 745                 750

Tyr Val Glu Leu Ser Arg Ser Thr Ser Gly Gly Ala Ile Asn Phe Arg
        755                 760                 765
```

-continued

Asp Phe Ser Ile Lys
    770

<210> SEQ ID NO 46
<211> LENGTH: 796
<212> TYPE: PRT
<213> ORGANISM: Artificial
<220> FEATURE:
<223> OTHER INFORMATION: Vip3Bd3_to_GP21 sequence

<400> SEQUENCE: 46

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln

-continued

```
Pro Gly His Ala Leu Val Gly Phe Glu Ile Ser Asn Asp Ser Met Thr
            355                 360                 365
Val Leu Lys Val Tyr Glu Ala Lys Leu Lys Gln Asn Tyr Gln Val Asp
    370                 375                 380
Lys Asp Ser Leu Ser Glu Val Ile Tyr Ser Asp Met Asp Lys Leu Leu
385                 390                 395                 400
Cys Pro Asp Gln Ser Glu Gln Ile Tyr Thr Asn Asn Ile Val Phe
            405                 410                 415
Pro Asn Glu Tyr Val Ile Thr Lys Ile Asp Phe Thr Lys Lys Met Lys
            420                 425                 430
Thr Leu Arg Tyr Glu Val Thr Ala Asn Ser Tyr Asp Ser Ser Thr Gly
            435                 440                 445
Glu Ile Asp Leu Asn Lys Lys Lys Val Glu Ser Ser Glu Ala Glu Tyr
    450                 455                 460
Arg Thr Leu Ser Ala Asn Asn Asp Gly Val Tyr Met Pro Leu Gly Val
465                 470                 475                 480
Ile Ser Glu Thr Phe Leu Thr Pro Ile Asn Gly Phe Gly Leu Gln Ala
            485                 490                 495
Asp Glu Asn Ser Arg Leu Ile Thr Leu Thr Cys Lys Ser Tyr Leu Arg
            500                 505                 510
Glu Leu Leu Leu Ala Thr Asp Leu Ser Asn Lys Glu Thr Lys Leu Ile
            515                 520                 525
Val Pro Pro Ile Ser Phe Ile Ser Asn Ile Val Glu Asn Pro Ser Phe
            530                 535                 540
Glu Arg Gly Thr Glu Gly Tyr Thr Gly Trp Ser Gly Ile Ala Thr Val
545                 550                 555                 560
Val Thr Leu Gln Val Pro His Leu Gly Thr Lys Ala Ala Lys Leu Ala
            565                 570                 575
Ala Gly Gly Ser Ala Gly Val Gly Gln Lys Ile Ser Phe Lys Lys Asp
            580                 585                 590
Arg Ser Tyr Lys Ile Gly Ile Trp Ala Lys Gln Asp Pro Asn Thr Thr
            595                 600                 605
Ile Gln Ser Thr Asp Asn Thr Lys Phe Arg Val Ala Asp Gly Asn Gly
    610                 615                 620
Leu Ile Ala Ser Lys Ala Tyr Gly Pro Phe Thr Ser Asn Trp Gln Glu
625                 630                 635                 640
Val Ser Trp Thr Trp Lys Ala Thr Lys Asp Val Leu Ala Asp Val Gln
            645                 650                 655
Phe Thr Ala Phe Leu Ser Ala Gly Ala Met Tyr Phe Asp Phe Tyr
            660                 665                 670
Val Val Asp Val Arg Thr Ser Glu Glu Leu Leu Ser Pro Glu Leu Ile
            675                 680                 685
Met Ser Asp Ala Trp Val Gly Ser Gln Gly Thr Trp Ile Ser Gly Asn
            690                 695                 700
Ser Leu Thr Ile Asn Ser Asn Val Asn Gly Thr Phe Arg Gln Asn Leu
705                 710                 715                 720
Pro Leu Glu Ser Tyr Ser Thr Tyr Ser Met Asn Phe Thr Val Asn Gly
            725                 730                 735
Phe Gly Lys Val Thr Val Arg Asn Ser Arg Glu Val Leu Phe Glu Lys
            740                 745                 750
Ser Tyr Pro Gln Leu Ser Pro Lys Asp Ile Ser Glu Lys Phe Thr Thr
            755                 760                 765
Ala Ala Asn Asn Thr Gly Leu Tyr Val Glu Leu Ser Arg Ser Thr Ser
```

```
                  770                 775                 780
Gly Gly Ala Ile Asn Phe Arg Asp Phe Ser Ile Lys
785                 790                 795

<210> SEQ ID NO 47
<211> LENGTH: 801
<212> TYPE: PRT
<213> ORGANISM: Artificial
<220> FEATURE:
<223> OTHER INFORMATION: Vip3Bd3_to_CenC sequence

<400> SEQUENCE: 47

Met Asn Met Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile

```
                340                 345                 350
Pro Gly His Ala Leu Val Gly Phe Glu Ile Ser Asn Asp Ser Met Thr
                355                 360                 365
Val Leu Lys Val Tyr Glu Ala Lys Leu Lys Gln Asn Tyr Gln Val Asp
                370                 375                 380
Lys Asp Ser Leu Ser Glu Val Ile Tyr Ser Asp Met Asp Lys Leu Leu
385                 390                 395                 400
Cys Pro Asp Gln Ser Glu Gln Ile Tyr Tyr Thr Asn Asn Ile Val Phe
                405                 410                 415
Pro Asn Glu Tyr Val Ile Thr Lys Ile Asp Phe Thr Lys Lys Met Lys
                420                 425                 430
Thr Leu Arg Tyr Glu Val Thr Ala Asn Ser Tyr Asp Ser Ser Thr Gly
                435                 440                 445
Glu Ile Asp Leu Asn Lys Lys Val Glu Ser Glu Ala Glu Tyr
                450                 455                 460
Arg Thr Leu Ser Ala Asn Asn Asp Gly Val Tyr Met Pro Leu Gly Val
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
                500                 505                 510
Glu Leu Leu Leu Ala Thr Asp Leu Ser Asn Lys Glu Thr Lys Leu Ile
                515                 520                 525
Val Pro Pro Ile Ser Phe Ile Ser Asn Ile Val Glu Asn Pro Gly Leu
                530                 535                 540
Glu Asp Gly Ile Asn Asn Trp Gln Ala Trp Gly Gly Phe Thr Ala
545                 550                 555                 560
Ala Ser Asp Met Ser His Thr Gly Ser Ala Ser Leu Lys Val Leu Leu
                565                 570                 575
Asn Asn Gly Gly Arg Gln Val Val Ala Leu Gln Pro Gly Lys Ser Tyr
                580                 585                 590
Lys Leu Gly Val Trp Gly Lys Thr Ala Gly Thr Gly Thr Gln
                595                 600                 605
Thr Ala Thr Val Met Ile Asn Tyr Lys Lys Pro Glu Asp Ser Ser
                610                 615                 620
His Thr Tyr Gly Ser Phe Gln Phe Gly Pro Asp Asn Ser Glu Phe Thr
625                 630                 635                 640
Tyr Lys Glu Ile Thr Phe Glu Thr Pro Asp Asp Met Ala Gln Glu Trp
                645                 650                 655
Gly Thr Gln Phe Val Ser Ile Trp Ser Glu Gly Ala Asp Gln Val Tyr
                660                 665                 670
Leu Asp Asp Phe Thr Leu Ser Glu Val Arg Thr Ser Glu Glu Leu Leu
                675                 680                 685
Ser Pro Glu Leu Ile Met Ser Asp Ala Trp Val Gly Ser Gln Gly Thr
                690                 695                 700
Trp Ile Ser Gly Asn Ser Leu Thr Ile Asn Ser Asn Val Asn Gly Thr
705                 710                 715                 720
Phe Arg Gln Asn Leu Pro Leu Glu Ser Tyr Ser Thr Tyr Ser Met Asn
                725                 730                 735
Phe Thr Val Asn Gly Phe Gly Lys Val Thr Val Arg Asn Ser Arg Glu
                740                 745                 750
Val Leu Phe Glu Lys Ser Tyr Pro Gln Leu Ser Pro Lys Asp Ile Ser
                755                 760                 765
```

```
Glu Lys Phe Thr Thr Ala Ala Asn Asn Thr Gly Leu Tyr Val Glu Leu
    770             775                 780

Ser Arg Ser Thr Ser Gly Gly Ala Ile Asn Phe Arg Asp Phe Ser Ile
785             790                 795                 800

Lys

<210> SEQ ID NO 48
<211> LENGTH: 794
<212> TYPE: PRT
<213> ORGANISM: Artificial
<220> FEATURE:
<223> OTHER INFORMATION: Vip3Bd3_to_PSHGF7 sequence

<400> SEQUENCE: 48

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Asn Glu Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Val Glu Tyr Leu Ser Lys
130                 135                 140

Gln Leu Lys Glu Ile Ser Asp Lys Leu Asp Val Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
290                 295                 300

Ser Ile Met Asn Glu His Leu Asn Lys Glu Lys Glu Glu Phe Arg Val
305                 310                 315                 320
```

-continued

Asn Ile Leu Pro Thr Leu Ser Asn Thr Phe Ser Asn Pro Asn Tyr Ala
            325                 330                 335

Lys Val Lys Gly Ser Asp Glu Asp Ala Lys Met Ile Val Glu Ala Lys
        340                 345                 350

Pro Gly His Ala Leu Val Gly Phe Glu Ile Ser Asn Asp Ser Met Thr
            355                 360                 365

Val Leu Lys Val Tyr Glu Ala Lys Leu Lys Gln Asn Tyr Gln Val Asp
        370                 375                 380

Lys Asp Ser Leu Ser Glu Val Ile Tyr Ser Met Asp Lys Leu Leu
385                 390                 395                 400

Cys Pro Asp Gln Ser Glu Gln Ile Tyr Tyr Thr Asn Asn Ile Val Phe
            405                 410                 415

Pro Asn Glu Tyr Val Ile Thr Lys Ile Asp Phe Thr Lys Lys Met Lys
        420                 425                 430

Thr Leu Arg Tyr Glu Val Thr Ala Asn Ser Tyr Asp Ser Ser Thr Gly
            435                 440                 445

Glu Ile Asp Leu Asn Lys Lys Lys Val Glu Ser Glu Ala Glu Tyr
        450                 455                 460

Arg Thr Leu Ser Ala Asn Asn Asp Gly Val Tyr Met Pro Leu Gly Val
465                 470                 475                 480

Ile Ser Glu Thr Phe Leu Thr Pro Ile Asn Gly Phe Gly Leu Gln Ala
            485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
            515                 520                 525

Val Pro Pro Ile Ser Phe Ile Ser Asn Ile Val Glu Asn Pro Gly Phe
        530                 535                 540

Glu Asp Asn Leu Ala Ser Trp Thr Asn Trp Gly Asn Thr Ser Ser Val
545                 550                 555                 560

Thr Ser Pro Ala Phe Ala Gly Ala Lys Ala Ala Arg Ile Ala Ser Gly
            565                 570                 575

Glu Gly Gly Ala Gly Gln Ile Ile Pro Gly Ile Pro Ser Gly Thr Thr
            580                 585                 590

Tyr Val Leu Ser Gly His Gly Ser Val Ser Ala Gly Thr Asp Thr Ala
            595                 600                 605

Ile Val Gly Val Asp Cys Leu Asp Ala Asn Asn Val Leu Ala Lys
        610                 615                 620

Asn Thr Leu Arg Phe Asn Gln Thr Leu Tyr Glu Phe Lys Ser Thr Ala
625                 630                 635                 640

Phe Thr Thr Val Pro Gly Thr Ala Lys Leu Gln Val Tyr Ile Tyr Lys
            645                 650                 655

Asn Ala Asp Ser Gly Ala Asn Ala Phe Leu Asp Asp Leu Ser Leu Val
            660                 665                 670

Glu Val Arg Thr Ser Glu Glu Leu Leu Ser Pro Glu Leu Ile Met Ser
            675                 680                 685

Asp Ala Trp Val Gly Ser Gln Gly Thr Trp Ile Ser Gly Asn Ser Leu
        690                 695                 700

Thr Ile Asn Ser Asn Val Asn Gly Thr Phe Arg Gln Asn Leu Pro Leu
705                 710                 715                 720

Glu Ser Tyr Ser Thr Tyr Ser Met Asn Phe Thr Val Asn Gly Phe Gly
            725                 730                 735

Lys Val Thr Val Arg Asn Ser Arg Glu Val Leu Phe Glu Lys Ser Tyr

```
                    740                 745                 750
Pro Gln Leu Ser Pro Lys Asp Ile Ser Glu Lys Phe Thr Thr Ala Ala
            755                 760                 765

Asn Asn Thr Gly Leu Tyr Val Glu Leu Ser Arg Ser Thr Ser Gly Gly
            770                 775                 780

Ala Ile Asn Phe Arg Asp Phe Ser Ile Lys
785                 790
```

<210> SEQ ID NO 49
<211> LENGTH: 814
<212> TYPE: PRT
<213> ORGANISM: Artificial
<220> FEATURE:
<223> OTHER INFORMATION: Vip3Cd3_to_2ZEX sequence

<400> SEQUENCE: 49

```
Met Asn Lys Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asp Leu Thr Leu
            35                  40                  45

Asp Glu Ile Leu Lys Asn Gln Gln Leu Leu Asn Glu Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Asn Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Arg
    130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
        195                 200                 205

Asn Thr Leu Glu Asn Leu Thr Asp Leu Ala Glu Leu Ala Lys Ser Ile
    210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
            260                 265                 270

Ile Gly Lys Val Tyr Ser Phe Leu Ile Val Leu Thr Ser Leu Gln Ala
        275                 280                 285

Lys Ala Phe Leu Thr Leu Thr Thr Cys Arg Lys Leu Leu Gly Leu Ser
    290                 295                 300

Asp Ile Asp Tyr Thr Ser Ile Met Asn Glu His Leu Asn Asn Glu Lys
```

```
            305                 310                 315                 320
Asn Glu Phe Arg Asp Asn Ile Leu Pro Ala Leu Ser Asn Lys Phe Ser
                325                 330                 335
Asn Pro Ser Tyr Ala Lys Thr Ile Gly Ser Asp Asn Tyr Ala Lys Val
                340                 345                 350
Ile Leu Glu Ser Glu Pro Gly Tyr Ala Leu Val Gly Phe Glu Ile Ile
                355                 360                 365
Asn Asp Pro Ile Pro Val Leu Lys Ala Tyr Lys Ala Lys Leu Lys Gln
370                 375                 380
Asn Tyr Gln Val Asp Asn Gln Ser Leu Ser Glu Ile Val Tyr Leu Asp
385                 390                 395                 400
Ile Asp Lys Leu Phe Cys Pro Glu Asn Ser Glu Gln Lys Tyr Tyr Thr
                405                 410                 415
Lys Asn Leu Thr Phe Pro Asp Gly Tyr Val Ile Thr Lys Ile Thr Phe
                420                 425                 430
Glu Lys Lys Leu Asn Asn Leu Ile Tyr Glu Ala Thr Ala Asn Phe Tyr
                435                 440                 445
Asp Pro Ser Thr Gly Asp Ile Asp Leu Asn Lys Lys Gln Val Glu Ser
                450                 455                 460
Thr Phe Pro Gln Thr Asp Tyr Ile Thr Met Asp Ile Gly Asp Asp Asp
465                 470                 475                 480
Gly Ile Tyr Met Pro Leu Gly Val Ile Ser Glu Thr Phe Leu Thr Pro
                485                 490                 495
Ile Asn Ser Phe Gly Leu Glu Val Asp Ala Lys Ser Lys Thr Leu Thr
                500                 505                 510
Leu Lys Cys Lys Ser Tyr Leu Arg Glu Tyr Leu Leu Glu Ser Asp Leu
                515                 520                 525
Lys Asn Lys Glu Thr Gly Leu Ile Ala Pro Pro Asn Val Phe Ile Ser
                530                 535                 540
Asn Val Val Lys Asn Pro Gly Phe Glu Asp Gly Leu Asp Ser Trp Gln
545                 550                 555                 560
Asp Trp Gln Gln Asp Met Ser Ala Val Pro Glu Ala Ala His Asn Gly
                565                 570                 575
Ala Leu Gly Leu Lys Ile Gly Gly Lys Ala Ala Gly Gly Gly Gln
                580                 585                 590
Asp Ile Pro Leu Lys Pro Asn Thr Thr Tyr Ile Leu Gly Ala Trp Ala
                595                 600                 605
Lys Phe Asp Ser Lys Pro Ala Gly Thr Phe Asp Val Val Val Gln Tyr
                610                 615                 620
His Leu Lys Asp Ala Asn Asn Thr Tyr Val Gln His Ile Leu Asn Phe
625                 630                 635                 640
Asn Glu Thr Asp Trp Thr Tyr Lys Gln Leu Leu Phe Thr Thr Pro Asp
                645                 650                 655
Val Phe Gly Ser Thr Pro Gln Leu Ala Leu Trp Lys Gly Asp Thr Ser
                660                 665                 670
Lys Ala Asn Leu Tyr Val Asp Asp Val Tyr Leu Val Glu Val Lys Leu
                675                 680                 685
Phe Glu Thr Pro Glu Ser Pro Glu Leu Ile Lys Phe Asn Asp Trp Glu
                690                 695                 700
Arg Phe Gly Thr Thr Tyr Ile Thr Gly Asn Glu Leu Arg Ile Asp His
705                 710                 715                 720
Ser Arg Gly Gly Tyr Phe Arg Gln Ser Leu Asn Ile Asp Ser Tyr Ser
                725                 730                 735
```

```
Thr Tyr Asp Leu Ser Phe Ser Phe Ser Gly Leu Trp Ala Lys Val Ile
            740                 745                 750

Val Lys Asn Ser Arg Gly Val Val Leu Phe Glu Lys Val Lys Asn Asn
            755                 760                 765

Gly Ser Ser Tyr Glu Asp Ile Ser Glu Ser Phe Thr Thr Ala Ser Asn
            770                 775                 780

Lys Asp Gly Phe Phe Ile Glu Leu Thr Ala Glu Arg Thr Ser Ser Thr
785                 790                 795                 800

Phe His Ser Phe Arg Asp Ile Ser Ile Lys Glu Lys Ile Glu
                805                 810

<210> SEQ ID NO 50
<211> LENGTH: 814
<212> TYPE: PRT
<213> ORGANISM: Artificial
<220> FEATURE:
<223> OTHER INFORMATION: Vip3Cd3_to_2ZEZ sequence

<400> SEQUENCE: 50

Met Asn Lys Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Lys Ala Phe Leu Thr Leu Thr Thr Cys Arg Lys Leu Leu Gly Leu Ser
    290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
                340                 345                 350

Ile Leu Glu Ser Glu Pro Gly Tyr Ala Leu Val Gly Phe Glu Ile Ile
            355                 360                 365

Asn Asp Pro Ile Pro Val Leu Lys Ala Tyr Lys Ala Lys Leu Lys Gln
    370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415

Lys Asn Leu Thr Phe Pro Asp Gly Tyr Val Ile Thr Lys Ile Thr Phe
                420                 425                 430

Glu Lys Lys Leu Asn Asn Leu Ile Tyr Glu Ala Thr Ala Asn Phe Tyr
            435                 440                 445

Asp Pro Ser Thr Gly Asp Ile Asp Leu Asn Lys Lys Gln Val Glu Ser
    450                 455                 460

Thr Phe Pro Gln Thr Asp Tyr Ile Thr Met Asp Ile Gly Asp Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
                500                 505                 510

Leu Lys Cys Lys Ser Tyr Leu Arg Glu Tyr Leu Leu Glu Ser Asp Leu
            515                 520                 525

Lys Asn Lys Glu Thr Gly Leu Ile Ala Pro Pro Asn Val Phe Ile Ser
    530                 535                 540

Asn Val Val Lys Asn Pro Gly Phe Glu Asn Gly Met Asp Gly Trp Pro
545                 550                 555                 560

Asp Trp Gly Tyr Pro Val Ser Ala Val Pro Glu Ala Ala Tyr Gly Gly
                565                 570                 575

Thr Lys Gly Phe Lys Leu Ser Gly Gly Lys Gln Ala Gly Met Gly Gln
                580                 585                 590

Lys Val Ala Leu Lys Pro Asn Thr Thr Tyr Ile Leu Gly Ala Trp Gly
            595                 600                 605

Lys Phe Thr Ala Lys Pro Gly Thr Tyr Cys Asp Val Ile Val Gln Tyr
    610                 615                 620

His Leu Lys Asp Ala Asn Asn Thr Tyr Val Gln Asn Ile Leu Arg Phe
625                 630                 635                 640

Thr Glu Thr Asp Trp Thr Tyr Lys Gln Val Phe Thr Thr Pro Asp
                645                 650                 655

Ala Phe Gly Ser Asp Pro Glu Phe Val Leu Trp Lys Asp Ala Ser
                660                 665                 670

Asn Ala Asp Phe Tyr Ala Asp Asn Ile Thr Leu Val Glu Val Lys Leu
            675                 680                 685

Phe Glu Thr Pro Glu Ser Pro Glu Leu Ile Lys Phe Asn Asp Trp Glu
    690                 695                 700

```
Arg Phe Gly Thr Thr Tyr Ile Thr Gly Asn Glu Leu Arg Ile Asp His
705                 710                 715                 720

Ser Arg Gly Gly Tyr Phe Arg Gln Ser Leu Asn Ile Asp Ser Tyr Ser
            725                 730                 735

Thr Tyr Asp Leu Ser Phe Ser Phe Ser Gly Leu Trp Ala Lys Val Ile
                740                 745                 750

Val Lys Asn Ser Arg Gly Val Val Leu Phe Glu Lys Val Lys Asn Asn
        755                 760                 765

Gly Ser Ser Tyr Glu Asp Ile Ser Glu Ser Phe Thr Thr Ala Ser Asn
        770                 775                 780

Lys Asp Gly Phe Phe Ile Glu Leu Thr Ala Glu Arg Thr Ser Ser Thr
785                 790                 795                 800

Phe His Ser Phe Arg Asp Ile Ser Ile Lys Glu Lys Ile Glu
                805                 810
```

<210> SEQ ID NO 51
<211> LENGTH: 838
<212> TYPE: PRT
<213> ORGANISM: Artificial
<220> FEATURE:
<223> OTHER INFORMATION: Vip3Cd3_to_1OFE sequence

<400> SEQUENCE: 51

```
Met Asn Lys Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Glu Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
            85                  90                  95

Asn Gln Val Leu Asn Asp Val Asn Asn Lys Leu Asp Ala Ile Asn Thr
            100                 105                 110

Met Leu Asn Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Arg
130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
        195                 200                 205

Asn Thr Leu Glu Asn Leu Thr Asp Leu Ala Glu Leu Ala Lys Ser Ile
    210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255
```

```
Ala Ser Glu Leu Ile Thr Lys Asp Glu Ile Lys Thr Ser Gly Ser Glu
            260                 265                 270

Ile Gly Lys Val Tyr Ser Phe Leu Ile Val Leu Thr Ser Leu Gln Ala
        275                 280                 285

Lys Ala Phe Leu Thr Leu Thr Thr Cys Arg Lys Leu Leu Gly Leu Ser
    290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
            340                 345                 350

Ile Leu Glu Ser Glu Pro Gly Tyr Ala Leu Val Gly Phe Glu Ile Ile
        355                 360                 365

Asn Asp Pro Ile Pro Val Leu Lys Ala Tyr Lys Ala Lys Leu Lys Gln
    370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415

Lys Asn Leu Thr Phe Pro Asp Gly Tyr Val Ile Thr Lys Ile Thr Phe
            420                 425                 430

Glu Lys Lys Leu Asn Asn Leu Ile Tyr Glu Ala Thr Ala Asn Phe Tyr
        435                 440                 445

Asp Pro Ser Thr Gly Asp Ile Asp Leu Asn Lys Lys Gln Val Glu Ser
    450                 455                 460

Thr Phe Pro Gln Thr Asp Tyr Ile Thr Met Asp Ile Gly Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
            500                 505                 510

Leu Lys Cys Lys Ser Tyr Leu Arg Glu Tyr Leu Leu Glu Ser Asp Leu
        515                 520                 525

Lys Asn Lys Glu Thr Gly Leu Ile Ala Pro Pro Asn Val Phe Ile Ser
    530                 535                 540

Asn Val Val Lys Asn Asp Phe Ser Ser Pro Glu Glu Val Lys Asn Trp
545                 550                 555                 560

Trp Asn Ser Gly Thr Trp Gln Ala Glu Phe Gly Ser Pro Asp Ile Glu
                565                 570                 575

Trp Asn Gly Glu Val Gly Asn Gly Ala Leu Gln Leu Asn Val Lys Leu
            580                 585                 590

Pro Gly Lys Ser Asp Trp Glu Glu Val Arg Val Ala Arg Lys Phe Glu
        595                 600                 605

Arg Leu Ser Glu Cys Glu Ile Leu Glu Tyr Asp Ile Tyr Ile Pro Asn
    610                 615                 620

Val Glu Gly Leu Lys Gly Arg Leu Arg Pro Tyr Ala Val Leu Asn Pro
625                 630                 635                 640

Gly Trp Val Lys Ile Gly Leu Asp Met Asn Asn Ala Asn Val Glu Ser
                645                 650                 655

Ala Glu Ile Ile Thr Phe Gly Gly Lys Glu Tyr Arg Arg Phe His Val
            660                 665                 670

Arg Ile Glu Phe Asp Arg Thr Ala Gly Val Lys Glu Leu His Ile Gly
```

```
                    675                 680                 685
Val Val Gly Asp His Leu Arg Tyr Asp Gly Pro Ile Phe Ile Asp Asn
690                 695                 700

Val Arg Leu Tyr Lys Arg Lys Leu Phe Glu Thr Pro Glu Ser Pro Glu
705                 710                 715                 720

Leu Ile Lys Phe Asn Asp Trp Glu Arg Phe Gly Thr Thr Tyr Ile Thr
                    725                 730                 735

Gly Asn Glu Leu Arg Ile Asp His Ser Arg Gly Gly Tyr Phe Arg Gln
                740                 745                 750

Ser Leu Asn Ile Asp Ser Tyr Ser Thr Tyr Asp Leu Ser Phe Ser Phe
                755                 760                 765

Ser Gly Leu Trp Ala Lys Val Ile Val Lys Asn Ser Arg Gly Val Val
770                 775                 780

Leu Phe Glu Lys Val Lys Asn Asn Gly Ser Ser Tyr Glu Asp Ile Ser
785                 790                 795                 800

Glu Ser Phe Thr Thr Ala Ser Asn Lys Asp Gly Phe Phe Ile Glu Leu
                    805                 810                 815

Thr Ala Glu Arg Thr Ser Ser Thr Phe His Ser Phe Arg Asp Ile Ser
                820                 825                 830

Ile Lys Glu Lys Ile Glu
            835

<210> SEQ ID NO 52
<211> LENGTH: 851
<212> TYPE: PRT
<213> ORGANISM: Artificial
<220> FEATURE:
<223> OTHER INFORMATION: Vip3Cd3_to_1PMH sequence

<400> SEQUENCE: 52

Met Asn Lys Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asp Leu Thr Leu
            35                  40                  45

Asp Glu Ile Leu Lys Asn Gln Gln Leu Leu Asn Glu Ile Ser Gly Lys
        50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Asn Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Arg
    130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Thr Glu Ser
            180                 185                 190

Thr Leu Arg Ala Lys Gln Gly Ile Phe Asn Glu Asp Ser Phe Asp Asn
```

```
            195                 200                 205
Asn Thr Leu Glu Asn Leu Thr Asp Leu Ala Glu Leu Ala Lys Ser Ile
210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                    245                 250                 255

Ala Ser Glu Leu Ile Thr Lys Asp Glu Ile Lys Thr Ser Gly Ser Glu
                260                 265                 270

Ile Gly Lys Val Tyr Ser Phe Leu Ile Val Leu Thr Ser Leu Gln Ala
            275                 280                 285

Lys Ala Phe Leu Thr Leu Thr Thr Cys Arg Lys Leu Leu Gly Leu Ser
290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                    325                 330                 335

Asn Pro Ser Tyr Ala Lys Thr Ile Gly Ser Asp Asn Tyr Ala Lys Val
                340                 345                 350

Ile Leu Glu Ser Glu Pro Gly Tyr Ala Leu Val Gly Phe Glu Ile Ile
            355                 360                 365

Asn Asp Pro Ile Pro Val Leu Lys Ala Tyr Lys Ala Lys Leu Lys Gln
370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                    405                 410                 415

Lys Asn Leu Thr Phe Pro Asp Gly Tyr Val Ile Thr Lys Ile Thr Phe
                420                 425                 430

Glu Lys Lys Leu Asn Asn Leu Ile Tyr Glu Ala Thr Ala Asn Phe Tyr
            435                 440                 445

Asp Pro Ser Thr Gly Asp Ile Asp Leu Asn Lys Lys Gln Val Glu Ser
450                 455                 460

Thr Phe Pro Gln Thr Asp Tyr Ile Thr Met Asp Ile Gly Asp Asp Asp
465                 470                 475                 480

Gly Ile Tyr Met Pro Leu Gly Val Ile Ser Glu Thr Phe Leu Thr Pro
                    485                 490                 495

Ile Asn Ser Phe Gly Leu Glu Val Asp Ala Lys Ser Lys Thr Leu Thr
                500                 505                 510

Leu Lys Cys Lys Ser Tyr Leu Arg Glu Tyr Leu Leu Glu Ser Asp Leu
            515                 520                 525

Lys Asn Lys Glu Thr Gly Leu Ile Ala Pro Pro Asn Val Phe Ile Ser
530                 535                 540

Asn Val Val Lys Asn Asp Phe Glu Asp Gly Thr Val Met Ser Phe Gly
545                 550                 555                 560

Glu Ala Trp Gly Asp Ser Leu Lys Cys Ile Lys Lys Val Ser Val Ser
                    565                 570                 575

Gln Asp Leu Gln Arg Pro Gly Asn Lys Tyr Ala Leu Arg Leu Asp Val
                580                 585                 590

Glu Phe Asn Pro Asn Gly Trp Asp Gln Gly Asp Leu Gly Thr Trp
            595                 600                 605

Ile Gly Gly Val Val Glu Gly Gln Phe Asp Phe Thr Gly Tyr Lys Ser
610                 615                 620
```

Val Glu Phe Glu Met Phe Ile Pro Tyr Asp Glu Phe Ser Lys Ser Gln
625                 630                 635                 640

Gly Gly Phe Ala Tyr Lys Val Val Ile Asn Asp Gly Trp Lys Glu Leu
            645                 650                 655

Gly Ser Glu Phe Asn Ile Thr Ala Asn Ala Gly Lys Lys Val Lys Ile
                660                 665                 670

Asn Gly Lys Asp Tyr Thr Val Ile His Lys Ala Phe Ala Ile Pro Glu
            675                 680                 685

Asp Phe Arg Thr Lys Lys Arg Ala Gln Leu Val Phe Gln Phe Ala Gly
            690                 695                 700

Gln Asn Ser Asn Tyr Lys Gly Pro Ile Tyr Leu Asp Asn Val Arg Ile
705                 710                 715                 720

Arg Pro Glu Lys Leu Phe Glu Thr Pro Glu Ser Pro Glu Leu Ile Lys
                725                 730                 735

Phe Asn Asp Trp Glu Arg Phe Gly Thr Thr Tyr Ile Thr Gly Asn Glu
                740                 745                 750

Leu Arg Ile Asp His Ser Arg Gly Gly Tyr Phe Arg Gln Ser Leu Asn
            755                 760                 765

Ile Asp Ser Tyr Ser Thr Tyr Asp Leu Ser Phe Ser Phe Ser Gly Leu
770                 775                 780

Trp Ala Lys Val Ile Val Lys Asn Ser Arg Gly Val Val Leu Phe Glu
785                 790                 795                 800

Lys Val Lys Asn Asn Gly Ser Ser Tyr Glu Asp Ile Ser Glu Ser Phe
                805                 810                 815

Thr Thr Ala Ser Asn Lys Asp Gly Phe Phe Ile Glu Leu Thr Ala Glu
            820                 825                 830

Arg Thr Ser Ser Thr Phe His Ser Phe Arg Asp Ile Ser Ile Lys Glu
            835                 840                 845

Lys Ile Glu
    850

<210> SEQ ID NO 53
<211> LENGTH: 789
<212> TYPE: PRT
<213> ORGANISM: Artificial
<220> FEATURE:
<223> OTHER INFORMATION: Vip3Cd3_to_2BGP sequence

<400> SEQUENCE: 53

Met Asn Lys Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Asn Ile Tyr Leu Pro Lys Ile Thr Ser Met Leu Ser Asp Val
        115                 120                 125

```
Met Lys Gln Asn Tyr Ala Leu Ser Leu Gln Ile Glu Tyr Leu Ser Arg
    130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Ala Thr Glu Ser
                180                 185                 190

Thr Leu Arg Ala Lys Gln Gly Ile Phe Asn Glu Asp Ser Phe Asp Asn
            195                 200                 205

Asn Thr Leu Glu Asn Leu Thr Asp Leu Ala Glu Leu Ala Lys Ser Ile
    210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
                260                 265                 270

Ile Gly Lys Val Tyr Ser Phe Leu Ile Val Leu Thr Ser Leu Gln Ala
            275                 280                 285

Lys Ala Phe Leu Thr Leu Thr Thr Cys Arg Lys Leu Leu Gly Leu Ser
    290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
                340                 345                 350

Ile Leu Glu Ser Glu Pro Gly Tyr Ala Leu Val Gly Phe Glu Ile Ile
            355                 360                 365

Asn Asp Pro Ile Pro Val Leu Lys Ala Tyr Lys Ala Lys Leu Lys Gln
    370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415

Lys Asn Leu Thr Phe Pro Asp Gly Tyr Val Ile Thr Lys Ile Thr Phe
                420                 425                 430

Glu Lys Lys Leu Asn Asn Leu Ile Tyr Glu Ala Thr Ala Asn Phe Tyr
            435                 440                 445

Asp Pro Ser Thr Gly Asp Ile Asp Leu Asn Lys Lys Gln Val Glu Ser
    450                 455                 460

Thr Phe Pro Gln Thr Asp Tyr Ile Thr Met Asp Ile Gly Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
                500                 505                 510

Leu Lys Cys Lys Ser Tyr Leu Arg Glu Tyr Leu Leu Glu Ser Asp Leu
            515                 520                 525

Lys Asn Lys Glu Thr Gly Leu Ile Ala Pro Pro Asn Val Phe Ile Ser
530                 535                 540
```

Asn Val Val Lys Asn Thr Ala Ala Ser Ala Ser Ile Thr Ala Pro Ala
545                 550                 555                 560

Gln Leu Val Gly Asn Val Gly Glu Leu Gln Gly Ala Gly Ser Ala Val
                565                 570                 575

Ile Trp Asn Val Asp Val Pro Val Thr Gly Glu Tyr Arg Ile Asn Leu
            580                 585                 590

Thr Trp Ser Ser Pro Tyr Ser Ser Lys Val Asn Thr Leu Val Met Asp
        595                 600                 605

Gly Thr Ala Leu Ser Tyr Ala Phe Ala Glu Ala Thr Val Pro Val Thr
    610                 615                 620

Tyr Val Gln Thr Lys Thr Leu Ser Ala Gly Asn His Ser Phe Gly Val
625                 630                 635                 640

Arg Val Gly Ser Ser Asp Trp Gly Tyr Met Asn Val His Ser Leu Lys
                645                 650                 655

Leu Glu Leu Leu Gly Lys Leu Phe Glu Thr Pro Ser Pro Glu Leu
                660                 665                 670

Ile Lys Phe Asn Asp Trp Glu Arg Phe Gly Thr Thr Tyr Ile Thr Gly
            675                 680                 685

Asn Glu Leu Arg Ile Asp His Ser Arg Gly Gly Tyr Phe Arg Gln Ser
        690                 695                 700

Leu Asn Ile Asp Ser Tyr Ser Thr Tyr Asp Leu Ser Phe Ser Phe Ser
705                 710                 715                 720

Gly Leu Trp Ala Lys Val Ile Val Lys Asn Ser Arg Gly Val Val Leu
                725                 730                 735

Phe Glu Lys Val Lys Asn Asn Gly Ser Ser Tyr Glu Asp Ile Ser Glu
            740                 745                 750

Ser Phe Thr Thr Ala Ser Asn Lys Asp Gly Phe Phe Ile Glu Leu Thr
        755                 760                 765

Ala Glu Arg Thr Ser Ser Thr Phe His Ser Phe Arg Asp Ile Ser Ile
    770                 775                 780

Lys Glu Lys Ile Glu
785

<210> SEQ ID NO 54
<211> LENGTH: 812
<212> TYPE: PRT
<213> ORGANISM: Artificial
<220> FEATURE:
<223> OTHER INFORMATION: Vip3Cd3_to_GP21 sequence

<400> SEQUENCE: 54

Met Asn Lys Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

```
Met Leu Asn Ile Tyr Leu Pro Lys Ile Thr Ser Met Leu Ser Asp Val
            115                 120                 125

Met Lys Gln Asn Tyr Ala Leu Ser Leu Gln Ile Glu Tyr Leu Ser Arg
130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
            165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
        195                 200                 205

Asn Thr Leu Glu Asn Leu Thr Asp Leu Ala Glu Leu Ala Lys Ser Ile
    210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
            260                 265                 270

Ile Gly Lys Val Tyr Ser Phe Leu Ile Val Leu Thr Ser Leu Gln Ala
        275                 280                 285

Lys Ala Phe Leu Thr Leu Thr Thr Cys Arg Lys Leu Leu Gly Leu Ser
    290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
            340                 345                 350

Ile Leu Glu Ser Glu Pro Gly Tyr Ala Leu Val Gly Phe Glu Ile Ile
        355                 360                 365

Asn Asp Pro Ile Pro Val Leu Lys Ala Tyr Lys Ala Lys Leu Lys Gln
370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415

Lys Asn Leu Thr Phe Pro Asp Gly Tyr Val Ile Thr Lys Ile Thr Phe
            420                 425                 430

Glu Lys Lys Leu Asn Asn Leu Ile Tyr Glu Ala Thr Ala Asn Phe Tyr
        435                 440                 445

Asp Pro Ser Thr Gly Asp Ile Asp Leu Asn Lys Lys Gln Val Glu Ser
    450                 455                 460

Thr Phe Pro Gln Thr Asp Tyr Ile Thr Met Asp Ile Gly Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
            500                 505                 510

Leu Lys Cys Lys Ser Tyr Leu Arg Glu Tyr Leu Leu Glu Ser Asp Leu
        515                 520                 525

Lys Asn Lys Glu Thr Gly Leu Ile Ala Pro Pro Asn Val Phe Ile Ser
```

```
                      530                 535                 540
Asn Val Val Lys Asn Pro Ser Phe Glu Arg Gly Thr Glu Gly Tyr Thr
545                 550                 555                 560

Gly Trp Ser Gly Ile Ala Thr Val Val Thr Leu Gln Val Pro His Leu
                565                 570                 575

Gly Thr Lys Ala Ala Lys Leu Ala Ala Gly Gly Ser Ala Gly Val Gly
                580                 585                 590

Gln Lys Ile Ser Phe Lys Asp Arg Ser Tyr Lys Ile Gly Ile Trp
            595                 600                 605

Ala Lys Gln Asp Pro Asn Thr Thr Ile Gln Ser Thr Asp Asn Thr Lys
            610                 615                 620

Phe Arg Val Ala Asp Gly Asn Gly Leu Ile Ala Ser Lys Ala Tyr Gly
625                 630                 635                 640

Pro Phe Thr Ser Asn Trp Gln Glu Val Ser Trp Thr Trp Lys Ala Thr
                645                 650                 655

Lys Asp Val Leu Ala Asp Val Gln Phe Thr Ala Phe Leu Ser Ala Gly
                660                 665                 670

Ala Met Tyr Phe Asp Asp Phe Tyr Val Val Asp Val Lys Leu Phe Glu
            675                 680                 685

Thr Pro Glu Ser Pro Glu Leu Ile Lys Phe Asn Asp Trp Glu Arg Phe
690                 695                 700

Gly Thr Thr Tyr Ile Thr Gly Asn Glu Leu Arg Ile Asp His Ser Arg
705                 710                 715                 720

Gly Gly Tyr Phe Arg Gln Ser Leu Asn Ile Asp Ser Tyr Ser Thr Tyr
                725                 730                 735

Asp Leu Ser Phe Ser Phe Ser Gly Leu Trp Ala Lys Val Ile Val Lys
            740                 745                 750

Asn Ser Arg Gly Val Val Leu Phe Glu Lys Val Lys Asn Asn Gly Ser
            755                 760                 765

Ser Tyr Glu Asp Ile Ser Glu Ser Phe Thr Thr Ala Ser Asn Lys Asp
            770                 775                 780

Gly Phe Phe Ile Glu Leu Thr Ala Glu Arg Thr Ser Ser Thr Phe His
785                 790                 795                 800

Ser Phe Arg Asp Ile Ser Ile Lys Glu Lys Ile Glu
                805                 810

<210> SEQ ID NO 55
<211> LENGTH: 817
<212> TYPE: PRT
<213> ORGANISM: Artificial
<220> FEATURE:
<223> OTHER INFORMATION: Vip3Cd3_to_CenC sequence

<400> SEQUENCE: 55

Met Asn Lys Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asp Leu Thr Leu
            35                  40                  45

Asp Glu Ile Leu Lys Asn Gln Gln Leu Leu Asn Glu Ile Ser Gly Lys
        50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
```

```
                    85                  90                  95
Asn Gln Val Leu Asn Asp Val Asn Asn Lys Leu Asp Ala Ile Asn Thr
                100                 105                 110

Met Leu Asn Ile Tyr Leu Pro Lys Ile Thr Ser Met Leu Ser Asp Val
                115                 120                 125

Met Lys Gln Asn Tyr Ala Leu Ser Leu Gln Ile Glu Tyr Leu Ser Arg
                130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Ala Thr Glu Ser
                180                 185                 190

Thr Leu Arg Ala Lys Gln Gly Ile Phe Asn Glu Asp Ser Phe Asp Asn
                195                 200                 205

Asn Thr Leu Glu Asn Leu Thr Asp Leu Ala Glu Leu Ala Lys Ser Ile
                210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
                260                 265                 270

Ile Gly Lys Val Tyr Ser Phe Leu Ile Val Leu Thr Ser Leu Gln Ala
                275                 280                 285

Lys Ala Phe Leu Thr Leu Thr Thr Cys Arg Lys Leu Leu Gly Leu Ser
                290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
                340                 345                 350

Ile Leu Glu Ser Glu Pro Gly Tyr Ala Leu Val Gly Phe Glu Ile Ile
                355                 360                 365

Asn Asp Pro Ile Pro Val Leu Lys Ala Tyr Lys Ala Lys Leu Lys Gln
                370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415

Lys Asn Leu Thr Phe Pro Asp Gly Tyr Val Ile Thr Lys Ile Thr Phe
                420                 425                 430

Glu Lys Lys Leu Asn Asn Leu Ile Tyr Glu Ala Thr Ala Asn Phe Tyr
                435                 440                 445

Asp Pro Ser Thr Gly Asp Ile Asp Leu Asn Lys Lys Gln Val Glu Ser
                450                 455                 460

Thr Phe Pro Gln Thr Asp Tyr Ile Thr Met Asp Ile Gly Asp Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
                500                 505                 510
```

```
Leu Lys Cys Lys Ser Tyr Leu Arg Glu Tyr Leu Leu Glu Ser Asp Leu
            515                 520                 525

Lys Asn Lys Glu Thr Gly Leu Ile Ala Pro Pro Asn Val Phe Ile Ser
530                 535                 540

Asn Val Val Lys Asn Pro Gly Leu Glu Asp Gly Ile Asn Asn Trp Gln
545                 550                 555                 560

Ala Trp Gly Glu Gly Phe Thr Ala Ala Ser Asp Met Ser His Thr Gly
            565                 570                 575

Ser Ala Ser Leu Lys Val Leu Leu Asn Asn Gly Gly Arg Gln Val Val
            580                 585                 590

Ala Leu Gln Pro Gly Lys Ser Tyr Lys Leu Gly Val Trp Gly Lys Thr
            595                 600                 605

Ala Gly Thr Gly Thr Gly Thr Gln Thr Ala Thr Val Met Ile Asn Tyr
            610                 615                 620

Lys Lys Pro Glu Asp Asp Ser Ser His Thr Tyr Gly Ser Phe Gln Phe
625                 630                 635                 640

Gly Pro Asp Asn Ser Glu Phe Thr Tyr Lys Glu Ile Thr Phe Glu Thr
                645                 650                 655

Pro Asp Asp Met Ala Gln Glu Trp Gly Thr Gln Phe Val Ser Ile Trp
            660                 665                 670

Ser Glu Gly Ala Asp Gln Val Tyr Leu Asp Asp Phe Thr Leu Ser Glu
            675                 680                 685

Val Lys Leu Phe Glu Thr Pro Glu Ser Pro Glu Leu Ile Lys Phe Asn
            690                 695                 700

Asp Trp Glu Arg Phe Gly Thr Thr Tyr Ile Thr Gly Asn Glu Leu Arg
705                 710                 715                 720

Ile Asp His Ser Arg Gly Gly Tyr Phe Arg Gln Ser Leu Asn Ile Asp
                725                 730                 735

Ser Tyr Ser Thr Tyr Asp Leu Ser Phe Ser Phe Ser Gly Leu Trp Ala
                740                 745                 750

Lys Val Ile Val Lys Asn Ser Arg Gly Val Val Leu Phe Glu Lys Val
            755                 760                 765

Lys Asn Asn Gly Ser Ser Tyr Glu Asp Ile Ser Glu Ser Phe Thr Thr
            770                 775                 780

Ala Ser Asn Lys Asp Gly Phe Phe Ile Glu Leu Thr Ala Glu Arg Thr
785                 790                 795                 800

Ser Ser Thr Phe His Ser Phe Arg Asp Ile Ser Ile Lys Glu Lys Ile
                805                 810                 815

Glu

<210> SEQ ID NO 56
<211> LENGTH: 810
<212> TYPE: PRT
<213> ORGANISM: Artificial
<220> FEATURE:
<223> OTHER INFORMATION: Vip3Cd3_to_PSHGF7 sequence

<400> SEQUENCE: 56

Met Asn Lys Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asp Leu Thr Leu
            35                  40                  45
```

```
Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65              70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Asn Ile Tyr Leu Pro Lys Ile Thr Ser Met Leu Ser Asp Val
            115                 120                 125

Met Lys Gln Asn Tyr Ala Leu Ser Leu Gln Ile Glu Tyr Leu Ser Arg
    130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
    195                 200                 205

Asn Thr Leu Glu Asn Leu Thr Asp Leu Ala Glu Leu Ala Lys Ser Ile
    210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
            260                 265                 270

Ile Gly Lys Val Tyr Ser Phe Leu Ile Val Leu Thr Ser Leu Gln Ala
            275                 280                 285

Lys Ala Phe Leu Thr Leu Thr Thr Cys Arg Lys Leu Leu Gly Leu Ser
    290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
            340                 345                 350

Ile Leu Glu Ser Glu Pro Gly Tyr Ala Leu Val Gly Phe Glu Ile Ile
            355                 360                 365

Asn Asp Pro Ile Pro Val Leu Lys Ala Tyr Lys Ala Lys Leu Lys Gln
    370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415

Lys Asn Leu Thr Phe Pro Asp Gly Tyr Val Ile Thr Lys Ile Thr Phe
            420                 425                 430

Glu Lys Lys Leu Asn Asn Leu Ile Tyr Glu Ala Thr Ala Asn Phe Tyr
            435                 440                 445

Asp Pro Ser Thr Gly Asp Ile Asp Leu Asn Lys Lys Gln Val Glu Ser
    450                 455                 460

Thr Phe Pro Gln Thr Asp Tyr Ile Thr Met Asp Ile Gly Asp Asp Asp
```

```
            465                 470                 475                 480
Gly Ile Tyr Met Pro Leu Gly Val Ile Ser Glu Thr Phe Leu Thr Pro
            485                     490                 495
Ile Asn Ser Phe Gly Leu Glu Val Asp Ala Lys Ser Lys Thr Leu Thr
            500                 505                 510
Leu Lys Cys Lys Ser Tyr Leu Arg Glu Tyr Leu Leu Glu Ser Asp Leu
            515                 520                 525
Lys Asn Lys Glu Thr Gly Leu Ile Ala Pro Pro Asn Val Phe Ile Ser
            530                 535                 540
Asn Val Val Lys Asn Pro Gly Phe Glu Asp Asn Leu Ala Ser Trp Thr
545                 550                 555                 560
Asn Trp Gly Asn Thr Ser Ser Val Thr Ser Pro Ala Phe Ala Gly Ala
                565                 570                 575
Lys Ala Ala Arg Ile Ala Ser Gly Glu Gly Ala Gly Gln Ile Ile
            580                 585                 590
Pro Gly Ile Pro Ser Gly Thr Thr Tyr Val Leu Ser Gly His Gly Ser
            595                 600                 605
Val Ser Ala Gly Thr Asp Thr Ala Ile Val Gly Val Asp Cys Leu Asp
            610                 615                 620
Ala Asn Asn Asn Val Leu Ala Lys Asn Thr Leu Arg Phe Asn Gln Thr
625                 630                 635                 640
Leu Tyr Glu Phe Lys Ser Thr Ala Phe Thr Thr Val Pro Gly Thr Ala
            645                 650                 655
Lys Leu Gln Val Tyr Ile Tyr Lys Asn Ala Asp Ser Gly Ala Asn Ala
            660                 665                 670
Phe Leu Asp Asp Leu Ser Leu Val Glu Val Lys Leu Phe Glu Thr Pro
            675                 680                 685
Glu Ser Pro Glu Leu Ile Lys Phe Asn Asp Trp Glu Arg Phe Gly Thr
            690                 695                 700
Thr Tyr Ile Thr Gly Asn Glu Leu Arg Ile Asp His Ser Arg Gly Gly
705                 710                 715                 720
Tyr Phe Arg Gln Ser Leu Asn Ile Asp Ser Tyr Ser Thr Tyr Asp Leu
            725                 730                 735
Ser Phe Ser Phe Ser Gly Leu Trp Ala Lys Val Ile Val Lys Asn Ser
            740                 745                 750
Arg Gly Val Val Leu Phe Glu Lys Val Lys Asn Asn Gly Ser Ser Tyr
            755                 760                 765
Glu Asp Ile Ser Glu Ser Phe Thr Thr Ala Ser Asn Lys Asp Gly Phe
770                 775                 780
Phe Ile Glu Leu Thr Ala Glu Arg Thr Ser Ser Thr Phe His Ser Phe
785                 790                 795                 800
Arg Asp Ile Ser Ile Lys Glu Lys Ile Glu
            805                 810
```